United States Patent
Abbink et al.

(10) Patent No.: US 6,865,408 B1
(45) Date of Patent: *Mar. 8, 2005

(54) SYSTEM FOR NON-INVASIVE MEASUREMENT OF GLUCOSE IN HUMANS

(75) Inventors: Russell E. Abbink, Albuquerque, NM (US); Robert D. Johnson, Albuquerque, NM (US); John D. Maynard, Albuquerque, NM (US)

(73) Assignee: InLight Solutions, Inc., Albuquerque, NM (US)

( * ) Notice: Subject to any disclaimer, the term of this patent is extended or adjusted under 35 U.S.C. 154(b) by 44 days.

This patent is subject to a terminal disclaimer.

(21) Appl. No.: 10/378,237

(22) Filed: Mar. 3, 2003

Related U.S. Application Data

(63) Continuation-in-part of application No. 10/281,576, filed on Oct. 28, 2002, and a continuation-in-part of application No. 09/832,585, filed on Apr. 11, 2001, now Pat. No. 6,574,490, which is a continuation-in-part of application No. 09/832,586, filed on Apr. 11, 2001.

(51) Int. Cl.[7] ................................. A61B 5/00
(52) U.S. Cl. ....................... 600/310; 600/473
(58) Field of Search ................... 600/310, 316, 600/322, 473, 475

(56) References Cited

U.S. PATENT DOCUMENTS

| | | |
|---|---|---|
| 3,910,701 A | 10/1975 | Henderson et al. |
| 4,035,083 A | 7/1977 | Woodriff et al. |
| 4,142,797 A | 3/1979 | Astheimer |
| 4,169,676 A | 10/1979 | Kaiser |
| 4,260,220 A | 4/1981 | Whitehead |
| 4,427,889 A | 1/1984 | Muller |
| 4,537,484 A | 8/1985 | Fowler |
| 4,598,715 A | 7/1986 | Machler et al. |
| 4,653,880 A | 3/1987 | Sting et al. |
| 4,654,530 A | 3/1987 | Dybwad |
| 4,655,225 A | 4/1987 | Dahne et al. |
| 4,656,562 A | 4/1987 | Sugino |

(List continued on next page.)

FOREIGN PATENT DOCUMENTS

| | | |
|---|---|---|
| EP | 0 426 358 B1 | 5/1991 |
| EP | 0 449 335 A2 | 10/1991 |

(List continued on next page.)

OTHER PUBLICATIONS

U.S. Appl. No. 09/415,600, filed Oct. 8, 1999, Messerschmidt et al.

(List continued on next page.)

*Primary Examiner*—Eric F. Winakur
(74) *Attorney, Agent, or Firm*—Crompton, Seager & Tufte, LLC

(57) ABSTRACT

An apparatus and method for non-invasive measurement of glucose in human tissue by quantitative infrared spectroscopy to clinically relevant levels of precision and accuracy. The system includes six subsystems optimized to contend with the complexities of the tissue spectrum, high signal-to-noise ratio and photometric accuracy requirements, tissue sampling errors, calibration maintenance problems, and calibration transfer problems. The six subsystems include an illumination subsystem, a tissue sampling subsystem, a calibration maintenance subsystem, an FTIR spectrometer subsystem, a data acquisition subsystem, and a computing subsystem.

49 Claims, 54 Drawing Sheets

U.S. PATENT DOCUMENTS

| | | | |
|---|---|---|---|
| 4,657,397 A | | 4/1987 | Oehler et al. |
| 4,661,706 A | | 4/1987 | Messerschmidt et al. |
| 4,684,255 A | | 8/1987 | Ford |
| 4,712,912 A | | 12/1987 | Messerschmidt |
| 4,730,882 A | | 3/1988 | Messerschmidt |
| 4,787,013 A | | 11/1988 | Sugino et al. |
| 4,787,708 A | | 11/1988 | Whitehead |
| 4,830,496 A | | 5/1989 | Young |
| 4,853,542 A | | 8/1989 | Milosevic et al. |
| 4,857,735 A | | 8/1989 | Noller |
| 4,859,064 A | | 8/1989 | Messerschmidt et al. |
| 4,866,644 A | | 9/1989 | Shenk et al. |
| 4,867,557 A | | 9/1989 | Takatani et al. |
| 4,882,492 A | | 11/1989 | Schlager |
| 4,883,953 A | | 11/1989 | Koashi et al. |
| 4,975,581 A | | 12/1990 | Robinson et al. |
| 5,015,100 A | | 5/1991 | Doyle |
| 5,019,715 A | | 5/1991 | Sting et al. |
| 5,028,787 A | | 7/1991 | Rosenthal et al. |
| 5,051,602 A | | 9/1991 | Sting et al. |
| 5,068,536 A | | 11/1991 | Rosenthal |
| 5,070,874 A | | 12/1991 | Barnes et al. |
| 5,146,091 A | * | 9/1992 | Knudson ................... 600/310 |
| 5,158,082 A | | 10/1992 | Jones |
| 5,178,142 A | | 1/1993 | Harjunmaa et al. |
| 5,179,951 A | | 1/1993 | Knudson |
| 5,204,532 A | | 4/1993 | Rosenthal |
| 5,222,496 A | | 6/1993 | Clarke et al. |
| 5,223,715 A | | 6/1993 | Taylor |
| 5,225,678 A | | 7/1993 | Messerschmidt |
| 5,243,546 A | | 9/1993 | Maggard |
| 5,257,086 A | | 10/1993 | Fateley et al. |
| 5,267,152 A | | 11/1993 | Yang et al. |
| 5,268,749 A | | 12/1993 | Weber et al. |
| 5,291,560 A | | 3/1994 | Daugman |
| 5,303,026 A | | 4/1994 | Strobl et al. |
| 5,311,021 A | | 5/1994 | Messerschmidt |
| 5,313,941 A | | 5/1994 | Braig et al. |
| 5,321,265 A | | 6/1994 | Block |
| 5,331,958 A | | 7/1994 | Oppenheimer |
| 5,348,003 A | | 9/1994 | Caro |
| 5,355,880 A | | 10/1994 | Thomas et al. |
| 5,360,004 A | | 11/1994 | Purdy et al. |
| 5,361,758 A | | 11/1994 | Hall et al. |
| 5,372,135 A | | 12/1994 | Mendelson et al. |
| 5,379,764 A | | 1/1995 | Barnes et al. |
| 5,402,778 A | | 4/1995 | Chance |
| 5,419,321 A | | 5/1995 | Evans |
| 5,435,309 A | | 7/1995 | Thomas et al. |
| 5,441,053 A | | 8/1995 | Lodder et al. |
| 5,452,723 A | | 9/1995 | Wu et al. |
| 5,459,317 A | | 10/1995 | Small et al. |
| 5,459,677 A | | 10/1995 | Kowalski et al. |
| 5,460,177 A | | 10/1995 | Purdy et al. |
| 5,483,335 A | | 1/1996 | Tobias |
| 5,494,032 A | | 2/1996 | Robinson et al. |
| 5,515,847 A | | 5/1996 | Braig et al. |
| 5,523,054 A | | 6/1996 | Switalski et al. |
| 5,533,509 A | | 7/1996 | Koashi et al. |
| 5,537,208 A | | 7/1996 | Bertram et al. |
| 5,552,997 A | | 9/1996 | Massart |
| 5,596,992 A | | 1/1997 | Haaland et al. |
| 5,606,164 A | | 2/1997 | Price et al. |
| 5,636,633 A | | 6/1997 | Messerschmidt et al. |
| 5,655,530 A | | 8/1997 | Messerschmidt |
| 5,672,864 A | | 9/1997 | Kaplan |
| 5,672,875 A | | 9/1997 | Block et al. |
| 5,677,762 A | | 10/1997 | Ortyn et al. |
| 5,708,593 A | | 1/1998 | Saby et al. |
| 5,719,950 A | | 2/1998 | Osten et al. |
| 5,724,268 A | | 3/1998 | Sodickson et al. |
| 5,743,262 A | | 4/1998 | Lepper, Jr. et al. |
| 5,747,806 A | | 5/1998 | Khalil et al. |
| 5,750,994 A | | 5/1998 | Schlager |
| 5,782,755 A | | 7/1998 | Chance et al. |
| 5,792,050 A | | 8/1998 | Alam et al. |
| 5,792,053 A | | 8/1998 | Skladner et al. |
| 5,793,881 A | | 8/1998 | Stiver et al. |
| 5,808,739 A | | 9/1998 | Turner et al. |
| 5,818,048 A | | 10/1998 | Sodickson et al. |
| 5,823,951 A | | 10/1998 | Messerschmidt et al. |
| 5,828,066 A | | 10/1998 | Messerschmidt |
| 5,830,132 A | | 11/1998 | Robinson |
| 5,830,133 A | | 11/1998 | Osten et al. |
| 5,850,623 A | | 12/1998 | Carman, Jr. et al. |
| 5,853,370 A | | 12/1998 | Chance et al. |
| 5,860,421 A | | 1/1999 | Eppstein et al. |
| 5,886,347 A | | 3/1999 | Inoue et al. |
| 5,902,033 A | | 5/1999 | Levis et al. |
| 5,914,780 A | | 6/1999 | Turner et al. |
| 5,933,792 A | | 8/1999 | Andersen et al. |
| 5,935,062 A | | 8/1999 | Messerschmidt et al. |
| 5,945,676 A | | 8/1999 | Khalil |
| 5,949,543 A | | 9/1999 | Bleier et al. |
| 5,957,841 A | | 9/1999 | Maruo et al. |
| 5,961,449 A | | 10/1999 | Toida et al. |
| 5,963,319 A | | 10/1999 | Jarvis et al. |
| 6,005,722 A | | 12/1999 | Butterworth et al. |
| 6,016,435 A | | 1/2000 | Maruo et al. |
| 6,025,597 A | | 2/2000 | Sterling et al. |
| 6,026,314 A | | 2/2000 | Amerov et al. |
| 6,031,609 A | | 2/2000 | Funk et al. |
| 6,057,925 A | | 2/2000 | Anthon |
| 6,034,370 A | | 3/2000 | Messerschmidt |
| 6,040,578 A | | 3/2000 | Malin et al. |
| 6,041,247 A | | 3/2000 | Weckstrom et al. |
| 6,041,410 A | | 3/2000 | Hsu et al. |
| 6,043,492 A | | 3/2000 | Lee et al. |
| 6,044,285 A | | 3/2000 | Chaiken et al. |
| 6,045,502 A | | 4/2000 | Eppstein et al. |
| 6,046,808 A | | 4/2000 | Fately |
| 6,049,727 A | | 4/2000 | Crothall |
| 6,056,738 A | | 5/2000 | Marchitto et al. |
| 6,061,581 A | | 5/2000 | Alam et al. |
| 6,061,582 A | | 5/2000 | Small et al. |
| 6,066,847 A | | 5/2000 | Rosenthal |
| 6,070,093 A | | 5/2000 | Oosta et al. |
| 6,073,037 A | | 6/2000 | Alam et al. |
| 6,088,605 A | | 7/2000 | Griffith et al. |
| 6,100,811 A | | 8/2000 | Hsu et al. |
| 6,115,673 A | | 9/2000 | Malin et al. |
| 6,141,101 A | | 10/2000 | Bleier et al. |
| 6,147,749 A | | 11/2000 | Kubo et al. |
| 6,152,876 A | | 11/2000 | Robinson et al. |
| 6,157,041 A | | 12/2000 | Thomas et al. |
| 6,175,407 B1 | | 1/2001 | Sartor |
| 6,212,424 B1 | | 4/2001 | Robinson |
| 6,226,541 B1 | | 5/2001 | Eppstein et al. |
| 6,230,034 B1 | | 5/2001 | Messerschmidt et al. |
| 6,240,306 B1 | | 5/2001 | Rohrscheib et al. |
| 6,241,663 B1 | | 6/2001 | Wu et al. |
| 6,421,548 B1 | | 7/2002 | Berman et al. |
| 6,574,490 B2 | * | 6/2003 | Abbink et al. ............. 600/316 |

FOREIGN PATENT DOCUMENTS

| | | |
|---|---|---|
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 757 243 A1 | 2/1997 |
| EP | 0 788 000 A2 | 8/1997 |

| | | |
|---|---|---|
| EP | 0 801 297 A1 | 10/1997 |
| EP | 0 836 083 A1 | 4/1998 |
| EP | 0 869 348 A2 | 10/1998 |
| EP | 0 897 691 A2 | 2/1999 |
| EP | 0 317 121 B1 | 5/1999 |
| EP | 0 982 583 A1 | 3/2000 |
| EP | 0 990 945 A1 | 4/2000 |
| WO | WO 92/00513 | 1/1992 |
| WO | WO 92/17765 | 10/1992 |
| WO | WO 93/00855 | 1/1993 |
| WO | WO 93/07801 | 4/1993 |
| WO | WO 95/22046 | 8/1995 |
| WO | WO 97/23159 | 7/1997 |
| WO | WO 97/27800 | 8/1997 |
| WO | WO 97/28437 | 8/1997 |
| WO | WO 97/28438 | 8/1997 |
| WO | WO 98/01071 | 1/1998 |
| WO | WO 98/37805 | 9/1998 |
| WO | WO 98/40723 | 9/1998 |
| WO | WO 99/09395 | 2/1999 |
| WO | WO 99/37203 | 7/1999 |
| WO | WO 99/43255 | 9/1999 |
| WO | WO 99/46731 | 9/1999 |
| WO | WO 99/55222 | 11/1999 |
| WO | WO 99/56616 | 11/1999 |
| WO | WO 00/19889 | 4/2000 |

OTHER PUBLICATIONS

U.S. Appl. No. 09/563,865, filed May 3, 2000, Thomas et al.
U.S. Appl. No. 09/832,608, filed Apr. 11, 2001, Gardner et al.
U.S. Appl. No. 09/832,586, filed Apr. 11, 2001, Johnson.
U.S. Appl. No. 09/832,631, filed Apr. 11, 2001, Rowe et al.
Anderson, Robert J. et al., "Errors in Absorbance Measurements in Infrared Fourier Transform Spectrometry because of Limited Instrument Resolution," Analytical Chemistry, vol. 47, No. 14, Dec., 1975, pp. 2339–2347.
Anderson, Robert J. et al., "Resolution and Instrument Line Shape Effects on Spectral Compensation with Fourier Transform Infrared Spectrometers," Analytical Chemistry, vol. 50, No. 13, Nov. 1978, pp. 1804–1811.
Anderson, C. E. et al., "Fundamentals of Calibration Transfer Through Procrustes Analysis," Appln. Spectros., vol. 53, No. 10 (1999) p. 1268.
Ashbourn, Julian, Biometrics; Advanced Identity Verification, Springer, 2000, pp. 63–64).
Bantle, John P. et al., "Glucose Measurement in Patients with Diabetes Mellitus with Dermal Insterstital Fluid," Copyright © 1997 by Mosby–Year Book, Inc., 9 pages.
Blank, T.B. et al., "Transfer of Near–Infrared Multivariate Calibrations Without Standards," Anal. Chem., vol. 68 91996) p. 2987.
Brasunas John C. et al., "Uniform Time–Sampling Fourier Transform Spectroscopy," Applied Optics, vol. 36, No. 10, Apr. 1, 1997, pp. 2206–2210.
Brault, James W., "New Approach to High–Precision Fourier Transform Spectrometer Design," Applied Optics, Vo. 35, No. 16, Jun. 1, 1996, pp. 2891–2896.
Cassarly, W.J. et al., "Distributed Lighting Systems: Uniform Light Delivery," Source Unknown, pp. 1698–1702.
Chang, Chong–Min et al., "An Uniform Rectangular Illuminating Optical System for Liquid Crystal Light Valve Projectors," Euro Display '96 (1996) pp. 257–260.
Coyne, Lawrence J. et al., "Distributive Fiber Optic couplers Using Rectangular Lightguides as Mixing Elements," (Information Gatekeepers, Inc. Brookline, MA, 1979) pp. 160–164.

de Noord, Onno E., "Multivariate Calibration Standardization," Chemometrics and Intelligent Laboratory Systems 25, (1994) pp. 85–97.
Despain, Alvin M. et al., "A Large–Aperture Field–Widened Interferometer–Spectrometer for Airglow Studies," Aspen International Conference on Fourier Spectroscopy, 1970, pp. 293–300.
Faber, Nicolaas, "Multivariate Sensitivity for the Interpretation of the Effect of Spectral Pretreatment Methods on Near–Infrared Calibration Model Predictions," Analytical Chemistry, vol. 71, No. 3, Feb. 1, 1999, pp. 557–565.
Geladi, Paul et al., A Multivariate NIR Study of Skin Alterations in Diabetic Patients as Compared to Control Subjects, J. Nera Infrared Spectrosc., vol. 8 (2000) pp. 217–227.
Haaland, David M. et al. "Reagentless Near–Infrared Determination of Glucose in Whole Blood Using Multivariate Calbration," Applied Spectroscopy, vol. 46, No. 10 (1992) pp. 1575–1578.
Harwit, M. et al., "Chapter 5—Instrumental Considerations" Hadamard Transform Optics, Academic Press (1979) pp. 109–145.
Heise H. Michael et al., "Near–Infrared Reflectance Spectroscopy for Noninvasive Monitoring of Metabolites," Clin. Chem. Lab. Med. 2000, 38(2) (2000) pp. 137–145.
Heise, H.M. et al., "Near Infrared Spectrometric Investigation of Pulsatile Blood Flow for Non–Invasive Metabolite Monitoring," CP430, Fourier Transform Spectrsocopy: $11^{th}$ international Conference, (1998) pp. 282–285.
Heise, H.M. et al., "Noninvasive Blood Glucose Sensors Based on Near–Infrared Spectroscopy," Artif Organs, vol. 18, No. 6 (1994) pp. 1–9.
Heise, H.M. "Non–Invasive Monitoring of Metabolites Using Near Infrared Spectroscopy: State of the Art," Horm. Metab. Res., vol. 28 (1996) pp. 527–534.
Hopkins, George W. et al., "In–vivo NIR Diffuse–reflectance Tissue Spectrsocopy of Human Subjects," SPIE, vol. 3597, Jan. 1999, pp. 632–641.
Jagermann, Kay–Uwe et al. "Application of Near–Infrared Spectroscopy for Non–Invasive Determination of Blood/Tissue Glucose Using Neural Networks," Zeitschrift for Physikalische Chemie, Bd. 191, S. 179–190 (1995).
Khalil, Omar S., "Spectrsocopic and Clinical Aspects of Noninvasive Glucose Measurements," Clinical Chemistry, 45:2 (1999) pp. 165–177.
Kohl, Matthias et al., "The Influence of Glucose Concentration Upon the Transport of Light in Tissue–simulating Phantoms," Phys. Med. Biol., vol. 40 (1995) pp. 1267–1287.
Korte, E.H. et al., "Infrared Diffuse Reflectance Accessory for Local Analysis on Bulky Samples," Applied Spectrsocopy, vol. 42, No. 1, Jan. 1988, pp. 38–43.
Kumar, G. et al., "Optimal Probe Geometry for Near–Infrared Spectroscopy of Biologibal Tissue," Applied Spectroscopy, vol. 36 (1997) p. 2286.
Lorber, Avraham et al., "Local Centering in Multivariate Calibration," Journal on Chemometrics, vol. 10 (1996) pp. 215–220.
Lorber, Avraham et al., Net Analyte Signal Calculation in Multivariate Calbiration, Analytion Chemistry, vol. 69, No. 8, Apr. 15, 1997, pp. 1620–1626.
Marbach, Ralf, "Measurement Techniques for IR Spectroscopic Blood Glucose Determination," (1994) pp. 1–158.

Marbach, R. et al. "Noninvasive Blood Glucose Assay by Near–Infrared Diffuse Relfectance Spectroscopy of the Human Inner Lip," *Applied Spectroscopy*, vol. 47, No. 7 (1993) pp. 875–881.

Marbach, R. et al. "Optical Diffuse Reflectance Accessory for Measurements of Skin Tissue by Near–Infrared Spectroscopy," *Applied Optics*, vol. 34, No. 4, Feb. 1, 1995, pp. 610–621.

Mardia, K. V. et al., *Multivariate Analysis*, Acadmeic Press (1979) pp. 300–325.

Martens, Harald et al., Updating Multivariate Calibrations of Process NIR Instruments, *Adv. Instru. Control* (1990) pp. 371–381.

McIntosh, Bruce C. et al. Quantitative Reflectance Spectroscopy in the Mid–IR, *16th Annual FACSS Conference*, Oct. 1989.

Nichols, et al., *Design and Testing of a White–Light, Steady–State Diffuse Reflectance Spectometer for Determination of Optical Properties of Highly Scattering Systems*, Applied Otics, Jan. 1, 1997, 36(1), pp. 93–104.

Offner, A., "New Concepts in Projection Mask Aligners," *Optical Engineering*, vol. 14, No. 2, Mar.–Apr. 1975, pp. 130–132.

Osborne, B.G. et al., "Optical Matching of Near Infrared Reflectance Monochromator Instruments for the Analysis of Ground and Whole Wheat," *J. Near Infrared Spectrosc.*, vol. 7 (1999) p. 167.

Ozdemir, d. et al., "Hybrid Calibration Models: An Alternative to Calibration Transfer," *Appl. Spectros.*, vol. 52, No. 4 (1998) p. 599.

Powell, J.R. et al, "An Algorithm for the Reproducible Spectral Subtraction of Water from the FT–IR Spectra of Proteins in Dilute Solutions and Adsorbed Monolayers," *Applied Spectroscopy*, vol. 40, No. 3 (1986) pp. 339–344.

Ripley, B.D. *Pattern Recognition and Neural Networks*, Cambridge University Press (1996) pp. 91–120.

Robinson, M. Ries et al., "Noninvasive Glucose Monitoring in Diabetic Patients: A Preliminary Evaluation," *Clinical Chemistry*, vol. 38, No. 9 (1992) pp. 1618–1622.

Royston, David D. et al., "Optical Properties of Scattering and Absorbing Materials Used in the Development of Optical Phantoms at 1064 NM," *Journal of Biomedical Optics*, vol. 1, No. 1, Jan. 1996, pp. 110–116.

Rutan, Sarah C. et al., "Correction for Drift in Multivariate Systems Using the Kalman Filter," *Chemometrics and Intelligent Laboratory Systems 35*, (1996) pp. 199–211.

Salit, M.L. et al., "Heuristic and Statistical Algorithms for Automated Emission Spectral Background Intensity Estimation," *Applied Spectroscopy*, vol. 48, No. 8 (1994) pp. 915–925.

Saptari, Vidi Alfandi, "Analysis, Design and Use of a Fourier–Transform Spectrometer for Near Infrared Glucose Absorption Measurment," (Massachusetts Institutes of Technology, 1999) pp. 1–76.

Schmitt, J.M. et al., "Spectral Distortions in Near–Infrared Spectroscopy of Turbid Materials," *Applied Spectroscopy*, No. 50 (1996) p. 1066.

Service, F. John et al., Dermal Interstitial Glucose as an Indicator of Ambient Glycemia, *Diabetes Care*, vol. 20, No. 9, Sep. 1997, 9 pages.

Shroder, Robert, (Internet Article) MicroPac Forum Presentation, Current performance results, May 11, 2000.

Sjoblom, J. et al., "An Evaluation of Orthogonal Signal correction Applied to Calibration Transfer of NEar Infrared Spectra," *Chemom & Intell Lab. Sys.*, vol. 44 (1998) p. 229.

Steel, W.H., "Interferometers for Fourier Spectroscopy," Aspen International Conference on Fourier Spectrsocopy, (1970) pp. 43–53.

Sternberg R.S. et al., "A New Type of Michelson Interference Spectrometer," *Sci. Instrum.*, vol. 41 (1964) pp. 225–226.

Stork, Chris L. et al., "Weighting Schemes for Updating Regression Models—a Theoretical Approach," *Chemometrics and Intelligent Laboratory Systems 48*, (1999) pp. 151–166.

Sum, Stephen T. et al., "Standardization of Fiber–Optic Probes for Near–Infrared Mulitvariate Calibrations," *Applied Spectroscopy*, vol. 52, No. 6 (1998) pp. 869–877.

Swierenga, H. et al., "Comparison of Two Different Approaches Toward Model Transferability in NIR Spectroscopy," *Applied Spectroscopy*, vol. 52, No. 1 (1998) pp. 7–16.

Swierenga, H. et al., "Improvement of PLS Model Transferability by Robust Wavelength Selection," *Chemometrics and Intelligent Laboratory Systems*, vol. 41 (1998) pp. 237–248.

Swierenga, H. et al., "Strategy for Constructing Robust Multivariate Calibration Models," *Chemometrics and Intelligent Laboratory Systems*, vol. 49, (1999) pp. 1–17.

Teijido, J.M. et al., "Design of a Non–conventional Illumination System Using a Scattering Light Pipe," *SPIE*, Vo. 2774 (1996) pp. 747–756.

Teijido, J.M. et al., "Illumination Light Pipe Using Micro–Optics as Diffuser," *SPIE*, vol. 2951 (1996) pp. 146–155.

Thomas, Edward V. et al., "Development of Robust Multivariate Calibration Models," *Technometrics*, vol. 42, No. 2, May 2000, pp. 168–177.

Tipler, Paul A., *Physics, Second Edition*, Worth Publishers, Inc., Chapter 34, Section 34–2, Nov. 1983, pp. 901–908.

Wang, Y–D. et al., "Calibration Transfer and Measurement Stability of Near–Infrared Spectrometers," *Appl. Spectros.*, vol. 46, No. 5 (1992) pp. 764–771.

Wang, Y–D. et al., "Improvement of Multivariate Calibration Through Instrument Standardization," *Anal. Chem.*, vol. 64 (1992) pp. 562–564.

Wang, Z., "Additive Background Correction in Mulitvariate Instrument Standardization," *Anal. Chem.*, vol. 67 (1995) pp. 2379–2385.

Ward, Kenneth J. et al., "Post–Prandial Blood Glucose Determination by Quantitative Mid–Infrared Spectroscopy," *Applied Spectroscopy*, vol. 46, No. 6 (1992) pp. 959–965.

Webb, Paul, "Temperatures of Skin, Subcutaneous Tissue, Muscle and Core in Resting Men in Cold, Comfortable and Hot Conditions," *European Journal of Applied Physiology*, vol. 64 (1992) pp. 471–476.

Whitehead, L.A. et al., "High–efficiency Prism Light Guides with Confocal Parabolic Cross Sections," *Applied Optics*, vol. 37, No. 22 (1998) pp. 5227–5233.

* cited by examiner

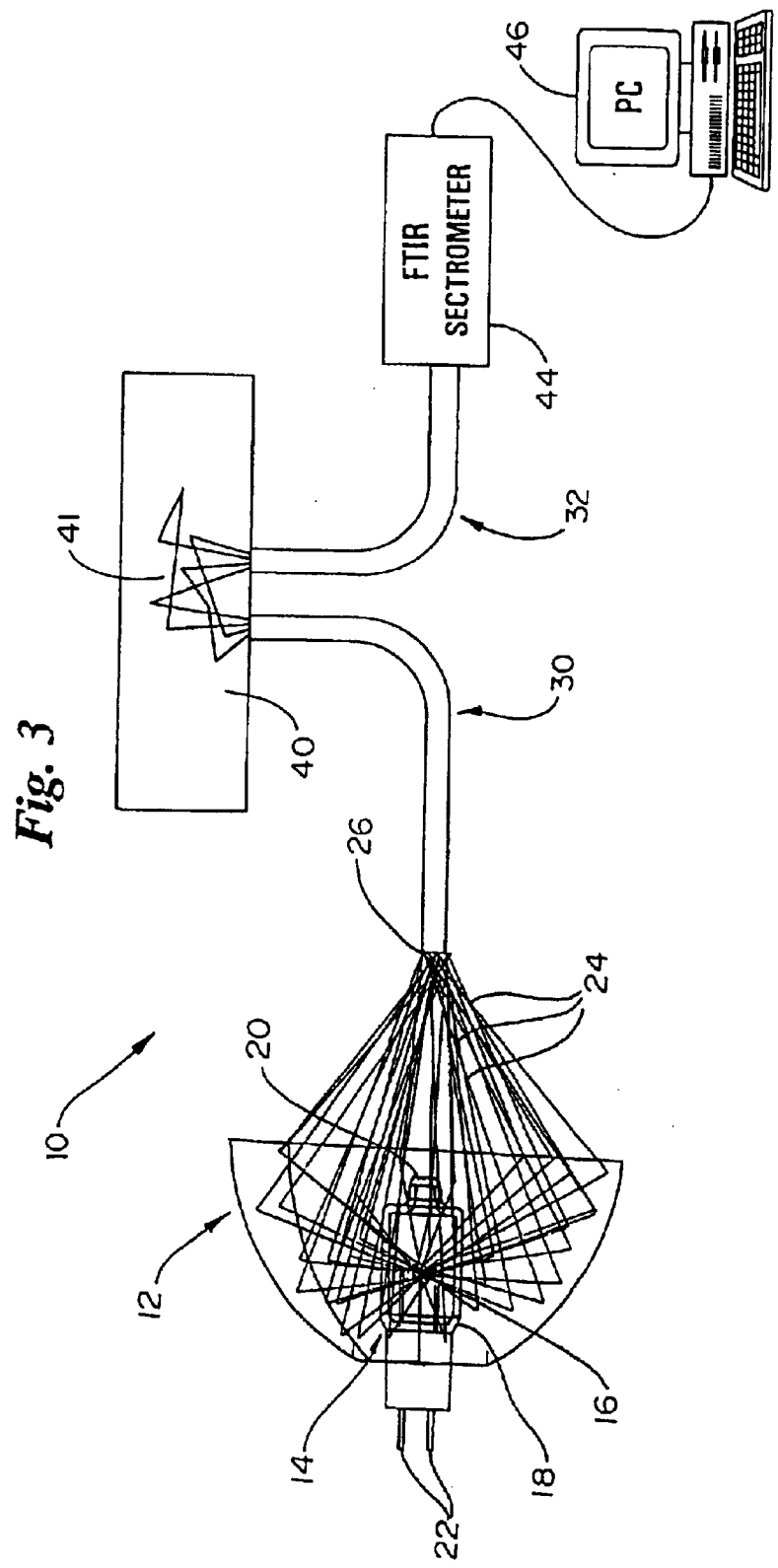

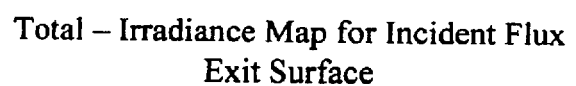
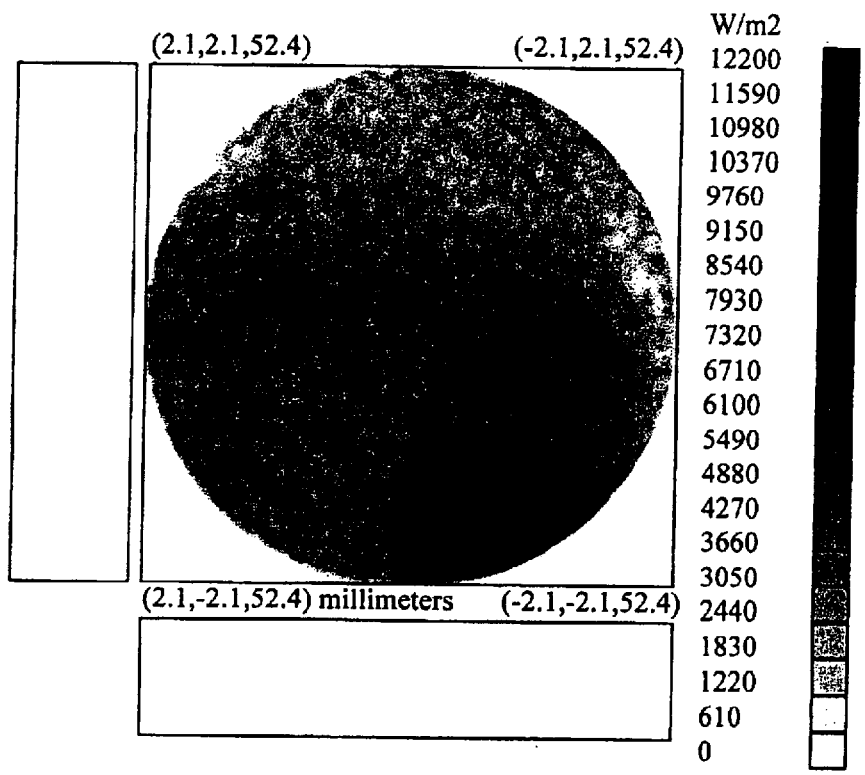

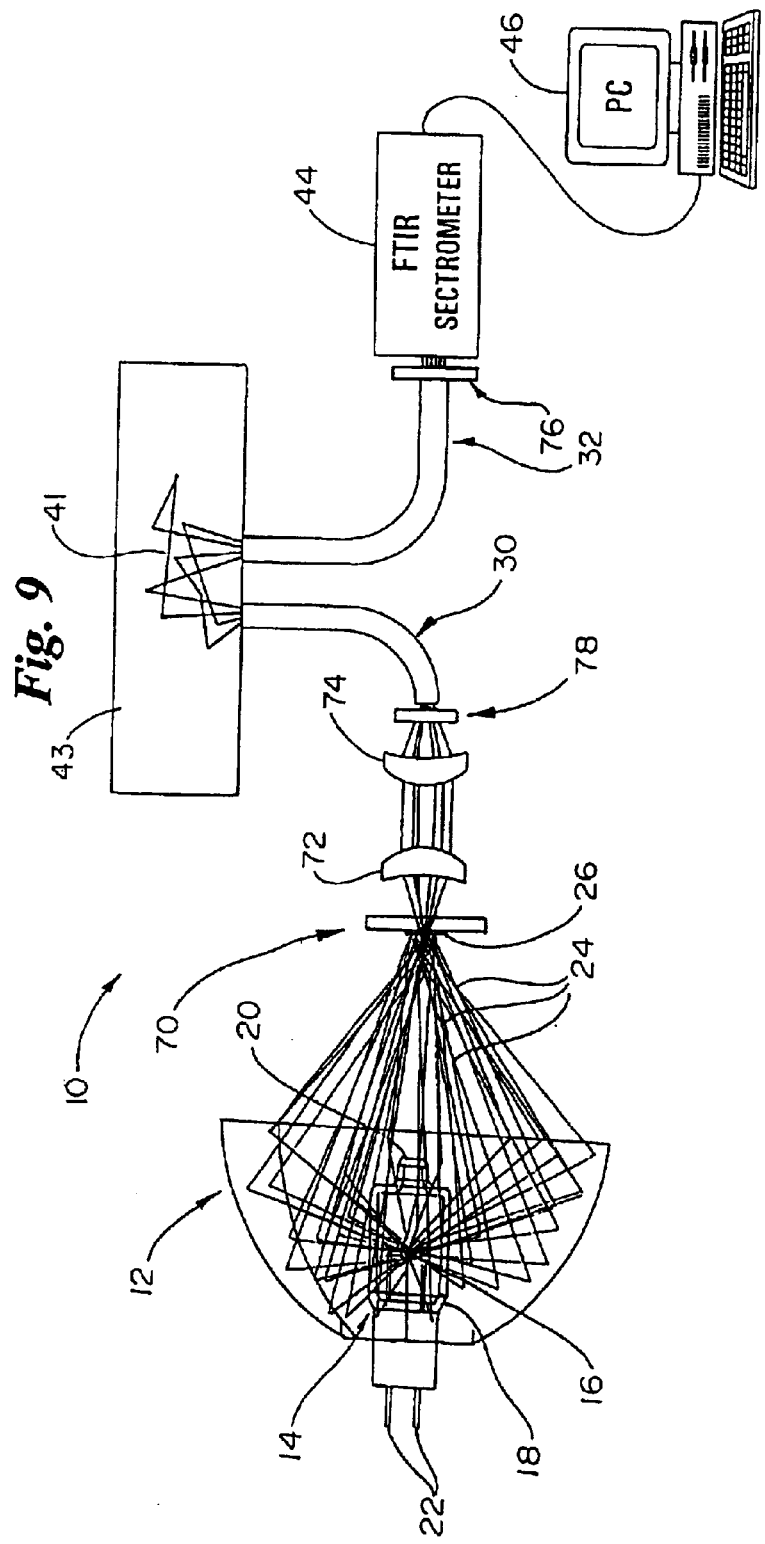

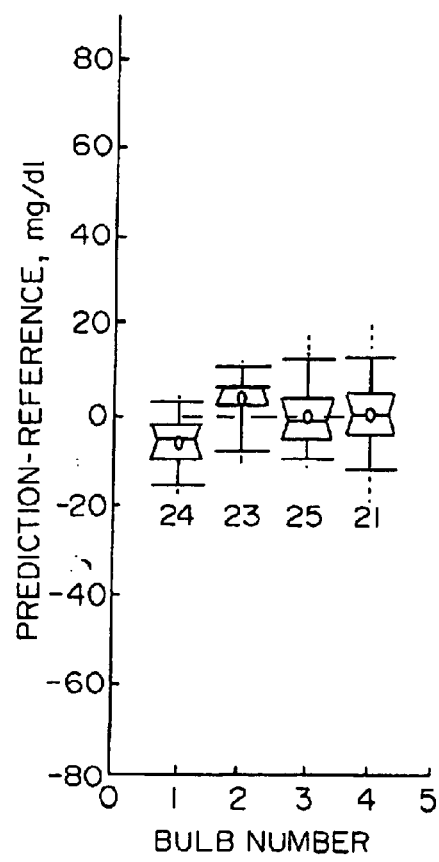 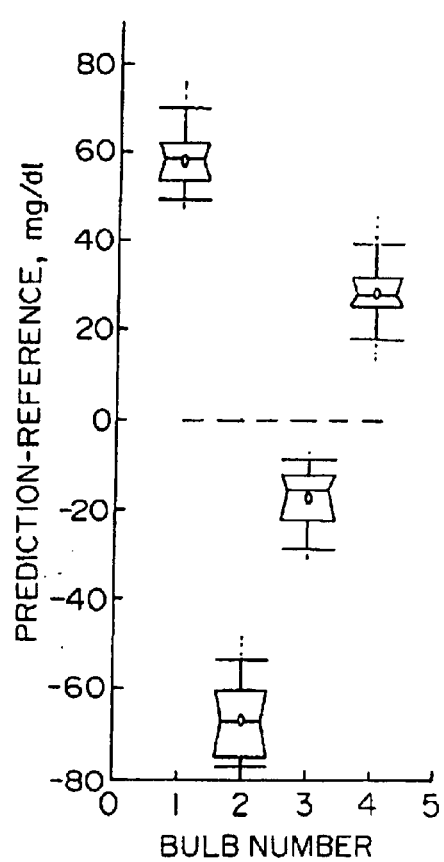
Fig. 10A
Fig. 10B

Irradiance Min:0.00032399 W/m2, Max:19613 W/m2,
Normalized Flux:0.17434 114383 Incident Rays Irradiance Min:5.3024e-005 W/m2, Max:14361 W/m2,
Normalized Flux:0.12676 86490 Incident Rays Data covers +/- 50.000 degrees from Normal
Collected Flux: 1.3936 W, 116196 Rays
Min:2.4814e-008 W/sr, Max:1.7072 W/sr,
Total Flux: 1.401 W

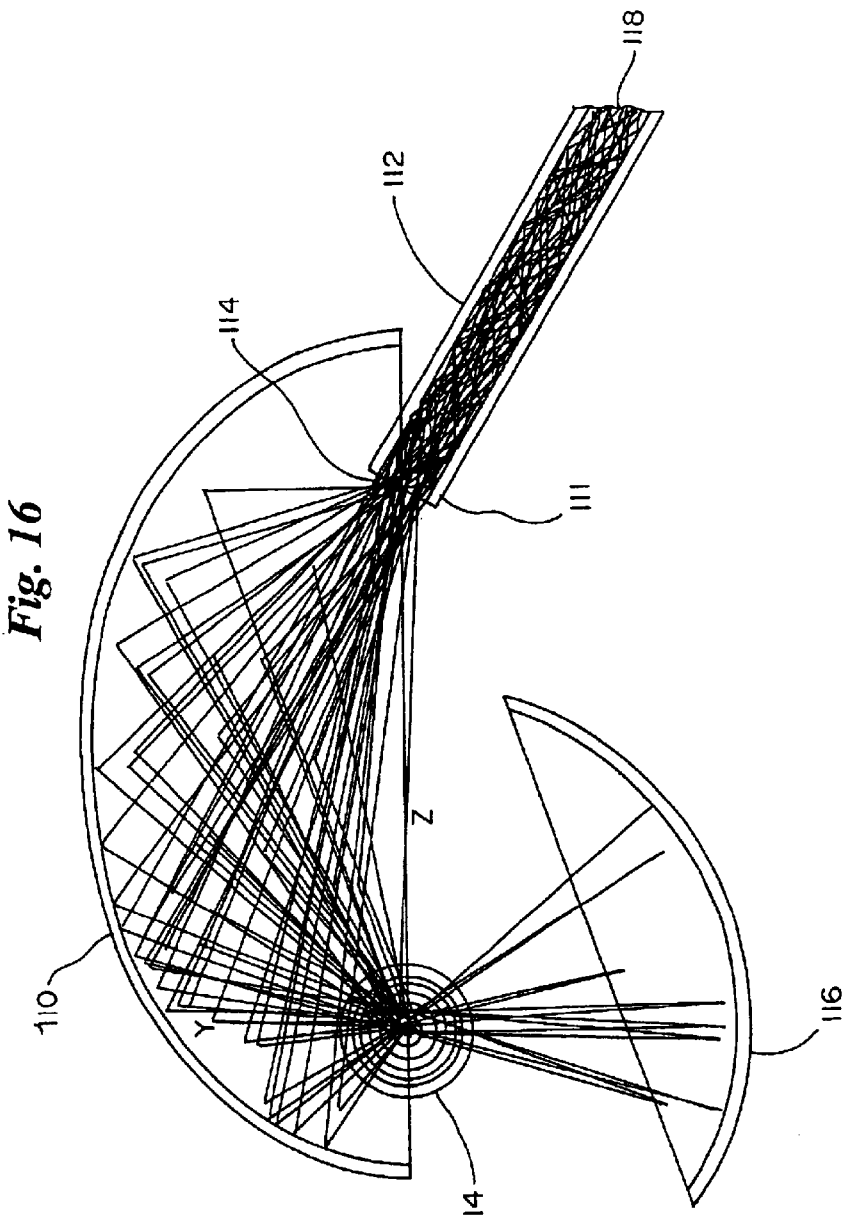

Data covers +/- 40.000 degrees from Normal

Data covers +/- 40.000 degrees from Normal

Irradiance Min:0.249e-005 W/m2, Max:3265.5 W/m2,
Normalized Flux:0.018369 16288 Incident Rays Polar Iso-Candela Plot
Using incident rays on Exit Surface Data covers +/- 50.000 degrees from Normal
Collected Flux: 7.1784W, 16288 Rays
Min:2.1681e-009 W/sr, Max:39.106W/sr,
Total Flux: 7.1784W

*Fig. 28*
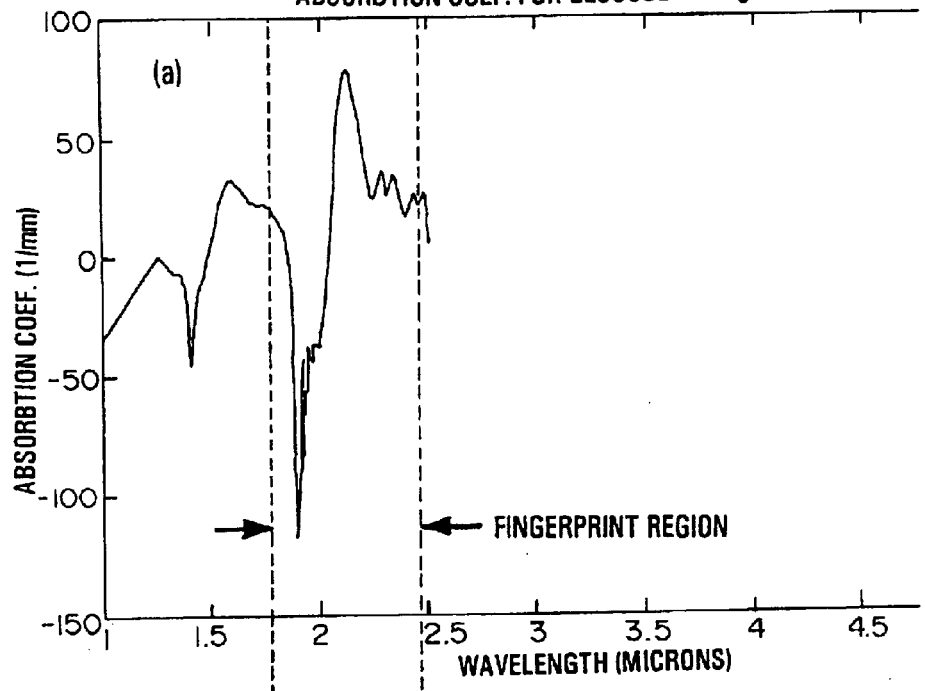
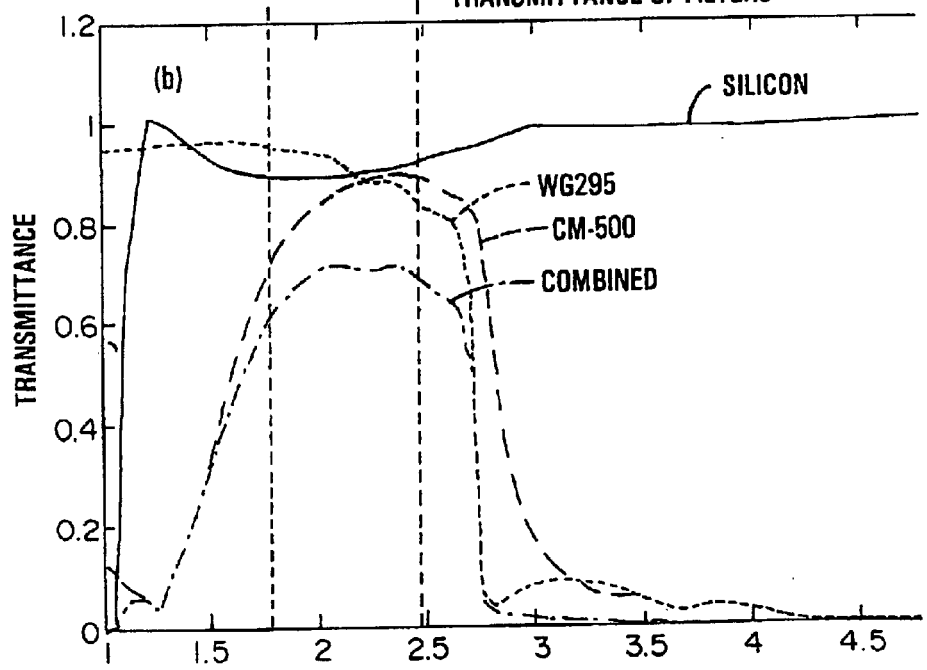

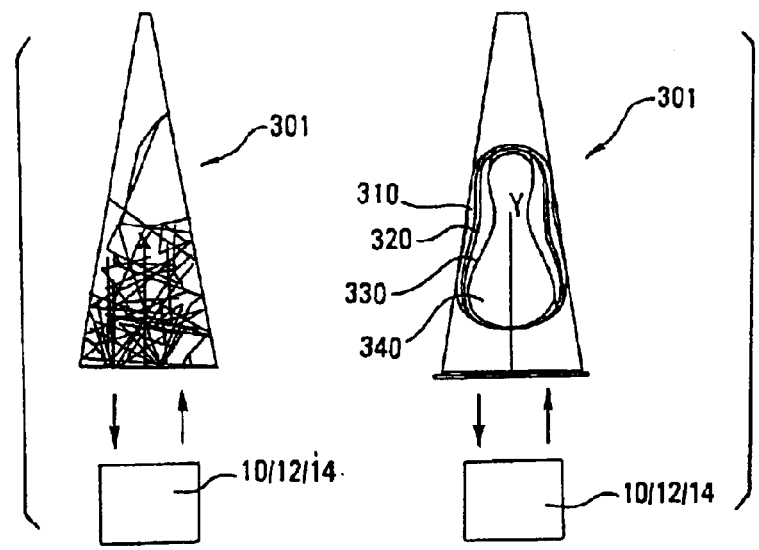
*Fig. 38*  *Fig. 39*
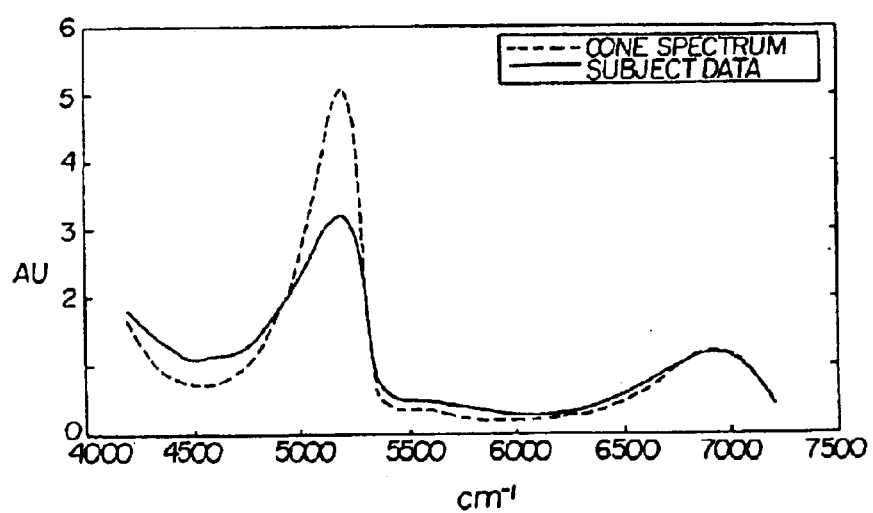
*Fig. 40*

CLARK ERROR GRID - SUMMER VALIDATION STUDY

SYSTEM FOR NON-INVASIVE MEASUREMENT OF GLUCOSE IN HUMANS

RELATED APPLICATIONS

This application claims priority under 35 U.S.C § 120 as a continuation in part of U.S. patent application Ser. No. 09/832,585, now U.S. Pat. No. 6,574,490, entitled "System For Non-Invasive Measurement Of Glucose In Humans," filed Apr. 11, 2001, incorporated herein by reference, and as a continuation in part of U.S. patent application Ser. No. 10/281,576, entitled "Optically Similar Reference Samples", filed Oct. 28, 2002, and as a continuation in part of U.S. patent application Ser. No. 09/832,586, filed Apr. 11, 2001 entitled "Illumination Device and Method for Spectroscopic Analysis"; incorporated herein by reference. This application is related to U.S. patent application Ser. No. 09/832,608, entitled "Optically Similar Reference Samples and Related Methods for Multivariate Calibration Models Used in Optical Spectroscopy"; and U.S. patent application Ser. No. 09/832,631, entitled "Encoded Variable Filter Spectrometer"; all assigned to the assignee of the present application. The disclosure of each of these related applications is hereby incorporated by reference.

TECHNICAL FIELD

The present invention generally relates to a quantitative spectroscopy system for measuring analyte concentrations or other attributes of tissue utilizing non-invasive techniques in combination with multivariate analysis. More specifically, the present invention relates to a quantitative near-infrared spectroscopy system, incorporating multiple subsystems in combination, providing precision and accuracy to measure analytes such as glucose at clinically relevant levels in human tissue.

BACKGROUND OF THE INVENTION

The non-invasive measurement of substances in the human body by quantitative spectroscopy has been found to be highly desirable, yet very difficult to accomplish. Non-invasive measurements via quantitative spectroscopy are desirable because they are painless, do not require a fluid draw from the body, carry little risk of contamination or infection, do not generate any hazardous waste and have short measurement times. A prime example of a desirable application of such technology is the non-invasive measurement of blood glucose levels in diabetic patients, which would greatly improve diabetes treatment. U.S. Pat. No. 5,379,764 to Bames et al. discloses the necessity for diabetics to frequently monitor blood glucose levels. The more frequent the blood glucose levels are measured, the less likely the occurrence of large swings in blood glucose levels. These large swings are associated with the very undesirable short-term symptoms and long-term complications of diabetes. Such long-term complications include heart disease, arteriosclerosis, blindness, stroke, hypertension, kidney failure and premature death.

Several systems have been proposed for the non-invasive measurement of blood glucose levels. These systems have included technologies incorporating polarimetry, mid-infrared spectroscopy, Raman spectroscopy, Kromoscopy, fluorescence spectroscopy, nuclear magnetic resonance spectroscopy, radio-frequency spectroscopy, ultrasound, transdermal measurements, photoacoustic spectroscopy and near-infrared spectroscopy. However, despite these efforts, direct and invasive measurements (e.g., blood sampling by a lancet cut into the finger) are still necessary for most, if not all, presently FDA approved and commercially available glucose monitors. Because invasive measurements are painful, inconvenient and costly to the diabetic patient, sufficiently frequent blood glucose measurement, which is necessary to ensure effective diabetes management, is rarely achieved.

Of particular interest to the present invention are prior art systems which incorporate or generally utilize quantitative infrared spectroscopy as a theoretical basis for the analysis. In general, these methods involve probing glucose-containing tissue using infrared radiation in absorption or diffuse reflectance mode. It is known that glucose absorbs at multiple frequencies in both the mid- and near-infrared range. There are, however, other infrared active analytes in the tissue and blood that also absorb at similar frequencies. Due to the overlapping nature of these absorption bands, no single or specific frequency can be used for reliable non-invasive glucose measurement. Analysis of spectral data for glucose measurement thus requires evaluation of many intensities over a wide spectral range to achieve the sensitivity, precision, accuracy, and reliability necessary for quantitative determination.

For example, Robinson et al. in U.S. Pat. No. 4,975,581 disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as glucose, but also may be any chemical or physical property of the sample. The method of Robinson et al. involves a two-step process that includes both calibration and prediction steps.

In the calibration step, the infrared light is coupled to calibration samples of known characteristic values so that there is attenuation of at least several wavelengths of the infrared radiation as a function of the various components and analytes comprising the sample with known characteristic value. The infrared light is coupled to the sample by passing the light through the sample or by reflecting the light off the sample. Absorption of the infrared light by the sample causes intensity variations of the light that are a function of the wavelength of the light. The resulting intensity variations at a minimum of several wavelengths are measured for the set of calibration samples of known characteristic values. Original or transformed intensity variations are then empirically related to the known characteristics of the calibration samples using multivariate algorithms to obtain a multivariate calibration model. The model preferably accounts for subject variability, instrument variability and environment variability.

In the prediction step, the infrared light is coupled to a sample of unknown characteristic value, and a multivariate calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

A further method of building a calibration model and using such model for prediction of analytes and/or attributes of tissue is disclosed in commonly assigned U.S. Pat. No. 6,157,041 to Thomas et al., entitled "Method and Apparatus for Tailoring Spectrographic Calibration Models," the disclosure of which is incorporated herein by reference.

In "Near-Infrared Spectroscopy for Non-invasive Monitoring of Metabolites", *Clinical Chemistry Lab Med* 2000, 38(2): 137–145, 2000, Heise et al. disclose the non-invasive measurement of glucose in the inner lip of a subject utilizing a Fourier transform infrared (FTIR) spectrometer and a diffuse reflectance accessory. The instrument used for this measurement contained a tungsten light source with an output that was collimated and sent into a Bruker FS-66 FTIR spectrometer. The FTIR spectrometer modulated the light in a manner that created an interferogram and the collimated interferogram was sent to a diffuse reflectance accessory. The diffuse reflectance accessory was a bifurcated, Y-shaped fiber optic probe. The input fibers of the probe radiated the inner lip of a subject or a spectralon reference standard with the interferogram from the FTIR spectrometer. Light diffusely reflected from the inner lip was collected by the output fibers of the diffuse reflectance accessory and focused onto a liquid nitrogen cooled InSb detector. The optical interferograms were converted to an electrical signal by the InSb detector and the electrical signal was digitized by an analog-to-digital converter (ADC). The digitized interferogram was then converted into an NIR spectrum and a collection of these spectra and corresponding blood glucose reference values were correlated using multivariate techniques to produce a calibration for non-invasive glucose measurements. This instrument was able to produce cross-validated, leave-one-out-at-a-time glucose standard error of predictions (SEP) of 36.4 mg/dl. This level of accuracy and precision is not of clinical utility.

In "Near-Infrared Spectrometric Investigation of Pulsatile Blood Flow for Non-Invasive Metabolite Monitoring", CP430, Fourier Transform Spectroscopy: 11$^{th}$ International Conference, 1998, Heise et al. discuss the non-invasive measurement of glucose in the inner lip of a subject using multivariate analysis of spectra with pulsatile blood flow. Heise et al. assert that by taking the difference between the systolic and diastolic portions of the cardiac cycle, interferences can be removed and glucose predictions are done on the spectra due to the additional blood volume. The optical pathlength due to the additional blood volume is 50 to 70 times shorter than an integrated NIR measurement, resulting in a dramatically reduced glucose signal-to-noise ratio (SNR). Heise used the instrument described in the preceding paragraph to make his measurements. No glucose prediction results were disclosed.

In "Spectroscopic and Clinical Aspects of Non-invasive Glucose Measurements", Clinical Chemistry, 45:2, 165–177, 1999, Khalil gives an overview of non-invasive glucose monitoring techniques. Khalil covers NIR transmission and reflectance, mechanical manipulation of the tissue coupled with NIR spectroscopy, Kromoscopy, spatially resolved diffuse reflectance, frequency domain measurements, polarimetry measurements, Raman spectroscopy and photo-acoustic methods.

In U.S. Pat. No. 5,361,758, Hall et al. describe a method and apparatus for the non-invasive measurement of glucose. This device is composed of a broadband light source, transfer optics from the light source to the sampling accessory, a tissue sampling accessory, transfer optics from the tissue sampling accessory to a dispersive spectrometer whose main optical elements are a diffraction grating and a linear array detector and finally processing and display subsystems. Hall et al. disclose taking the second derivative of the NIR absorbance spectrum collected by the above instrument and applying a calibration model to the second derivative of the absorbance spectrum to predict glucose concentrations.

In U.S. Pat. No. 5,743,262, Lepper, Jr. et al. describe a method and apparatus for the non-invasive measurement of glucose. This device is composed of a broadband light source, a collimating optic for the light source, an optical filter for modulating the output of the light source, a tissue sampling accessory, a photodetector, a data acquisition subsystem and a signal processing subsystem. The optical filter passes select wavelengths of light from the broadband source in a given time interval. The selected wavelength of light is sent into the tissue-sampling accessory to irradiate the tissue. Light collected from the tissue is focused onto a detector, and the electrical signal output from the detector is digitized by an analog-to-digital converter. The signal processing subsystem takes a "double log" transformation of the signal and then uses the result to predict glucose concentrations.

In U.S. Pat. No. 5,750,994, Schlager describes a method and apparatus for non-invasive measurement of glucose in the NIR range using optical transfer cells that have positive correlation filters that are selective for the analyte of interest. This apparatus includes a dispersive spectrometer along with a broadband light source, a tissue-sampling accessory, a detector or linear array detector and a data acquisition subsystem.

In U.S. Pat. No. 5,830,112, Robinson describes a general method of robust sampling of tissue for non-invasive analyte measurement. The sampling method utilizes a tissue-sampling accessory that is pathlength optimized by spectral region for measuring an analyte such as glucose. The patent discloses several types of spectrometers for measuring the spectrum of the tissue from 400 to 2500 nm, including acousto-optical tunable filters, discrete wavelength spectrometers, filters, grating spectrometers and FTIR spectrometers. The disclosure of Robinson is incorporated hereby reference.

In U.S. Pat. No. 6,016,435, Maruo et al. describe an apparatus for the non-invasive measurement of glucose. This device uses a broadband light source coupled to a stepped grating monochrometer to generate successive wavelengths of light in the NIR spectral region. The output of the monochrometer is sent to an optical fiber bundle that samples the tissue of a subject. The optical fiber bundle radiates the skin with the light from the monochrometer and collects diffusely reflected light from the skin of the subject. The collected diffuse reflectance spectrum is sent to a detector and the electrical signal from the detector is digitized. An absorbance spectrum is generated from the digitized output of the detector and that diffuse reflectance spectrum is used to make a prediction of glucose concentration.

In U.S. Pat. No. 6,026,314, Amerov et al. describe a method and apparatus for the non-invasive measurement of glucose that utilizes pulsed, discrete wavelengths of light in the NIR spectral region. The pulsed light source may be a flash lamp, light emitting diodes or laser diodes. The output of the pulsed light source is coupled to a tissue-sampling accessory that utilizes prisms or fiber optics to irradiate the tissue and collect absorbance spectra from the tissue. The output of the sampling accessory is sent to one or more detectors which convert the optical signal to an electrical signal. The electrical signals from the detectors are amplified and undergo analog-to-digital conversion. The digitized signals are then processed, and an algorithm is applied to predict glucose concentration.

In U.S. Pat. No. 6,049,727, Crothall describes an implanted glucose sensing system that measures glucose in vivo and is meant to couple to an insulin pump to create an artificial pancreas. The implanted sensor uses a number of discrete wavelengths which irradiate a blood vessel. The light is absorbed and scattered by the blood and tissue in the optical path between the light sources and the detector. The detected light is converted from an optical signal to an electrical signal, and then digitized by an analog-to-digital converter. The digitized signal is sent to a radio frequency transceiver which communicates with an external processing system to apply an algorithm to the digitized absorbance spectrum to calculate glucose concentration. The resulting glucose concentration information is utilized to control the administration of insulin to the subject by an insulin pump. This closed loop system is meant to create an artificial pancreas for insulin dependent diabetics.

In U.S. Pat. No. 6,061,582, Small et al. describe a method and apparatus for non-invasive determination of glucose. The apparatus for the measurement includes a broadband light source, an FTIR spectrometer, tissue sampling accessory, a detector and data acquisition system and a processing system. The spectra collected from the subject are digitally filtered to isolate a portion of the spectrum due to the glucose signal. Multivariate analysis techniques are then applied to the digitally filtered spectrum to generate a glucose prediction. The tissue-sampling accessory can collect spectra from the subject using transmission or diffuse reflectance.

In PCT Application, WO 99/43255, Small et al. describe a non-invasive glucose monitoring apparatus and method that measures glucose by transmission of NIR light through the tongue of a subject. The apparatus for the measurement includes a broadband light source, an FTIR spectrometer, tissue sampling accessory, a detector and data acquisition system and a processing system. The prediction results presented in this application do not achieve the levels of precision and accuracy necessary for clinical application.

In "New Approach to High-Precision Fourier Transform Spectrometer Design", *Applied Optics*, 35:16, 2891–2895, 1996, Brault introduces a constant time sampling analog-to-digital conversion technique for FTIR spectrometers that allows use of high dynamic range delta-sigma ADCs. Brault asserts their approach provides a superior technique for implementing the data acquisition system of an FTIR spectrometer because it avoids the artifacts of gain ranging and the need to precisely match the time delays between the laser reference and infrared measurement channels. In "Uniform Time-Sampling Fourier Transform Spectroscopy", *Applied Optics*, 36:1-, 2206–2210, 1997, Brasunas et al. discuss a variation of Brault's constant time sampling analog-to-digital conversion technique for FTIR spectrometers.

In U.S. Pat. No. 5,914,780, Turner et al. describe a method of digitizing the interferogram of an FTIR spectrometer using a constant time sampling analog-to-digital converter. The constant time sampling technique allows the use of high dynamic range, delta-sigma analog-to-digital converters that obviate the need for gain ranging circuitry and precisely matched delays between the reference laser and infrared signals. This type of data acquisition system is asserted to provide the FTIR spectrometer with higher SNR and superior photometric accuracy when compared to the previously employed sampling technique which is triggered by the zero crossings of the reference laser.

Although there has been substantial work conducted in attempting to produce a commercially viable non-invasive near-infrared spectroscopy-based glucose monitor, no such device is presently available. It is believed that prior art systems discussed above have failed for one or more reasons to fully meet the challenges imposed by the spectral characteristics of tissue which make the design of a non-invasive measurement system a formidable task. Thus, there is a substantial need for a commercially viable device which incorporates subsystems and methods with sufficient accuracy and precision to make clinically relevant measurements of analytes, such as glucose, in human tissue.

SUMMARY OF THE INVENTION

The present invention is directed to an apparatus and method for the non-invasive measurement of glucose in human tissue by quantitative infrared spectroscopy to clinically relevant levels of precision and accuracy. A clinically relevant level of precision and accuracy is defined as the measurement of glucose concentration in humans to a level of precision and accuracy such that a patient can base insulin dosing and/or diet modification on the glucose concentration measurement made by the noninvasive device. In addition, the noninvasive measurement has sufficient accuracy and precision such that either hypo-glycemia or hyper-glycemia can be diagnosed.

A Clark Error Grid provides a means to measure the clinical relevance of measurements on a system as compared to a reference measurement for measurements made over a period of time. With the present system acceptable, preferred and ideal Clark Error Grid data have been defined, each providing clinically relevant glucose measurements. An acceptable system includes a plot with 72% or greater in Region A, 24% or less in Region B. 1% or less in Region C, 3% or less in Region D and about 0% in Region E. A preferred system includes a plot with 85% or greater in Region A, 14.4% or less in Region B, 0.1% or less in Region C, 0.5% or less in Region D and about 0% in Region E. An ideal system includes a plot with 98.5% or greater in Region A, 1.5% or less in Region B and about 0% in Regions C, D and E. In one preferred system of the present invention, 80% or more predictions on a single subject within a physiological range of glucose fall in Region A of a Clark Error Grid. In this embodiment, it is also preferred that 18.5% or less fall in Region B, about 0% in Region C, 1.5% or less in Region D and about 0% in Region E.

If glucose concentration measurements are taken in a more continuous manner instead of several discrete measurements per day, the requirements for accuracy and precision can be relaxed and still maintain clinical relevance. It is recognized that the minimum threshold for percentage of measurements in each of the regions of the Clark Error Grid can depend on the peculiarities of the way the noninvasive measurement is taken, differences between individual subjects and/or other circumstances. The preferred standard for the noninvasive glucose measurement of the present invention is that it must allow the user to effectively maintain glycemic control and avoid either hypo-glycemic or hyper-glycemic conditions.

The present system overcomes the challenges posed by the spectral characteristics of tissue by incorporating a design which includes, in preferred embodiments, six highly optimized subsystems. The design contends with the complexities of the tissue spectrum, high signal-to-noise ratio and photometric accuracy requirements, tissue sampling errors, calibration maintenance problems, calibration transfer problems plus a host of other issues. The six subsystems include an illumination subsystem, a tissue sampling subsystem, a calibration maintenance subsystem, an FTIR spectrometer subsystem, a data acquisition subsystem, and a computing subsystem.

The present invention further includes apparatus and methods which allow for implementation and integration of each of these subsystems in order to ensure that the glucose net analyte signal-to-noise ratio is preserved to the maximum amount. The glucose net analyte signal is the portion of the near-infrared spectrum that is specific for glucose concentration levels because it is orthogonal to all other sources of spectral variance. The orthogonal nature of the glucose net analyte signal makes it perpendicular to the space defined by any interfering species and as a result, the net analyte signal is uncorrelated to these sources of variance. The glucose net analyte signal-to-noise ratio is directly related to the accuracy and precision of the present invention for non-invasive measurement of glucose by quantitative near-infrared spectroscopy.

The present invention preferably utilizes near-infrared radiation for analysis. Applicants have found that radiation in the wavelength range of 1.2 to 2.5 microns (or frequency range of 8000 to 4000 $cm^{-1}$) is of prime interest for making the present non-invasive measurements because such radiation has acceptable specificity for a number of analytes, including glucose, along with tissue optical penetration depths of up to 5 millimeters with acceptable absorbance characteristics. In the 1.2 to 2.5 micron spectral region, the large number of optically active substances that make up the tissue complicate the measurement of any given substance due to the overlapped nature of their absorbance spectra. Applicants have utilized herein multivariate analysis techniques which are believed required to resolve these overlapped spectra such that accurate measurements of the substance of interest can be achieved. Use of multivariate analysis techniques, however, also requires the maintenance and transfer of multivariate calibrations, which techniques Applicants have developed in order to accurately measure analytes, especially when trying to measure these analytes as weak absorbers found in the presence of much stronger absorbers, such as water.

A typical prior art non-invasive measurement system will have an illumination subsystem which generates the near-infrared light, a tissue sampling accessory which irradiates and collects light from the tissue, a spectrometer, a data acquisition subsystem, a reference device for calibration maintenance and a processing unit. Each of these subsystems has significant influence on the accuracy of the non-invasive measurement. The present invention documents a multidisciplinary approach to the design of the present instrument which incorporates an understanding of the instrument subsystems, tissue physiology, multivariate analysis, near-infrared spectroscopy and overall system operation. Further, the interactions between the subsystems have been analyzed so that the behavior and requirements for the entire non-invasive measurement device are well understood and result in a design for a commercial instrument that will make non-invasive measurements with sufficient accuracy and precision at a price and size that is commercially viable.

The subsystems of the non-invasive glucose monitor are highly optimized to provide reproducible and, preferably, uniform radiance of the tissue, low tissue sampling error, depth targeting of the glucose-bearing layers of the tissue, efficient collection of diffuse reflectance spectra from the tissue, high optical throughput, high photometric accuracy, large dynamic range, excellent thermal stability, effective calibration maintenance, effective calibration transfer, built-in quality control and ease-of-use. All of these factors have been considered as important to maximize the glucose net analyte signal-to-noise ratio and provide clinically relevant levels of prediction accuracy and precision for the administration of insulin therapy and other therapies related to the detection and management of diabetes. The present invention has been found to provide clinically relevant levels of glucose prediction and accuracy over a minimum of two months for a diverse subject population. With the present system, the overall standard error of prediction for 40 subjects over a 7-week validation study was 21.7 mg/dl. Further, as shown in FIG. 56, 83.5% of the data was within section "A" of a Clark Error Grid, 15.4% in section "B", 0% in section "C", 1.1% in section "D" and 0% in section "E".

BRIEF DESCRIPTION OF THE DRAWINGS

FIG. 3 is a diagramed view of a system for measuring the concentration of an analyte within biological tissue;

FIG. 4b is an incidance plot showing the changes in spatial distribution of emitted radiation after a 90-degree rotation of the filament used in producing the incidance plot of FIG. 4a;

FIG. 4c is an incidance plot showing the changes in spatial distribution of emitted radiation after a one-millimeter vertical translation of the filament used in producing the incidance plot of FIG. 4a;

FIG. 5b is an intensity plot showing the changes in angular distribution of emitted radiation after a 90-degree rotation of the filament used in producing the intensity plot of FIG. 5a;

FIG. 5c is an intensity plot showing the changes in angular distribution of emitted radiation after a one-millimeter vertical translation of the filament used in producing the intensity plot of FIG. 5a;

FIG. 9 is a diagramed view of a system used for cross-validation analysis for baseline system performance using a tissue phantom for the sample source;

FIG. 10a is a box and whisker plot of cross-validated prediction errors for the system illustrated in FIG. 9, in the absence of a lamp change;

FIG. 10b is a box and whisker plot of cross-validated prediction errors for the system illustrated in FIG. 9, with the inclusion of lamp changes;

FIG. 14b is an incidance plot showing the changes in spatial distribution of emitted radiation after a 90-degree rotation of the filament used in producing the incidance plot of FIG. 14a;

FIG. 14c is an incidance plot showing the changes in spatial distribution of emitted radiation after a one-millimeter vertical translation of the filament used in producing the incidance plot of FIG. 14a;

FIG. 15b is an intensity plot showing the changes in angular distribution of emitted radiation after a 90-degree rotation of the filament used in producing the intensity plot of FIG. 15a;

FIG. 15c is an intensity plot showing the changes in angular distribution of emitted radiation after a one-millimeter vertical translation of the filament used in producing the intensity plot of FIG. 15a;

FIG. 16 is a schematic plan view of an alternative source and light pipe system of the present invention;

FIG. 28 graphically depicts the transmittance of selected wavelengths in a preferred fingerprint region;

FIGS. 38 and 39 illustrate a cone background device in accordance with an embodiment of the present invention, wherein FIG. 38 illustrates a ray-trace of the cone background device and FIG. 39 illustrates a partial cut-away view of the cone background device;

FIG. 40 shows a graph of spectral response demonstrating the spectral match between the tissue sample and the cone background;

DETAILED DESCRIPTION OF THE PREFERRED EMBODIMENTS

The following detailed description should be read with reference to the drawings in which similar elements in different drawings are numbered the same. The drawings, which are not necessarily to scale, depict illustrative embodiments that are not intended to limit the scope of the invention.

Figure 1:
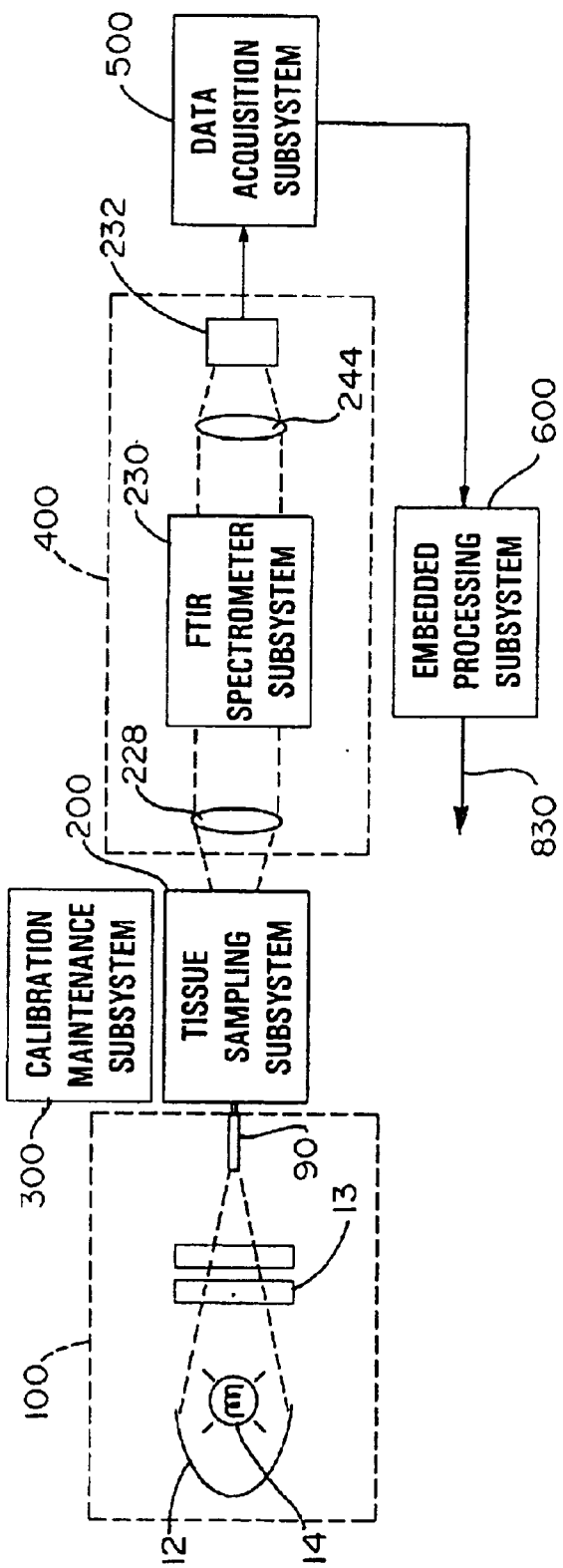
FIG. 1 is a schematic depiction of a non-invasive spectrometer system incorporating the subsystems of the present invention.

Referring now to FIG. 1, a non-invasive glucose monitor system that is able to achieve clinically relevant levels of accuracy and precision is depicted in schematic view. The overall system includes six subsystems. The subsystems include an illumination subsystem 100, a tissue sampling subsystem 200, a calibration maintenance subsystem 300, an FTIR spectrometer subsystem 400, a data acquisition subsystem 500 and an embedded processing subsystem 600. The subsystems have been designed and carefully integrated in order to ensure that the glucose net analyte signal-to-noise ratio is preserved to the maximum amount. The glucose net analyte signal is the portion of the near-infrared spectrum that is specific for glucose concentration levels because it is orthogonal to other sources of spectral variance. The glucose net analyte signal-to-noise ratio is directly related to the accuracy and precision of the non-invasive measurement of glucose by quantitative near-infrared spectroscopy with the present invention.

The subsystems provide reproducible and preferably uniform radiance of the tissue, low tissue sampling error, depth targeting of the glucose-bearing layers of the tissue, efficient collection of diffuse reflectance spectra from the tissue, high optical throughput, high photometric accuracy, large dynamic range, excellent thermal stability, effective calibration maintenance, effective calibration transfer, built-in quality control and ease-of-use. Each of these factors are optimized to maximize the glucose net analyte signal-to-noise ratio which results in clinically relevant levels of glucose prediction accuracy for insulin therapy. Each of the subsystems is discussed below in detail followed by experimental evidence documenting that a preferred embodiment of the present system provides clinically relevant levels of precision and accuracy in glucose analysis in tissue.

The illumination subsystem 100 generates the near-infrared (NIR) light used to interrogate the tissue of a human for the non-invasive measurement of glucose. The illumination subsystem, in an exemplary embodiment, contains a broadband, polychromatic light source 14 that emits radiation in the NIR portion of the spectrum. The light source 14 may emit radiation outside of the NIR, also. An example of a suitable light source 14 would be a 40-watt, 22.8-volt tungsten filament lamp. The light source 14 is typically driven by a tightly regulated power supply. The power supply may supply the lamp with constant current, constant voltage or constant power. The power supply for the light source should provide tight regulation of current, voltage or power to keep the color temperature and emissivity of the light source as stable as possible. Fluctuations of the light source's color temperature and emissivity are a source of noise in the non-invasive glucose measurement and can reduce the net analyte SNR and, subsequently, the accuracy and precision of the measurement. In preferred embodiments, the overall system of the present invention includes a power supply which provides regulated, low noise power to all of the subsystems. The power supply is preferably a 300-watt, quad output, resonant power, medical grade, AC power to DC converter that provides output voltages of +28, +15, −15, and +5 VDC. The ripple on each of the voltages is less than 20 millivolts peak-to-peak and the switching frequency of the supply is greater than 200 kilohertz to facilitate additional filtering of the power and to further reduce noise. Additionally, the power supply has a conversion efficiency of at least 80% which is important to reduce the thermal loading of the non-invasive monitor to the point that only convection cooling is required for normal device operation. The illumination subsystem 100 utilizes the 28 VDC power from the power supply to drive the light source. A DC-to-DC converter tightly regulates the input power down to 21.4 VDC and also provides a soft start function that gradually turns on the light source when the non-invasive glucose monitor is first turned on. The soft start function extends the useful life of the light source by eliminating startup transients and limiting the current required to initially power the light source.

In addition to the light source and regulated power supply, the illumination subsystem will contain optical elements 12,13,90 that collect the radiation from the light source and transfer that light to the input of the tissue sampling subsystem. The elements that makeup the transfer optics may include collimating and/or condensing optics, optical filters, optical diffusers, a homogenizer or light pipe for scrambling and the corresponding mechanical components to hold the optics and light source.

The collimating optics may be refractive or reflective elements. An example of a refractive collimating optic would be a lens. An example of a reflective collimating optic would be a parabolic mirror. The condensing optics may also be refractive or reflective. An example of a refractive condensing optic would be a lens. An example of a reflective condensing optic would be an elliptical mirror. The materials for lenses and mirrors are well known in the art. The reflective optics may have a smooth finish, a rough finish or a faceted finish depending on the configuration of the illumination subsystem. The purpose of the rough or faceted finishes for the reflective optics is to destroy the coherence of the light source image to create a more uniform radiance pattern. The refractive optics can be spherical or aspherical. The Fresnel lens is a special type of aspherical lens that also may be employed. The purpose of the collimating and/or condensing optics is to collect radiation from the source and transfer the radiation to the input of the tissue sampling subsystem 200 or to other optical elements that perform additional operations on the light before it is passed to the tissue sampling subsystem 200.

One or more optical filters 13 may be employed to preferentially pass radiation only in the spectral region of interest. The optical filter may be one or a combination of long pass, short pass, or band pass filters. These filters can be absorptive, interference or dichroic in nature. In some embodiments, the optical filters are anti-reflection coated to preserve the transmittance of light in the spectral region of interest. These filters may also perform spectral shaping of the radiation from the light source to emphasize certain portions of the NIR spectrum over others. The optical filtering is typically done to bandlimit the radiation impinging on the tissue to increase the SNR in the region of interest and to keep from burning or otherwise damaging the tissue of the subject. Bandlimiting the radiation improves the effective SNR by reducing detector Shot noise that results from unwanted radiation outside the spectral region of interest.

The purpose of the optical diffusers 13 and scramblers 90 in the illumination subsystem is to provide reproducible and, preferably, uniform radiance at the input of the tissue sampling subsystem 200. It has been found that uniform radiance is necessary to ensure good photometric accuracy and even illumination of the tissue. Uniform radiance is also necessary to reduce errors associated with manufacturing differences between light sources. Uniform radiance is utilized in the present invention for achieving accurate and precise non-invasive glucose measurements.

An example of an optical diffuser is a ground glass plate. The ground surface of the plate effectively scrambles the angle of the radiation emanating from the light source and its transfer optics. A light pipe is used to scramble the intensity of the radiation such that the intensity is uniform at the output of the light pipe. In addition, light pipes with a double bend will scramble the angles of the radiation. For creation of uniform intensity and angular distribution, the cross section of the light pipe should not be circular. Square, hexagonal and octagonal cross sections are effective scrambling geometries. The output of the light pipe may directly couple to the input of the tissue sampler or may be used in conjunction with additional transfer optics before the light is sent to the tissue sampler. Exemplary illumination subsystems are disclosed below and in commonly assigned U.S. patent application Ser. No. 09/832,586, filed on the same date herewith and entitled "Illumination Device and Method for Spectroscopic Analysis", the disclosure of which is incorporated herein by reference.

Figure 2:
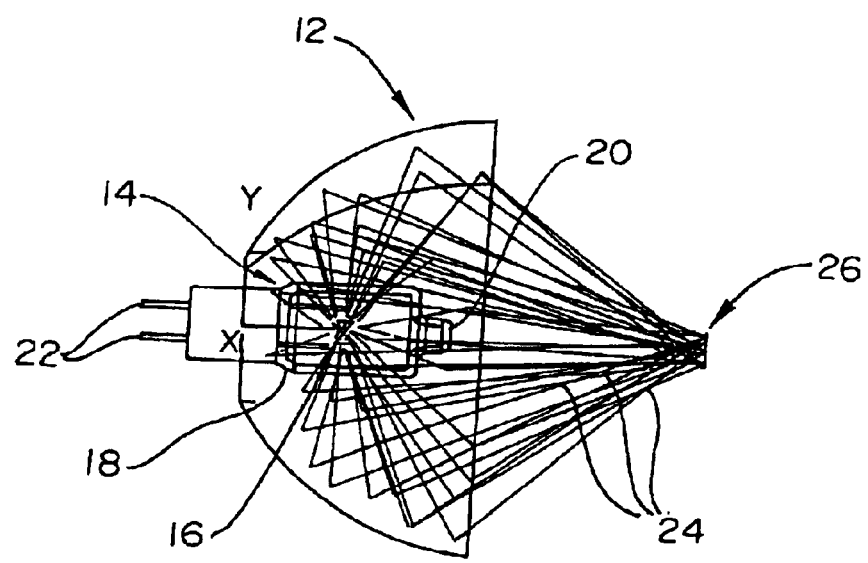
FIG. 2 is a detailed perspective view of an infrared radiation source lamp known in the art.

FIG. 2 shows a plan view of an infrared radiation source lamp 14 known in the art. The appearance of a radiant source lamp 14 closely resembles that of a traditional residential light bulb. Traditional spectrophotometer lamps consist of a filament 16 housed within a transparent envelope 18, or the like. The transparent envelope 18 is either comprised of a silicate glass, fused silica or quartz material. The material used for the glass envelope 18 is dependent upon the wavelength regions being surveyed on the electromagnetic spectrum.

The envelope 18 traditionally is cylindrical or oval in shape. The lamp 14 of FIG. 2 specifically is of a closed-end cylindrical variety. The closed-end portion of the cylinder has a nipple 20 positioned near the center of the cylinder's closed-end base. The nipple 20 formation is a result of manufacturing and functionally has no beneficial purpose. On the other hand, the nipple 20, as will be discussed in detail later, affects the emission of radiant energy.

Filament 16, and subsequently lamp choice, is wavelength dependent. Operating in the infrared and near infrared regions of the electromagnetic spectrum requires a radiation source filament 16 applicable to those spectral regions. Several continuous radiation sources including tungsten-halogen lamps, tungsten lamps, nerst glowers, nichrome wires and globars are suitable for infrared molecular absorption spectroscopy. The desired filament is manufactured so as to place the filament 16 within the open end of the glass envelope 18 and securely fastened thereto. Wires or leads 22 emerge from the filament 16 and out of the glass envelope 18 attaching the filament 16 to an energy source (not shown). Because the energy output of a filament 16 generally varies approximately with the operating voltage, close voltage control is essential. For this reason, most lamps 14 are attached through the wires or leads 22 to a constant-voltage transformer or electronic voltage regulator.

The basic illumination source depicted in FIG. 2 further includes an elliptical reflector 12 which focuses emitted light from bulb 14 to a reflector focus 26. Representative rays 24 are depicted to show the function of the reflector 12. The relationship between the radiant source emitter 14 and the elliptical reflector 12 was used in the subsequently disclosed experiments.

Referring now to FIG. 3, a diagramed view of a system 10 for measuring the concentration of an analyte within biological tissue is depicted. The system 10 depicted is simplified by illustrating certain specific elements within a far more elaborate spectroscopic system. The elements depicted in FIG. 3, however, are common to spectroscopic systems, and therefore, require some identification.

An elliptical reflector 12 known in the art is shown. At the center of the elliptical reflector 12 is radiation source lamp 14. The radiation source lamp 14 is depicted as having a filament 16, a glass envelope 18 with nipple 20 housing the filament 16, and a pair of leads 22 extending from the end of the lamp. Surrounding a portion of the lamp 14 is the body of the reflector 12. The elliptical reflector 12 functions to concentrate emitted radiation rays 24 (shown as a ray trace) from the radiation source lamp 14 onto the reflector's focal point 26. In order to maximize reflectance, the elliptical reflector 12 is generally made from a highly polished metal. Although FIG. 3 specifically illustrates an elliptical reflector, other shapes suitable for focusing radiant energy are also within the scope of the invention.

FIG. 3 depicts two fiber optic bundles, an illumination fiber bundle 30 and a collection fiber bundle 32. Fiber optic bundles 30 and 32 are extremely versatile because they are capable of channeling harnessed radiation between elements without noticeable reduction in the intensity of that harnessed radiation.

At the reflector's focal point 26 is an opening to the illumination fiber bundle 30. The illumination fiber bundle 30 collects the radiation emitted 24 by the lamp 14 and channels the radiation through the bundle system. At the output end of the illumination fiber bundle 30 is another opening that then directs the harnessed radiation onto a sample 40, such as human tissue on a person's forearm. The second fiber optic bundle, the collection fiber bundle 32, is positioned proximate to the sample 40 to again collect radiation, however, here the radiation is diffusely reflected from the sample 40.

Diffusely reflected radiation is that radiation reflected from within the sample 40. Diffusely reflected radiation does not generally follow a uniform pattern. Ray tracing of the diffusely reflected radiation within the sample 40 as shown in FIG. 3 illustrates possible pathways of radiation entering, and subsequently reflecting out of, the sample 40.

The collection fiber bundle 32 then channels the diffusely reflected radiation from the sample 40 to the FTIR spectrometer subsystem 400 (see FIG. 1). In FIG. 3, the FTIR spectrometer subsystem is shown simply as spectrophotometer 44 and is where the radiation is detected by converting the recaptured radiant energy into a measurable signal. In a preferred embodiment of the invention, an FTIR spectrophotometer is utilized to analyze the diffusely reflected radiant energy emitted by the sample 40. The output optical signal from the FTIR is focused on a photodetector which converts the optical signal to an electrical signal that is then transferred to the data acquisition subsystem 500 (see FIG. 1) which includes a signal processor. Processing of the signal is generally accomplished using a computer or other data processing means 46 designed for such processing. The outcome of the processing is then transcribed to a readout, allowing practitioners to study the results of the analysis.

As described in detail above, in spectrophotometer instruments where shot noise predominates the system, as is in the system depicted in FIG. 3, the signal-to-noise ratio (SNR) for the system is directly proportional to the square root of the flux ($\Phi$) on the photodetector. The SNR for the system, however, can be improved by maximizing the amount of radiation incident on the detector. Increasing the flux on the detector generally necessitates increasing the incidance, and thus, may cause thermal damage on the sampled biological tissue 40. To illustrate this tissue-heating problem, experiments were conducted utilizing the system illustrated in FIG. 3. For the experiment, the sample 40 used was the forearm of a living human subject and the analyte to be measured was glucose.

The radiation source lamp 14 was connected to a variable current source that permitted the lamp 14 to increase output up to a maximum of 40 watts. The output of the lamp would then be incrementally increased until the SNR was high enough to acquire accurate glucose measurements. As the lamp power was increased during the subsequent experimental trials, most of the subjects reported discomfort prior to reaching an acceptable SNR. The discomfort experienced by the subjects was due to a localized heating of their forearm by the illuminating radiation.

To further analyze the above-described phenomenon, a ray trace program was utilized to compare and contrast various illumination systems for spatial and angular homogeneity. TracePro V2.1, a commercially available non-sequential ray trace program, was used to generate realistic models of the radiation distributions from various illumination system configurations. The output from such modeling is depicted in FIGS. 4a–c, 5a–c, 14a–c and 15a–c. In order to understand the output of the modeled illumination, Table 1 correlates the specific radiometric terms to their corresponding symbols, definitions, and units.

TABLE 1

Definition of Radiometric Quantities

| Name | Symbol | Definition | Units |
|---|---|---|---|
| Energy | Q | — | Joules, J |
| Flux | $\Phi$ | $\dfrac{\partial Q}{\partial t}$ | Watts, W |
| Exitance | M | $\dfrac{\partial \Phi}{\partial A_s}$ | W/m² |
| Incidance | E | $\dfrac{\partial \Phi}{\partial A_r}$ | W/m² |

TABLE 1-continued

Definition of Radiometric Quantities

| Name | Symbol | Definition | Units |
|---|---|---|---|
| Radiance | L | $\dfrac{\partial \Phi}{\partial (A_s \cdot \cos\theta) \cdot \partial \Omega}$ | W/m²/sr |

With respect to Table 1, $\delta A_r$ and $\delta A_s$ refer to differential elements of area on the receiver and source, respectively. Additionally, $\theta$ refers to the angle between the line of sight from the observer to the source and the direction of the radiation 24. The associated spectral quantities are defined by differentiating the above general radiometric quantities with respect to wavelength, as depicted below:

$$M_\lambda \equiv \frac{\partial M}{\partial \lambda}, E_\lambda \equiv \frac{\partial E}{\partial \lambda}, \text{ and } L_\lambda \equiv \frac{\partial L}{\partial \lambda}$$

Figure 4A:
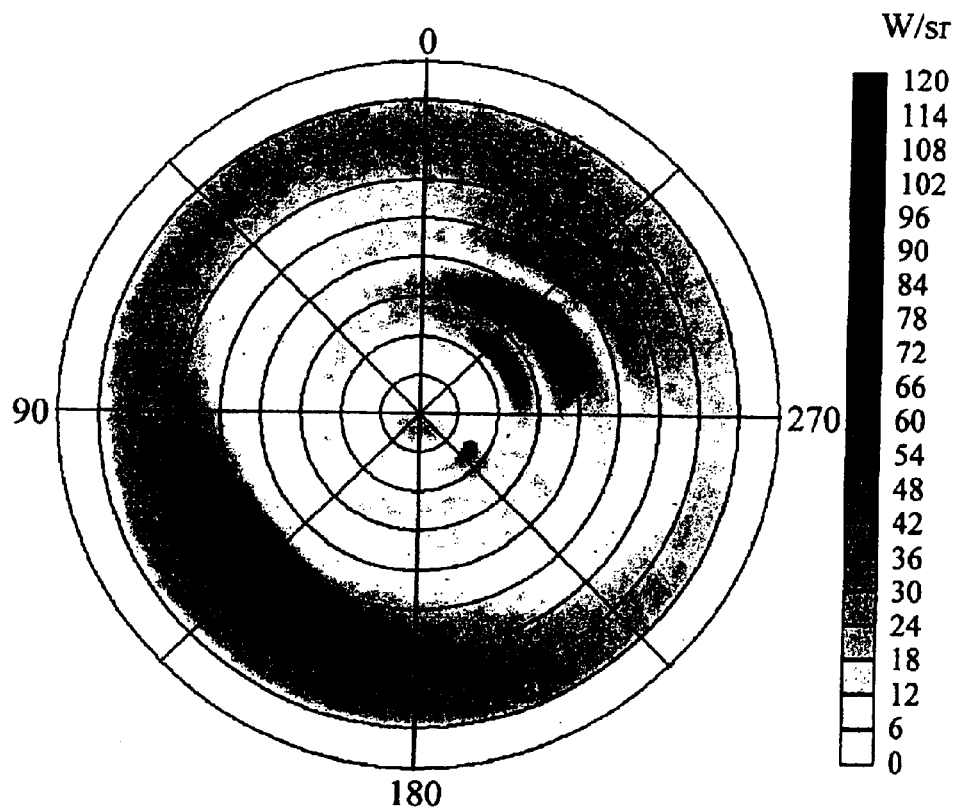
FIG. 4a is an incidance plot using a ray trace program simulating the spatial distribution of emitted radiation from an infrared spectrophotometer known in the art.
Figure 4B:
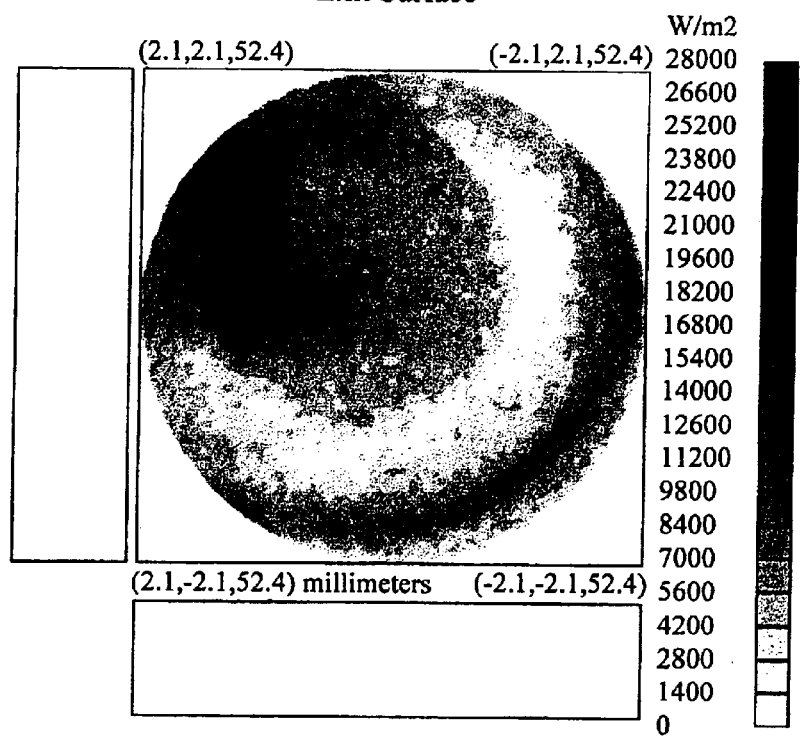

FIGS. 4a–c are plots of the incidance of emitted radiation 24 from the elliptical reflector 12 in FIG. 2. These plots have been generated using TracePro V2.1, a ray trace program simulating the spatial distribution of emitted radiation from the radiation source lamp 14. More specifically, the plots of incidance are representative of the spatial distribution of emitted radiation at the focus of the elliptical reflector 26 diagramed in FIG. 2.

FIG. 4a shows a plot of incidance of emitted radiation 24 from a radiation source lamp 14. The resulting incidance plot is characterized by a substantial degree of spatial inhomogeneity. Spatial distribution of emitted radiation in particular areas of the plot is demonstrated to vary substantially throughout the incidance plot. In certain areas within the plot, the spatial distribution is greater than other areas within the same plot. The converse is also true. The spatial distribution of the emitted radiation is also illustrated to follow certain arc-like bands of greater or lesser incidance throughout the plot.

FIG. 4b shows a plot of incidance of the same radiation source lamp of FIG. 4a, but after a 90-degree rotation of the filament producing the incidance plot. Comparisons of the plots of FIGS. 4a and 4b show that areas of greater incidance in FIG. 4a are now areas of lesser incidance in FIG. 4b, and the inverse. FIG. 4c further depicts this spatial distribution disparity by showing the changes in spatial distribution when the filament 16 of the same radiation source lamp 14 of FIG. 4a undergoes a vertical translation of one millimeter. Again, the spatial distributions in FIG. 4c after the one-millimeter translation provide areas of greater incidance where there were originally none in FIG. 4a. These plots document that the spatial distribution of light at the focus of the standard light source is highly unstable with modest translations and/or rotations of the filament.

Similar to FIGS. 4(a–c), FIGS. 5(a–c) depict plots of the intensity of emitted radiation from the elliptical reflector in FIG. 2. These plots have also been generated using TracePro V2.1 to simulate the angular distribution of emitted radiation 24 from a radiation source emitter 14 known in the art. More specifically, the plots are representative of the angular distribution of emitted radiation at the focus of the elliptical reflector 26 diagramed in FIG. 2, i.e., the direction of the light rays at the focus of the elliptical reflector.

Figure 5A:
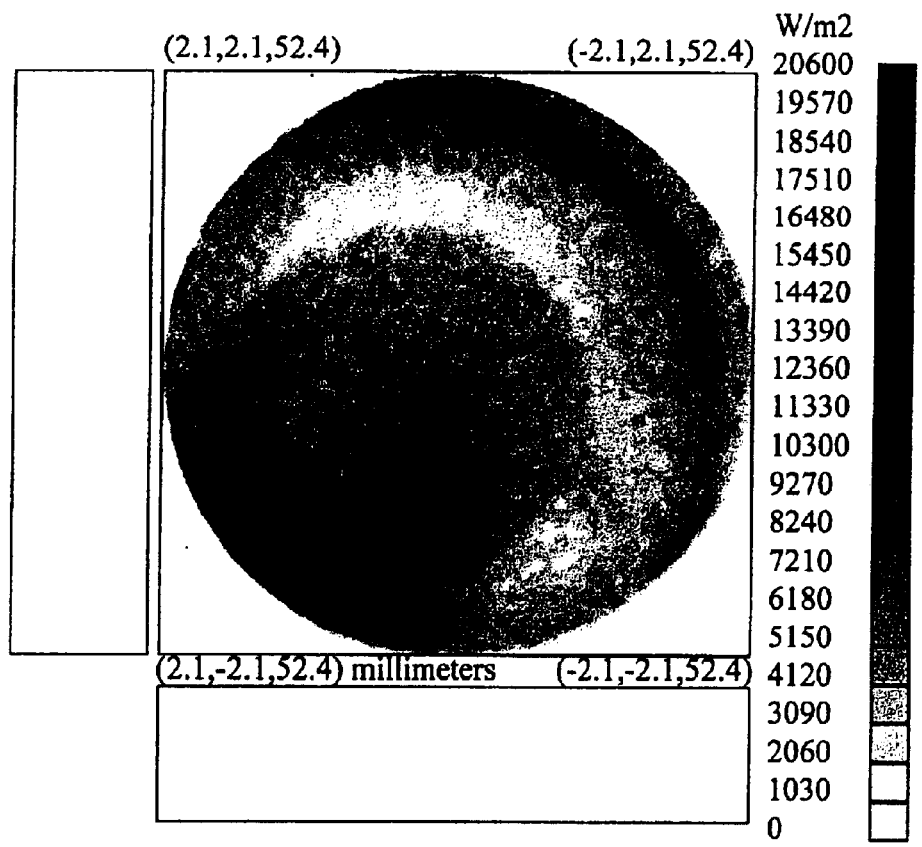
FIG. 5a is an intensity plot using a ray trace program simulating the angular distribution of emitted radiation from an infrared spectrophotometer known in the art.

FIG. 5a shows a plot of intensity of emitted radiation from a radiation source lamp 14. The resulting intensity plot from the standard radiation source is characterized by a substantial degree of angular inhomogeneity. Angular distributions in particular areas of the plot also vary dramatically within the same plot. For example, FIG. 5a illustrates a "hole" in the center of the intensity plot. The lack of irradiation intensity in this particular area is a result of a shadowing effect by the envelope nipple 20 on the end of a radiation source lamp 14.

Figure 5B:
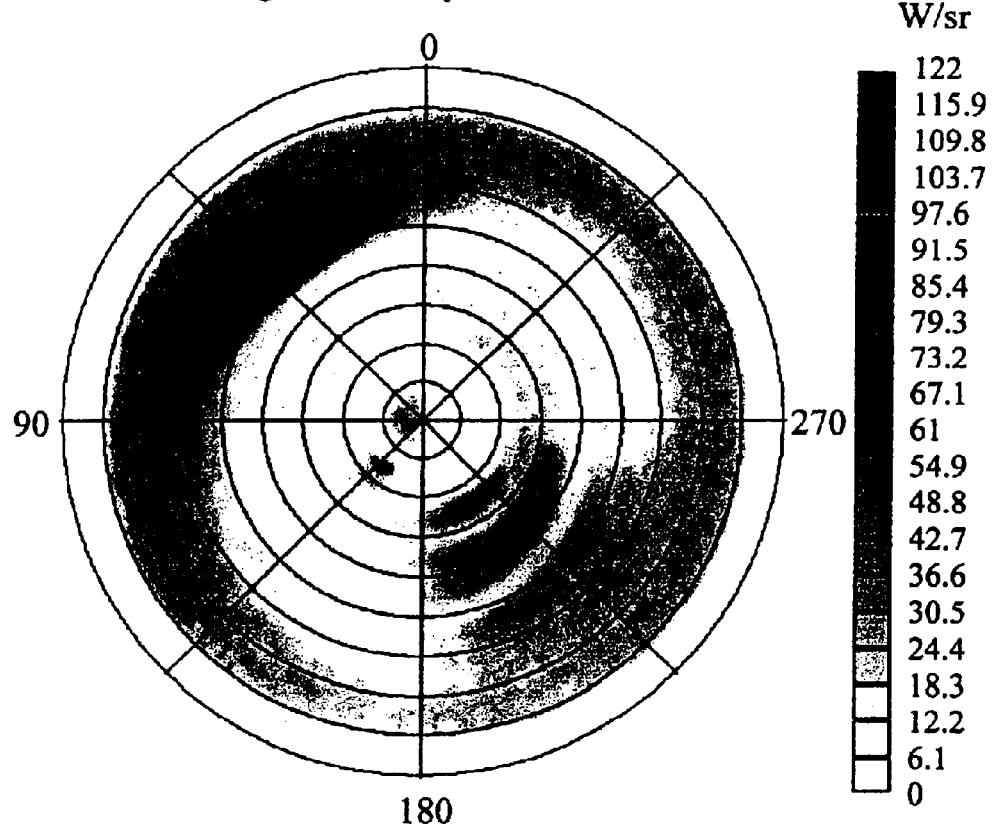
Figure 5C:
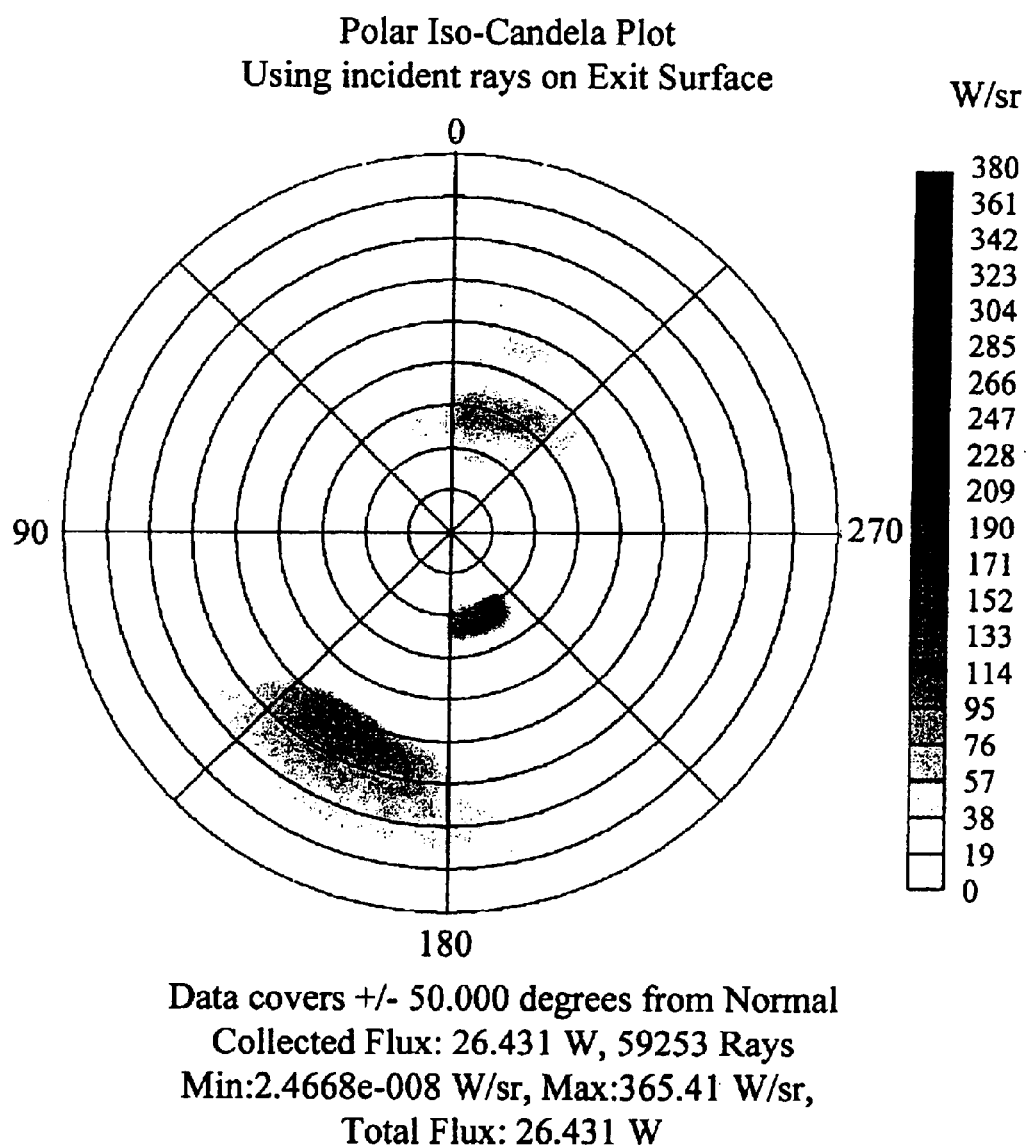

Rotating the filament 16 of FIG. 5a produces an intensity plot illustrated by FIG. 5b. Because the filament 16 was rotated, the hole 60 in the center of the plot remains centered within the plot after the 90-degree rotation. Translation of the filament 16 of FIG. 5a by one millimeter, however, greatly diminishes the angular distribution within the spectroscopic system, as depicted in FIG. 5c. Angular distributions are sporadic, and often completely shadowed by the modest translation of the radiation source lamp 14.

The ray trace plots of FIGS. 4(a–c) and FIGS. 5(a–c) illustrate that the spatial and angular distribution of light at the focus 26 of a standard radiation source 14 is highly unstable with respect to modest translations and/or rotations of its filament 16. Areas of higher incidence and intensity may form "hot spots" during illumination. In an attempt to maximize the signal-to-noise ratio, the radiation source 14 could be increased to the thermal and/or comfort limits established by the patient However, if there are "hot spots" across the tissue, these areas may require a lower overall radiation output and corresponding result of lower SNR. Thus, uniform intensity illumination is desired when attempting to maximize the SNR for glucose measurements.

The above plots clearly illustrate angular and spatial variances associated with the illumination system. These variances translate into spectroscopic variances that adversely influence the achievement of high levels of accuracy in measuring analyte concentrations. Inhomogeneous spatial and angular distributions of emitted radiation 24 impede a practitioner from constructing chemometric models that are sensitive to the differences between interferents and the desired analyte. Modest and unaccounted for translations and/or rotations of the emitter 14, such as those that might result from loose mechanical tolerances or vibration, have been found to significantly alter these relied-upon chemometric models. An additional experiment was conducted to illustrate the effect of interferent variations on a calibrated chemometric model.

Figure 6:
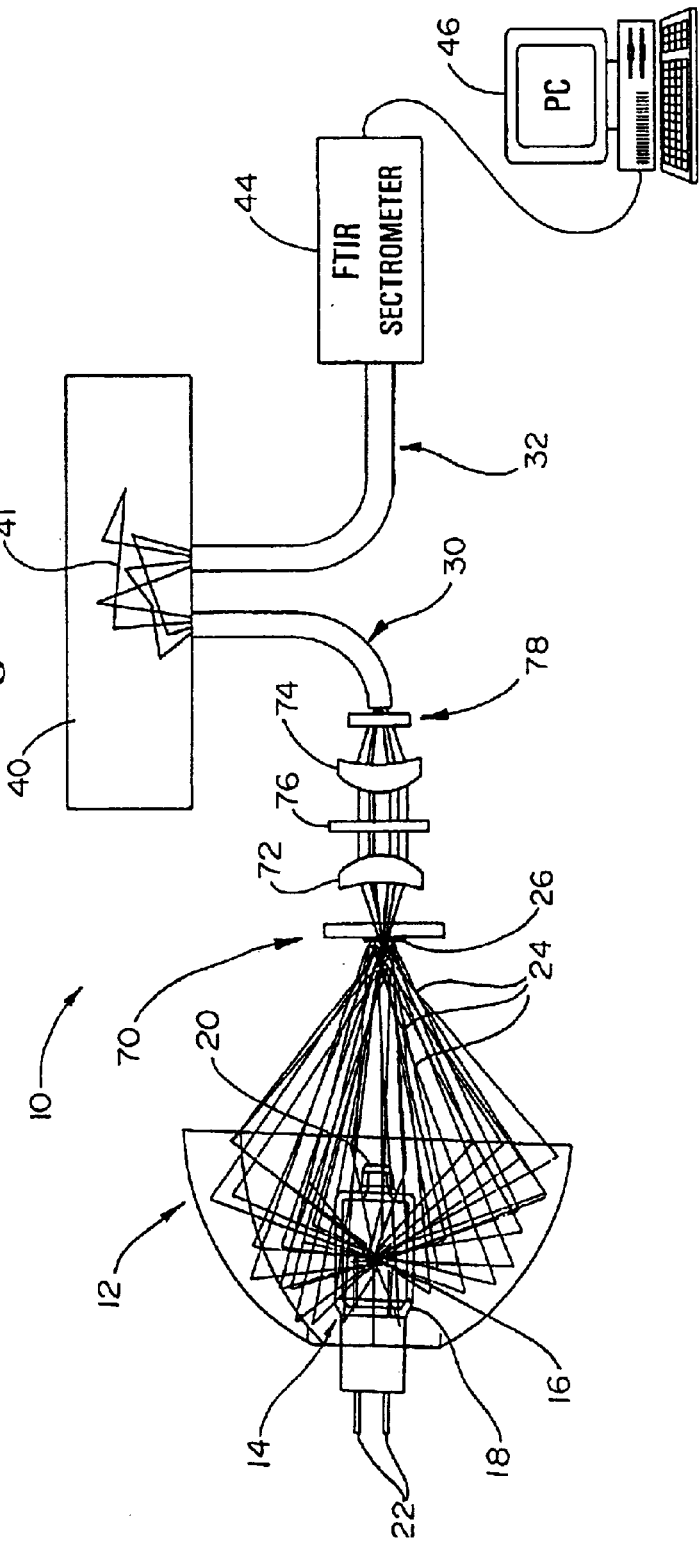
FIG. 6 is a diagramed view of a system for constructing a chemometric model for measuring glucose concentration in the forearm's of various subjects.

FIG. 6 shows a diagramed view of the system used for constructing a chemometric model for measuring glucose concentration in the forearm's of various subjects. The components within this instrument system closely resemble those in FIG. 3 and like elements are numbered the same. The additions utilized should not be construed as an exhaustive list for constructing an accurate chemometric model for glucose measurement. Identification of these additions is merely for illustrative purposes only, as one of skill in the art may readily identify numerous combinations of instrument components that could achieve a chemometric model for the desired analyte.

The first of the additions shown in FIG. 6 is a five (5) millimeter aperture 70 positioned at the focal point of the elliptical reflector 26. This aperture 70 limits the amount of emitted radiation 24 permitted to pass through the system 10 for analysis. Once the radiation clears the aperture 70, a silicon lens 72 redirects the radiation through a cyan filter 76, which in turn, sends the radiation through a second silicon lens 74. Radiation transmitted through this series of lenses is then filtered to absorb radiation at wavelengths at or greater than 2.7 micron by passing through filter/diffuser 78. In a preferred embodiment, a WG295 filter/diffuser is utilized to absorb the wavelengths at or greater than 2.7 micron. The radiation is then illuminated upon a sample 40, collected and analyzed as described in relation to FIG. 3.

Using the above-described system, numerous calibration spectra spanning a wavelength range of approximately 1.25 $\mu$m to 2.5 $\mu$m were used to construct a chemometric model for measuring glucose concentrations within forearms' of subjects. The calibration set spanned several different lamps, many human subjects, a wide range of glucose values, and a variety of operating temperatures and relative humidities.

During the "prediction" phase of the experiment, eleven human subjects were measured by the spectrometer system four times each day. Additionally, the radiation source lamp 14 for the system was changed every two days. As a note, the human subjects and lamps used in this prediction phase of the experiment were not the same as those used during the calibration phase. The results of this experiment are shown in FIG. 7, where the errors are sorted by day.

Figure 7:
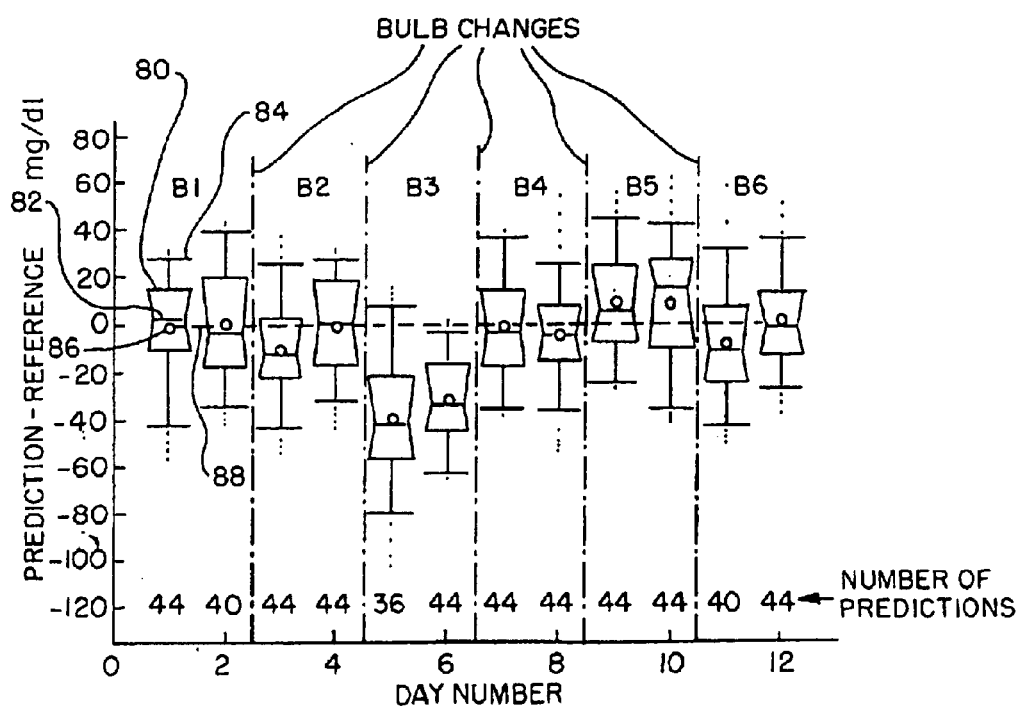
FIG. 7 is a box and whisker plot of prediction error versus day across five lamp changes using the system illustrated in FIG. 6.

FIG. 7 shows a "box and whisker" plot. In this type of plot, the median prediction error for each day is plotted as a horizontal line 82 in the middle of a box 80, which encompasses the middle half of the data, and "whiskers" 84 are plotted at the 5th and 95th percentiles; a "dot" 86 represents the mean prediction error for the day; the horizontal dashed line 88 shows where the data are centered when the prediction error bias is zero; and the numbers shown under at the bottom of the graph indicate the number of predictions associated with that whisker and taken on each study day.

FIG. 7 specifically shows a box and whisker plot of prediction error versus day across five lamp changes, six lamps in total, over twelve days. During the first four days of the experiment, regarding lamps 1 and 2, the absolute prediction error bias was less than 20 mg/dl. After the second lamp change, however, (on days 5 and 6 of the experiment) the absolute bias increased dramatically. Replacing the third lamp with a fourth (on day 7 of the experiment) reduced the bias to well under 20 mg/dl.

These results suggest that the chemometric model was sufficiently "robust" as to permit accurate determination of the glucose levels for the subjects for most of the lamps, even though the lamps used during the prediction phase were not the same as those used during calibration. With regard to the third lamp, however, the chemometric model failed to produce accurate predictions. This failure suggests that the emission characteristics of this lamp were substantially out of the calibration range used to build this experimental chemometric model.

Figure 8:
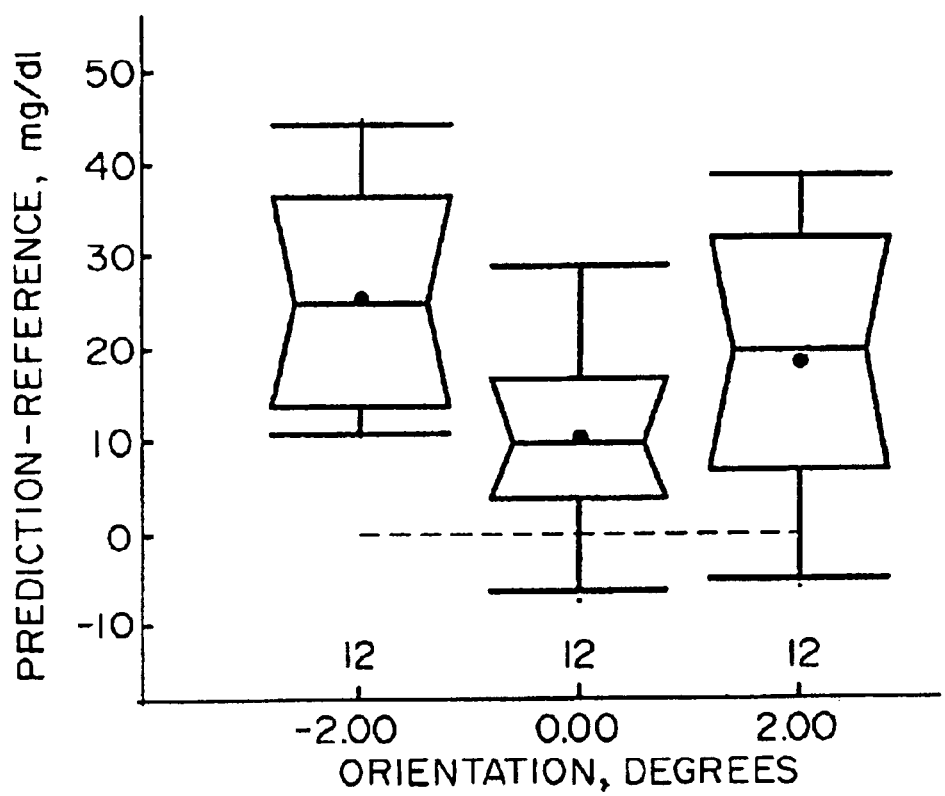
FIG. 8 is a box and whisker plot of in-vivo prediction errors versus orientation for a lamp within a system illustrated in FIG. 6.

To help isolate the emitter variation within the illumination subsystem, as the source of the prediction errors described above, another experiment was conducted using the same apparatus, and similar methods as described in the previous experiment. In this subsequent experiment, however, spectra were collected from three different subjects all on the same day, using the same lamp throughout the prediction period. The lamp was installed in the apparatus at some arbitrary azimuthal orientation, $\theta_0$, and spectra of the subject's forearms were taken at $\theta_0$, as well as at +/−2 degrees. The resulting prediction errors are plotted in FIG. 8 for the three lamp orientation states. These results indicate that changes in the emitter characteristics, which are the result of small rotations of the lamp, can cause prediction errors that are almost as large as those caused by complete replacement of one lamp with another.

A third experiment was then conducted to evaluate the effects of lamp changes on prediction error. The system utilized is depicted in FIG. 9, with like elements numbered the same as in FIG. 3 and FIG. 6. In this experiment, the sample source of living tissue 40 (a subject's forearm) was replaced with a "tissue phantom" 43. A tissue phantom is solid, liquid, gel, jelly or combination thereof that approximates the absorbance and water pathlength distribution of living tissue without necessarily replicating the compositional and structural properties of living tissue. Tissue phantoms 43 consist of a scattering solution made of microscopic polystyrene beads suspended in water at varying concentrations. In this experiment, the concentration range for the polystyrene beads was between 5000–8000 mg/dl. Tissue phantoms 43 within these ranges are representative substitutes for living tissue because their optical scattering and absorption properties are similar to those of biological tissue. Additionally, the use of tissue phantoms of known concentrations eliminates the confounding effects often observed from physiological changes in living tissue. FIG. 9 diagrams the replacement of a subject's forearm 40 with a tissue phantom 41. Further, the cyan filter 76 is located after the output fiber optic 32. In all other respects, the apparatus diagramed in FIG. 9 is consistent with those discussed in detail with respect to FIG. 3 and FIG. 6.

A set of 98 different tissue phantoms composed of 5 different analytes at different concentrations were optically sampled. In order to assess the ability of this system in FIG. 9 to predict glucose concentrations in the absence of lamp changes, a "cross-validation" analysis was performed. To accomplish this cross-validation analysis, a series of baseline measurements were performed wherein spectra of all ninety-eight solutions were taken using a single lamp with the apparatus depicted in FIG. 9. This data was artificially subdivided into four sets. Using three of these sets, a chemometric model was constructed to predict glucose values for the remaining set. The analysis procedure was again repeated, rotating the data sets used for calibration and prediction, until all four sets had been used for prediction. The results of the cross-validation are shown in FIG. 10a. The prediction errors biases shown in FIG. 10a are clustered near 0 mg/dl. Such clustering suggests that in the absence of a lamp change, this apparatus is capable of making satisfactory measurements of glucose concentration with these samples.

Another cross-validation analysis was then performed. In this cross-validation analysis, the ninety-eight solutions discussed above were grouped into four subsets, and a different lamp was assigned for use as the illumination source for each subset. In this analysis, data from three of the lamps was used to build a chemometric model to predict glucose in data from the fourth lamp. This chemometric modeling procedure was repeated until each of the four data sets was used for prediction. The prediction results for the four data sets are presented in FIG. 10b. A comparison between the four data sets shows a very large lamp-to-lamp prediction bias. These results are again consistent with the findings presented in FIG. 7 (the replacement of individual lamps) and FIG. 8 (the modest rotation and/or translation of a single lamp by +/−2 degrees), thus further illustrating the deleterious effects of interferents, such as emitter variations, on the development of accurate chemometric models for a preferred illumination subsystem 100 of the present invention.

Figure 11:
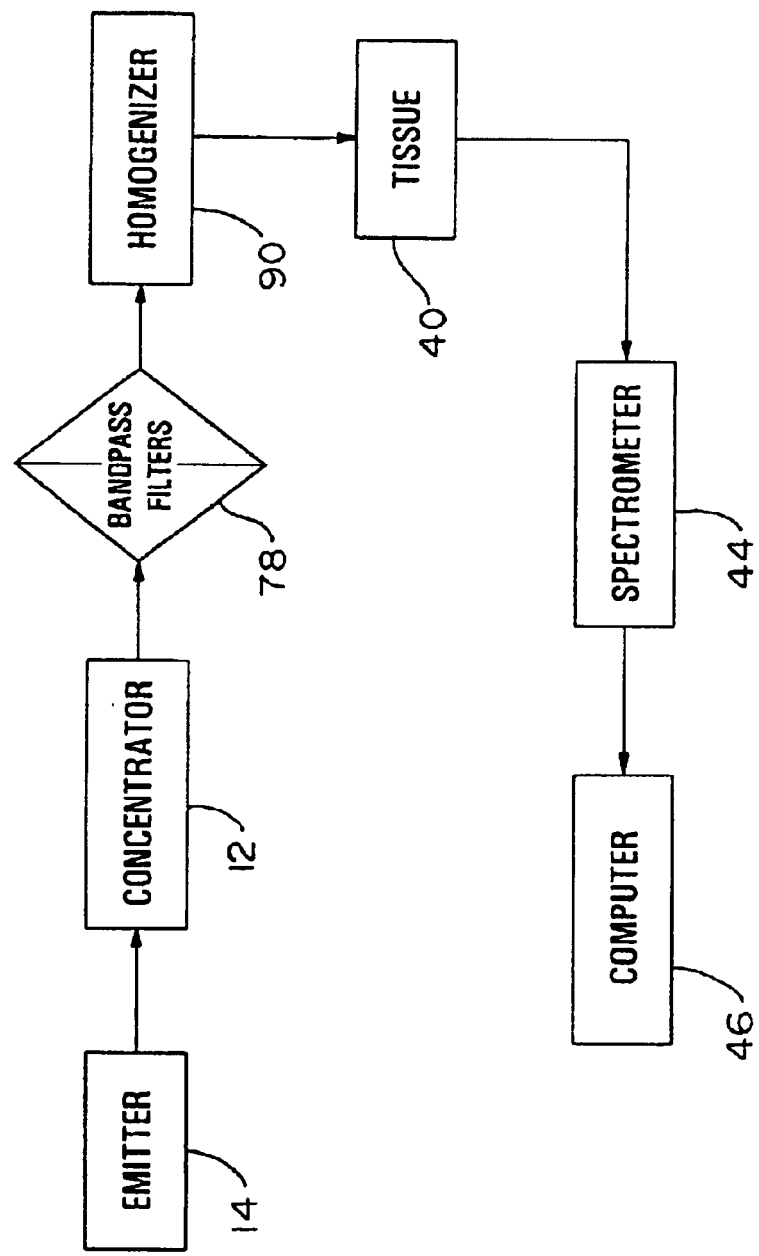
FIG. 11 is a diagramed view of a system of the present invention using a means for spatially and angularly homogenizing emitted radiation.

The illumination subsystem 100 of the present invention overcomes the above-identified problems. FIG. 11 schematically depicts a simplified system incorporating means for optimizing the illumination subsystem 100 to help achieve clinically relevant analytical results. In most respects, the apparatus diagramed in FIG. 11 is consistent with those features discussed in detail with respect to FIG. 6, with the clear identification of a radiation homogenizer 90. In a preferred embodiment, the homogenizer 90 is positioned between the filter 78 and the sample 40, as depicted in FIG. 11. At this location, entering nearly monochromatic radiation is spatially and angularly homogenized prior to its distribution upon the sample 40.

The placement of the homogenizer 90 at the above-described location is not to be construed as restricting the scope of the invention. The system depicted in FIG. 11 is significantly simplified for illustrative purposes. Only certain specific elements within a far more elaborate spectroscopic system are diagramed. All the elements depicted in FIG. 11, however, are common to preferred spectroscopic systems of the present invention. The elements diagramed, therefore, are to aid in identification of various aspects of the overall spectroscopic system. Thus, it should be understood that the present invention encompasses embodiments wherein various components of a spectroscopic system may be assembled in a relative order other than the one explicitly diagramed in FIGS. 11 and 16. However, the homogenizer 90 is placed at a point between the emitter 14 and the tissue or sample 40, although other elements may be included between the homogenizer 90 and emitter 14 or between the homogenizer 90 and tissue or sample 40. This can also include the spectrometer 44, which in certain embodiments can be positioned between the emitter 14 and tissue 40.

Figure 12B:
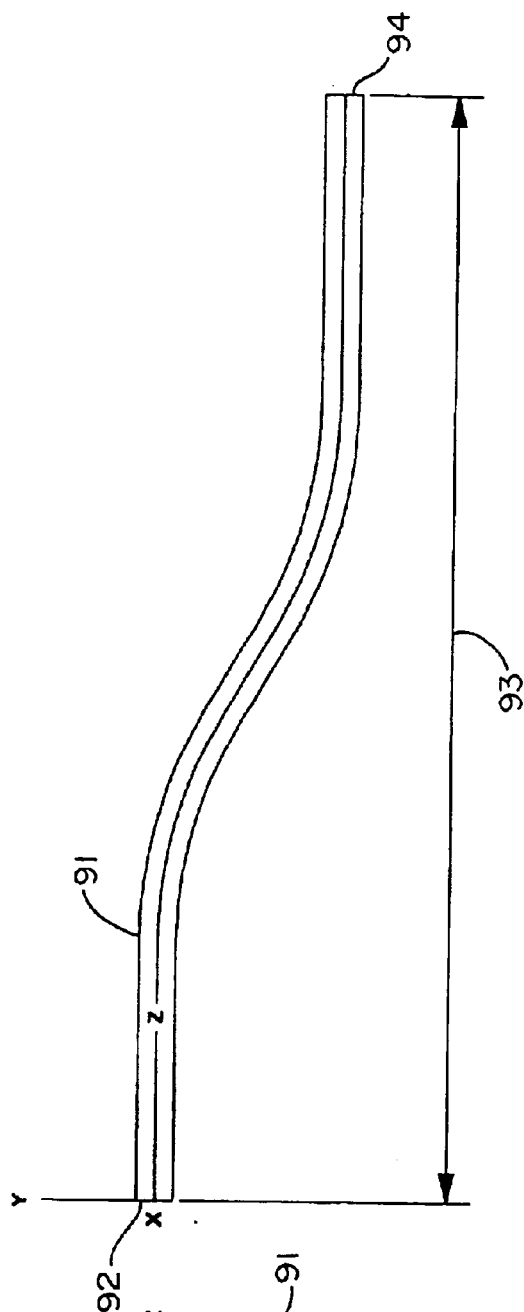
FIG. 12a and FIG. 12b are depicted as a perspective and a plan view of a light pipe of the present invention.
Figure 12A:
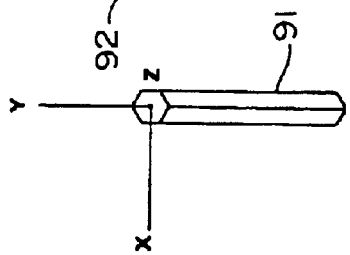

In a preferred embodiment, the radiation homogenizer 90 is a light pipe. FIGS. 12a and 12b show a perspective end view and a detail plan view of a light pipe 91 of the present invention. Light pipe 91 is generally fabricated from a metallic, glass (amorphous), crystalline, polymeric, or other similar material, or any combination thereof. Physically, the light pipe comprises a proximal end 92, a distal end 94, and a length 96 therebetween. The length of a light pipe 91, for this application, is measured by drawing a straight line from the proximal end 92 to the distal end 94 of the light pipe. Thus, the same segment of light pipe 91 may have varying lengths depending upon the shape the segment forms. The length of the segment readily varies with the light pipe's intended application.

In a preferred embodiment as illustrated in FIGS. 12a and 12b, the segment forms an S-shaped light pipe. The S-shaped bend in the light pipe provides angular homogenization of the light as it passes through the light pipe. This conclusion is documented by the experiment and discussion associated with FIGS. 14a–c and 15a–c below. It is, however, recognized that angular homogenization can be achieved in other ways. A plurality of bends or a non-S-shaped bend could be used. Further, a straight light pipe could be used provided the interior surface of the light pipe included a diffusely reflective coating over at least a portion of the length. The coating provides angular homogenization as the light travels through the pipe. Alternatively, the interior surface of the light pipe can be modified to include dimples or "microstructures" such as micro-optical diffusers or lenses to accomplish angular homogenization. Finally, a ground glass diffuser could be used to provide some angular homogenization.

The cross-section of the light pipe 91 may also form various shapes. In particular, the cross-section of the light pipe 91 is preferably polygonal in shape to provide spatial homogenization. Polygonal cross-sections include all polygonal forms having three to many sides. Certain polygonal cross-sections are proven to improve spatial homogenization of channeled radiation. For example, a light pipe possessing a hexagonal cross-section the entire length thereof provided improved spatial homogenization when compared to a light pipe with a cylindrical cross-section of the same length.

Additionally, cross-sections throughout the length of the light pipe may vary. As such, the shape and diameter of any cross-section at one point along the length of the light pipe may vary with a second cross-section taken at a second point along the same segment of pipe.

In certain embodiments, the light pipe is of a hollow construction between the two ends. In these embodiments, at least one lumen may run the length of the light pipe. The lumens of hollow light pipes generally possess a reflective characteristic. This reflective characteristic aids in channeling radiation through the length of the light pipe so that the radiation may be emitted at the pipe's distal end. The inner diameter of the lumen may further possess either a smooth, a diffuse or a textured surface. The surface characteristics of the reflective lumen aid in spatially and angularly homogenizing radiation as it passes through the length of the light pipe.

In additional embodiments, the light pipe is of solid construction. The solid core could be cover-plated, coated or clad. Again, a solid construction light pipe generally provides for internal reflection. This internal reflection allows radiation entering the proximal end of the solid light pipe to be channeled through the length of the pipe. The channeled radiation may then be emitted out of the distal end of the pipe without significant loss of radiation intensity. An illustration of internal reflection and the resulting channeling is shown in FIG. 13.

Figure 13:
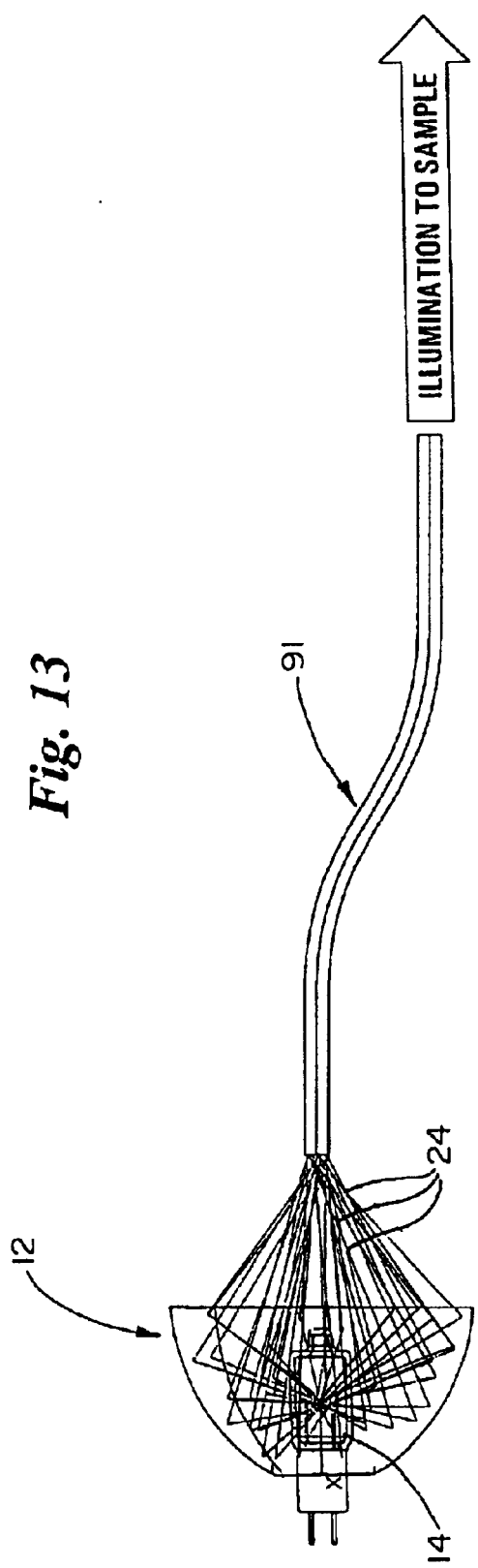
FIG. 13 is a plan view of a ray trace showing radiation focused by an elliptical reflector into and through a light pipe of the present invention.

FIG. 13 depicts a plan view of a ray trace showing radiation 24 from a light source 14 (40 watt tungsten-halogen bulb) focused by an elliptical reflector 12 into, and through, a light pipe 91 of the present invention. In particular, FIG. 13 illustrates how emitted radiation from a radiation source lamp is focused upon the proximal end of the light pipe of the present invention. The focused radiation is internally reflected throughout the length of the light pipe. As the radiation is reflected, specific structural characteristics of the light pipe (here an S-shaped segment of hexagonal cross-sectioned pipe) angularly and spatially homogenizes the resulting radiation emitted at the pipe's distal end.

FIGS. 14(a–c) are plots of the incidance of emitted radiation from the elliptical reflector and light pipe depicted in FIG. 13. These plots have again been generated using TracePro V2.1, a ray trace program simulating the spatial distribution of emitted radiation from the radiation source emitter. More specifically, the plots of incidance are representative of the spatial distribution of emitted radiation at the distal end of the light pipe diagramed in FIG. 13.

Figure 14A:
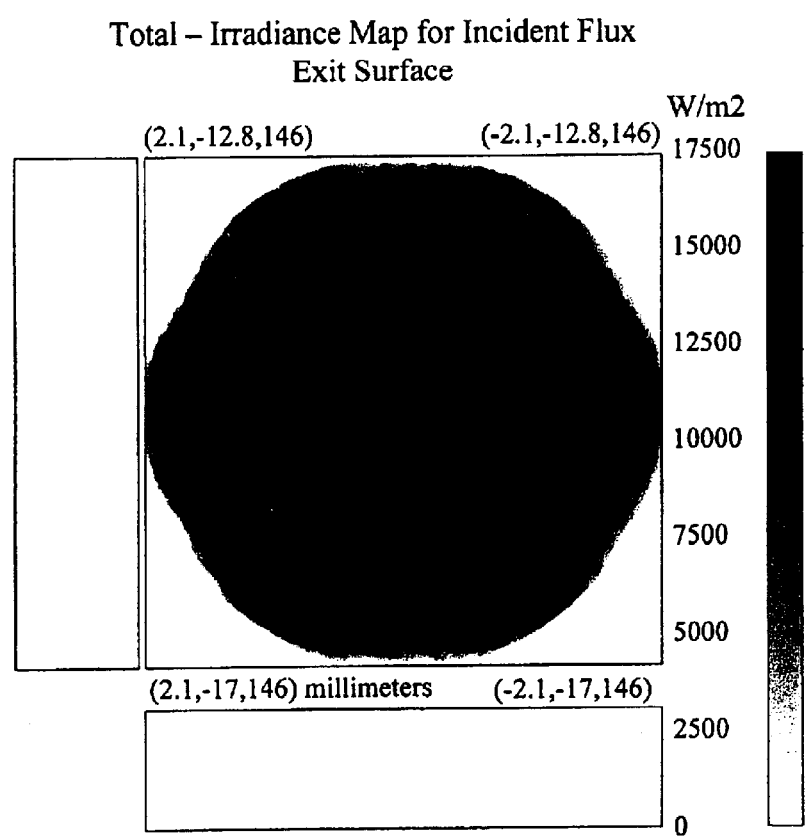
FIG. 14a is an incidance plot using a ray trace program simulating the spatial distribution of emitted radiation from an infrared spectrophotometer using a light pipe of the present invention.

FIG. 14a shows a plot of incidence of emitted radiation from the radiation source lamp coupled to the light pipe of the present invention. The resulting incidance plot is characterized by a substantial degree of spatial homogeneity. Spatial distribution of emitted radiation throughout the incidance plot varies slightly. A comparison of FIG. 14a with that of FIG. 4a illustrates the substantial improvement in spatial distribution throughout the incidance plot when using a light pipe of the present invention.

Figure 14B:
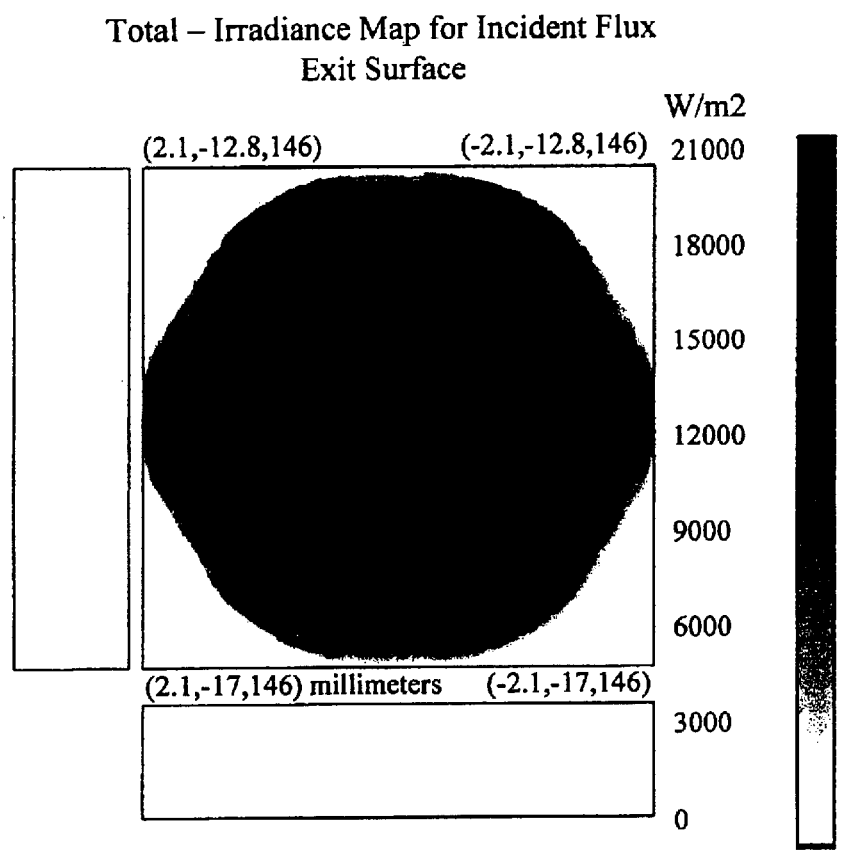

FIG. 14b shows a plot of incidence of the same radiation source lamp coupled to the light pipe of the present invention as depicted in FIG. 14a, but after a 90-degree rotation of the filament producing the incidance plot. Again, the resulting incidance plot is characterized by a substantial degree of spatial homogeneity. In fact, there exist few detectable difference in spatial distribution after the resulting 90-degree rotation as with the spatial distribution prior to the rotation.

Figure 14C:
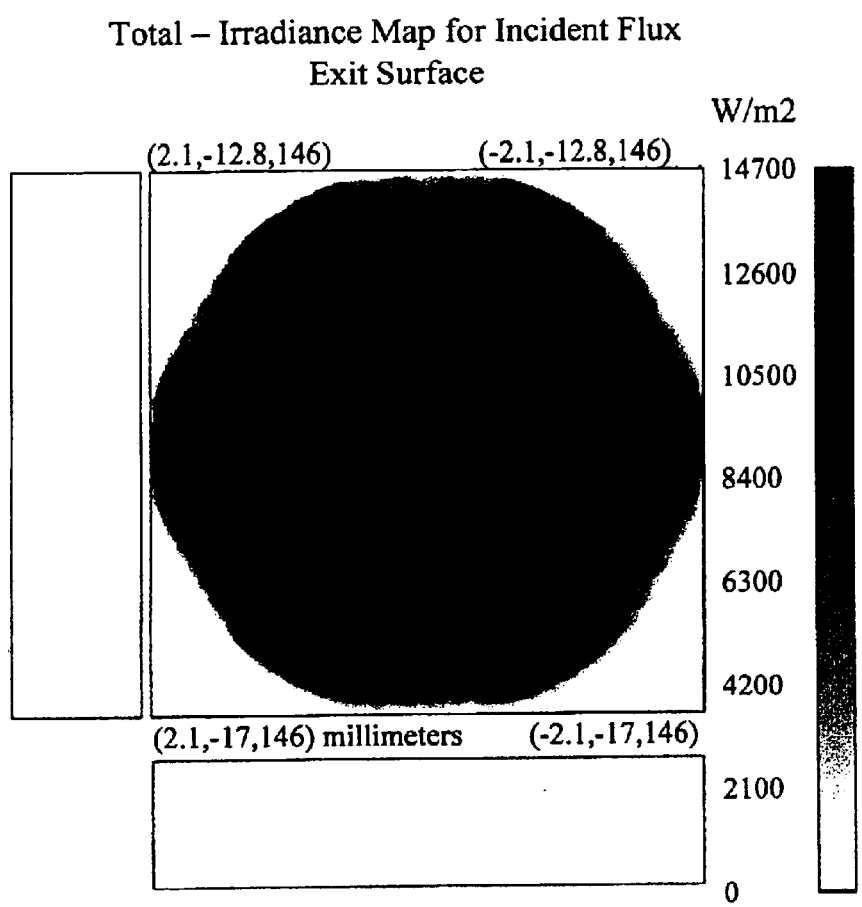

FIG. 14c further depicts the spatial homogeneous distribution of emitted radiation using a light pipe of the present invention. Again, the spatial distribution in FIG. 14c, after a one-millimeter translation, is very similar to those spatial distributions in FIGS. 14(a–b).

Similar to FIGS. 14(a–c), FIGS. 15(a–c) show plots of the intensity of emitted radiation from the elliptical reflector and light pipe depicted in FIG. 13. These plots have also been generated using TracePro V2.1 to simulate the angular distribution of emitted radiation from a radiation source emitter known in the art. More specifically, the plots of intensity are representative of the angular distribution of emitted radiation at the distal end of the light pipe diagramed in FIG. 13.

Figure 15A:
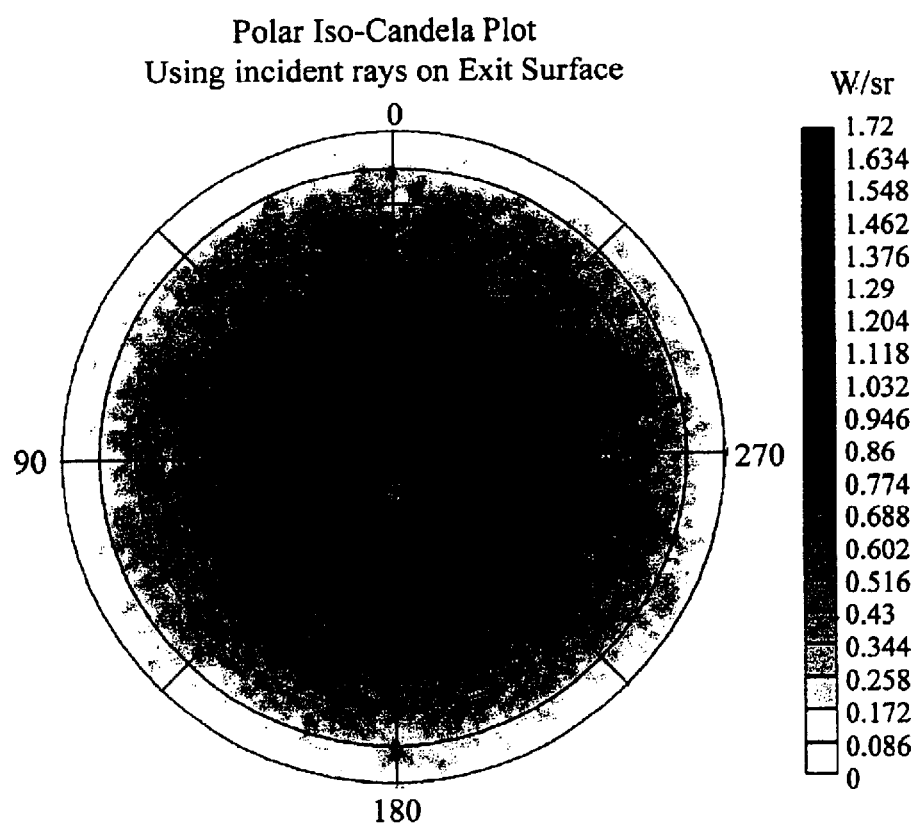
FIG. 15a is an intensity plot using a ray trace program simulating the angular distribution of emitted radiation from an infrared spectrophotometer using a light pipe of the present invention.

FIG. 15a shows a plot of intensity of emitted radiation from the radiation source lamp coupled to the light pipe of the present invention. The resulting intensity plot from the standard radiation source is characterized by a substantial degree of angular homogeneity. Angular distributions throughout the plot vary slightly. A comparison of FIG. 15a with that of FIG. 5a illustrates the substantial improvement in angular distribution throughout the intensity plot when using a light pipe of the present invention. For example, the "hole" in the center of the intensity plot caused by the glass nipple on the end of the radiation source lamp is no longer present and is now replaced with homogenized angular radiation.

Figure 15B:
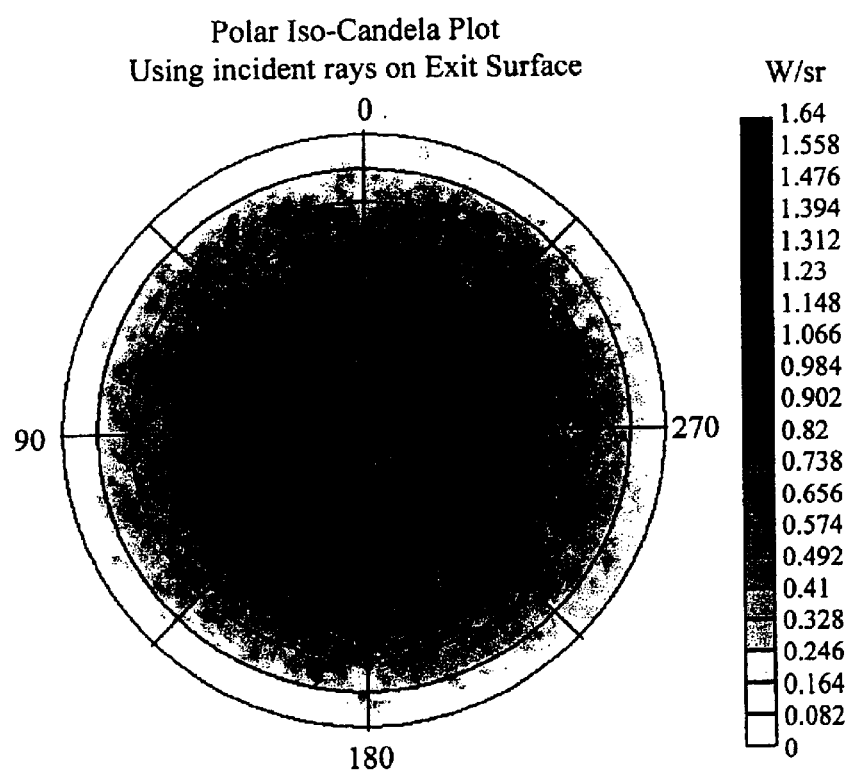
Figure 15C:
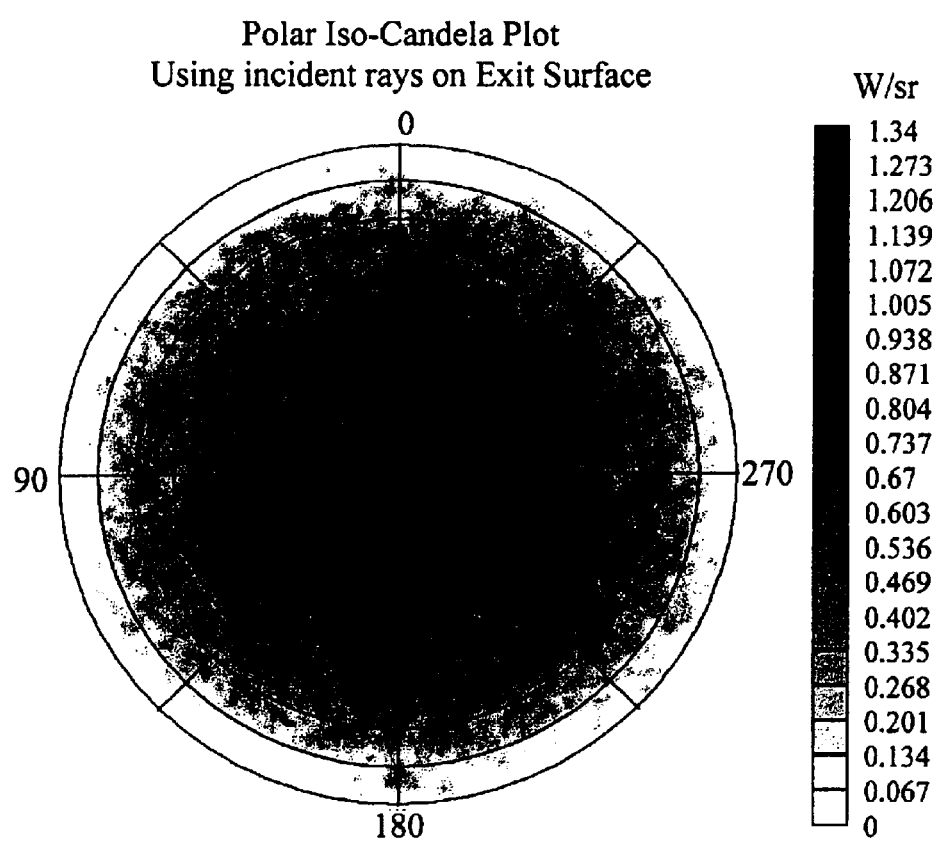

Rotating the filament of FIG. 15a by 90-degrees produces an intensity plot illustrated by FIG. 15b. Again, there are minor differences between the intensity plots after, and prior to, the rotation. Translation of the filament of FIG. 15a by one millimeter, as depicted in Figure 15c, once again documents reduction in variation of angular distribution as compared to the plots of FIGS. 15a–b.

The ray trace plots of FIGS. 14(a–c) and 15(a–c) illustrate that the spatial and angular distribution of light at the output of the light pipe is highly stable with respect to modest translations and/or rotations of its filament. This is especially clear when comparing the ray trace plots of FIGS. 14(a–c) and FIGS. 15(a–c) using a light pipe of the present invention with FIGS. 4(a–c) and FIGS. 5(a–c) without the light pipe of the present invention. The light tube of the present invention has been effectively shown through these incidance and intensity plots to eliminate or substantially reduce the light source or illumination system as an interferent associated with chemometric modeling. It has been found that the use of the light pipe in the illumination subsystem of the present invention allows construction of chemometric models of sufficient sensitivity to measure analyte concentrations.

Another embodiment of the illumination subsystem of the present invention is depicted schematically in FIG. 16. In this embodiment, the tungsten halogen source 14 is placed at one focus of an elliptical reflector 110 and the proximal end 111 of a light pipe 112 is placed at the other focus 114. To improve the collection efficiency of the system a separate back reflector 116 is positioned opposite the elliptical reflector 110 to capture and redirect light which would otherwise be lost from the system. The distal end 118 of the light pipe 112 then provides the source of radiation for the spectroscopic sample.

Figure 17:
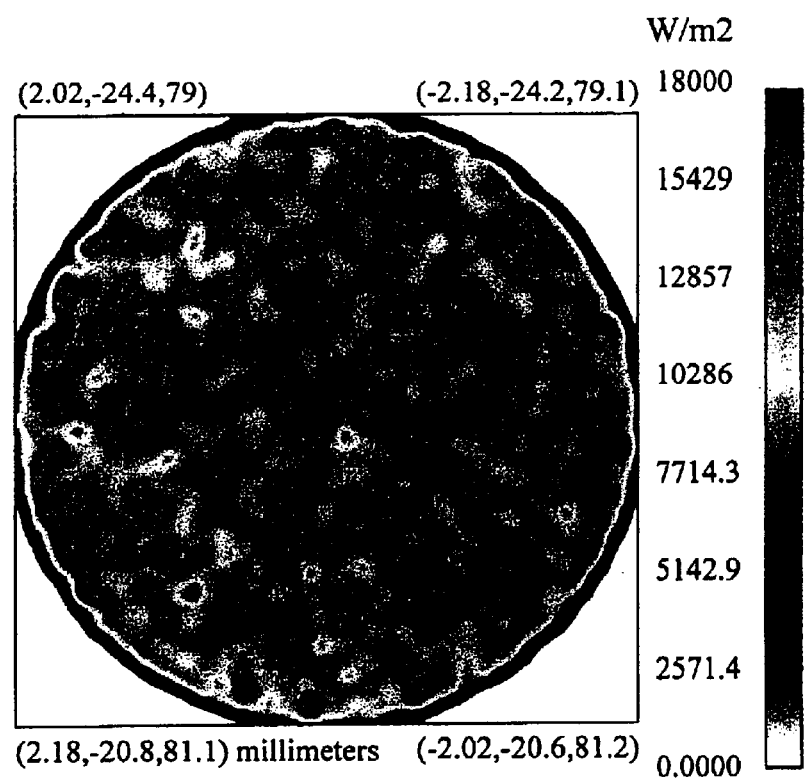
FIG. 17 is an incidance plot depicting homogenization of the light at the distal end of the light pipe of FIG. 16.
Figure 18:
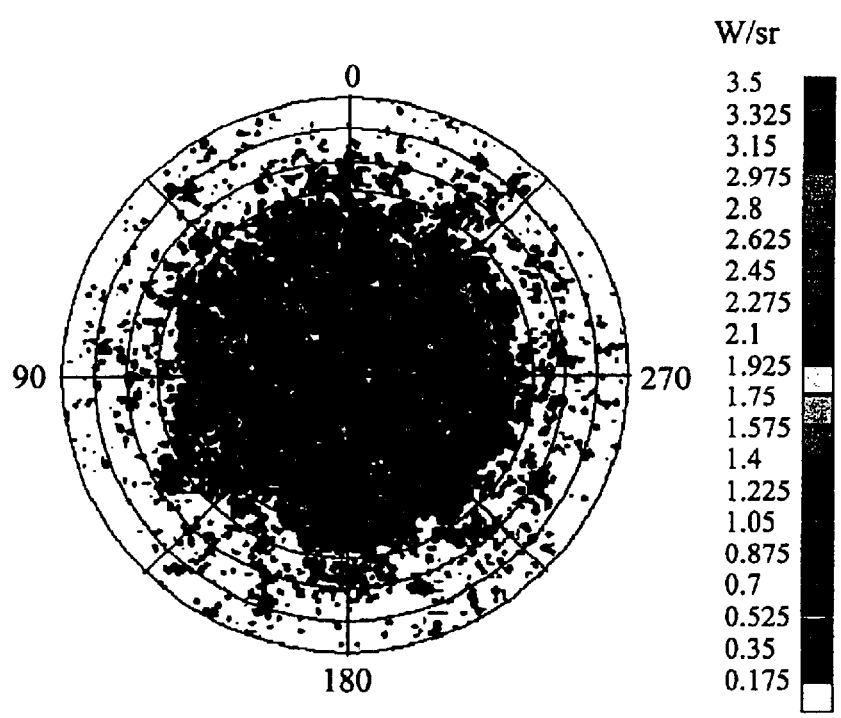
FIG. 18 is an intensity plot showing the homogenization of light emitted from the light pipe of FIG. 16.

FIGS. 17 and 18 show the simulated spatial and angular distributions of the light at the distal end 118 of the light pipe 112 of FIG. 16. These distributions show substantially improved homogenization as compared to the output of the standard system depicted in FIG. 2.

Figure 19:
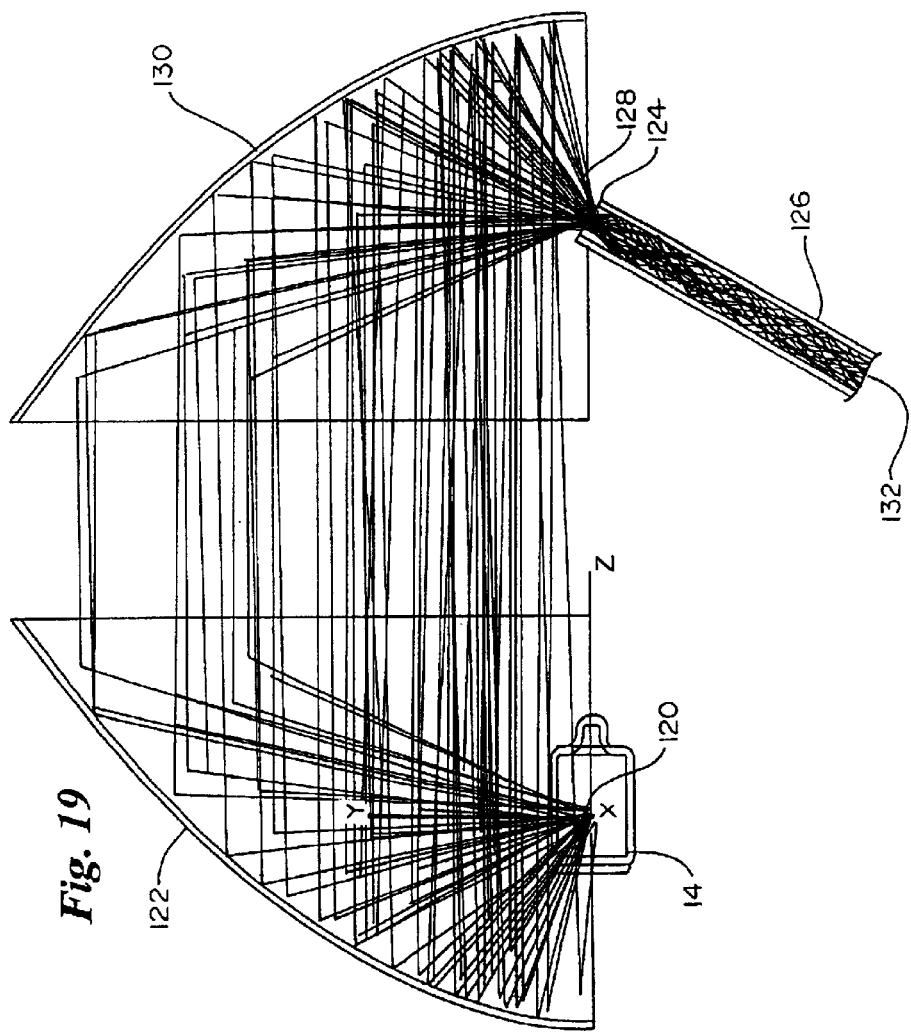
FIG. 19 is a schematic plan view of an alternative illumination source incorporating parabolic reflectors and a light pipe.
Figure 20:
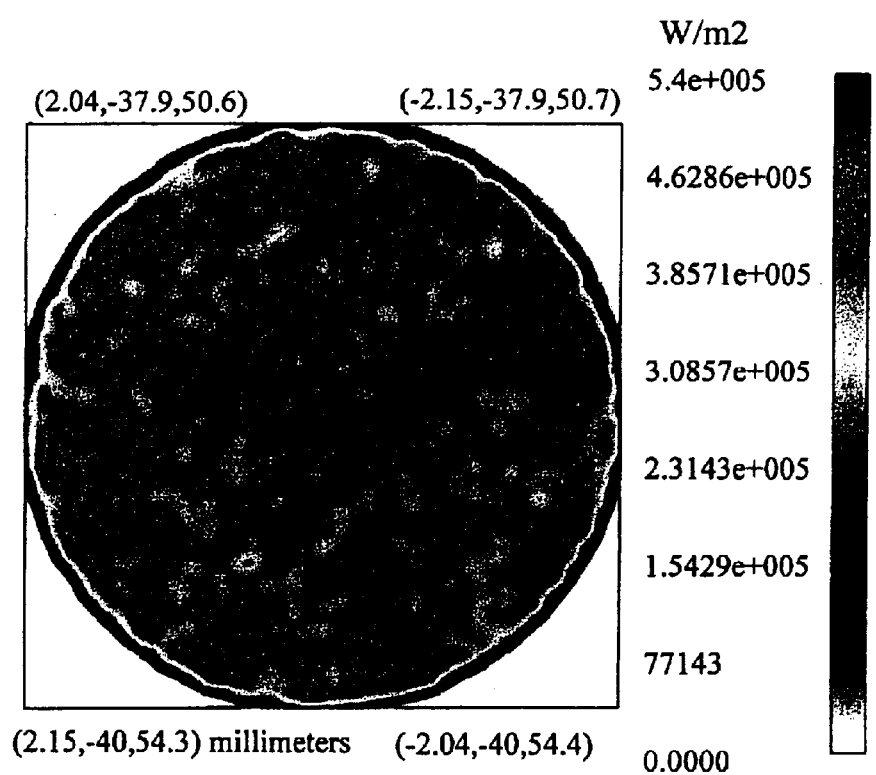
FIG. 20 is an incidance plot depicting spatial homogenization of the light.
Figure 21:
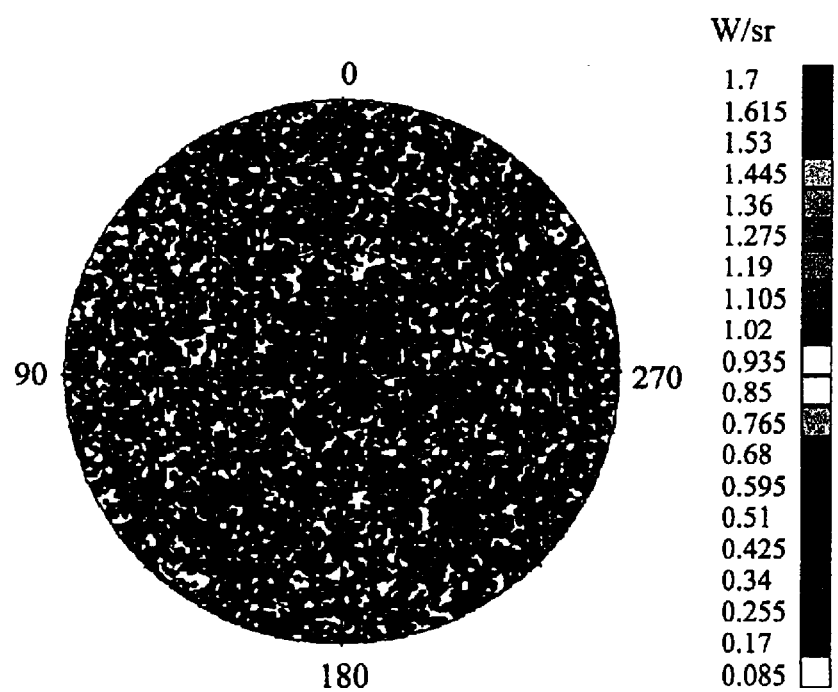
FIG. 21 is a plot of intensity showing the homogenization of light by the source in FIG. 19.

Another embodiment of the present invention is shown in FIG. 19. In this embodiment, the tungsten halogen source 114 is placed at the focus 120 of a section of a parabolic reflector 122 and the proximal end 124 of a light pipe 126 is placed at the focus 128 of a section of another parabolic reflector 130. The homogenized light exits the distal end 132 of the light pipe 126. The simulated spatial and angular distributions of the light at the distal end of the light pipe, shown in FIGS. 20 and 21, show substantially improved homogenization as compared to the output of the standard system depicted in FIG. 2.

Figure 22:
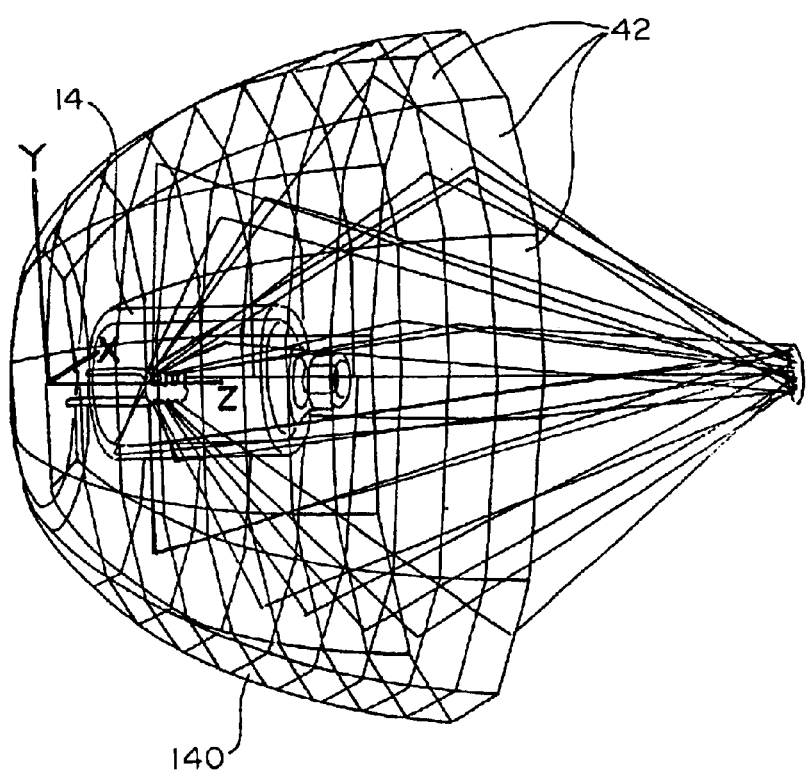
FIG. 22 is a schematic perspective view of an alternative illumination source incorporating faceted reflectors.
Figure 23:
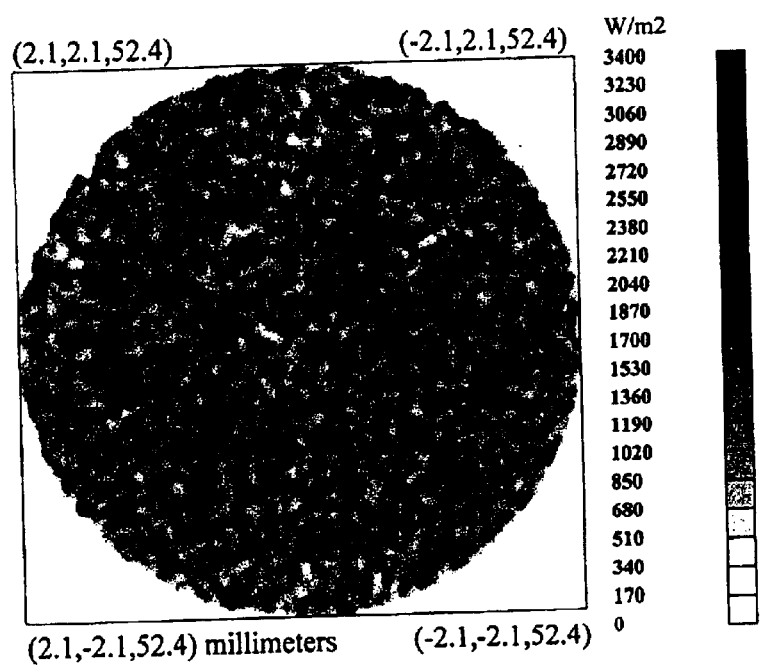
FIG. 23 depicts spatial distribution of the light showing spatial homogenization achieved through the system of FIG. 22.
Figure 24:
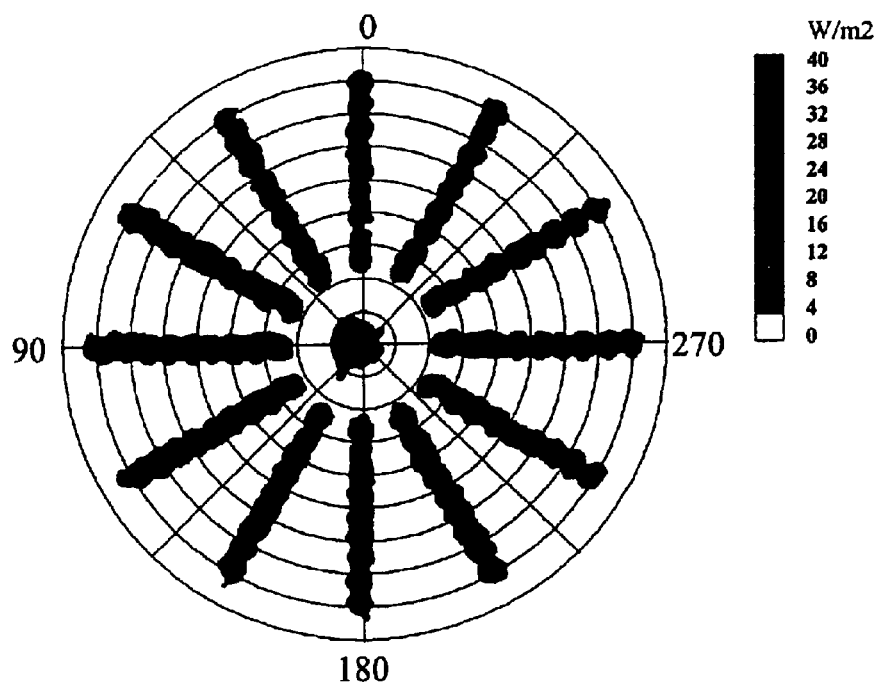
FIG. 24 is a plot of angular distribution produced by the device of FIG. 22.

Another embodiment of the present invention is shown in FIG. 22. This embodiment is similar to the standard system depicted in FIG. 2, except that the standard elliptical reflector has been replaced with a faceted reflector 140. This faceted reflector 140 has the same general form as the elliptical reflector of FIG. 2, but the smoothly varying shape of the standard elliptical form has been replaced with flat mirror facets 142 which locally approximate the standard shape. Such faceted reflectors 142 provide a high degree of spatial uniformity. FIG. 23 is a simulated spatial distribution of the light at the second focus of the ellipse, showing substantially improved spatial homogeneity as compared to the output of the standard system of FIG. 2. FIG. 24 is a simulated angular distribution at the second focus of the ellipse which, unlike the other embodiments disclosed herein, exhibits a high degree of non-uniformity.

The faceted elliptical reflector is an example of an embodiment of an illumination subsystem of the present invention which produces only part of the desired characteristics in the output radiation. In the case of the faceted reflector 140, spatial homogenization is achieved but not angular homogenization. In other cases, such as passing the output of the standard system through ground glass, angular homogenization is achieved but not spatial homogenization. In embodiments such as these, where only angular or spatial homogenization is produced (but not both) some improvement in the performance of the spectroscopic system may be expected. However, the degree of improvement would not be expected to be as great as for systems where spatial and angular homogenization of the radiation are simultaneously achieved.

Another method for creating both angular and spatial homogenization is to use an integrating sphere in the illumination subsystem. Although common to use an integrating sphere for detection of light, especially from samples that scatter light, integrating spheres have not been used as part of the illumination subsystem when seeking to measure analytes non-invasively. In practice, radiation output from the emitter could be coupled into the integrating sphere with subsequent illumination of the tissue through an exit port. The emitter could also be located in the integrating sphere. An integrating sphere will result in exceptional angular and spatial homogenization but the efficiency of this system is significantly less than other embodiments previously specified.

Figure 25:
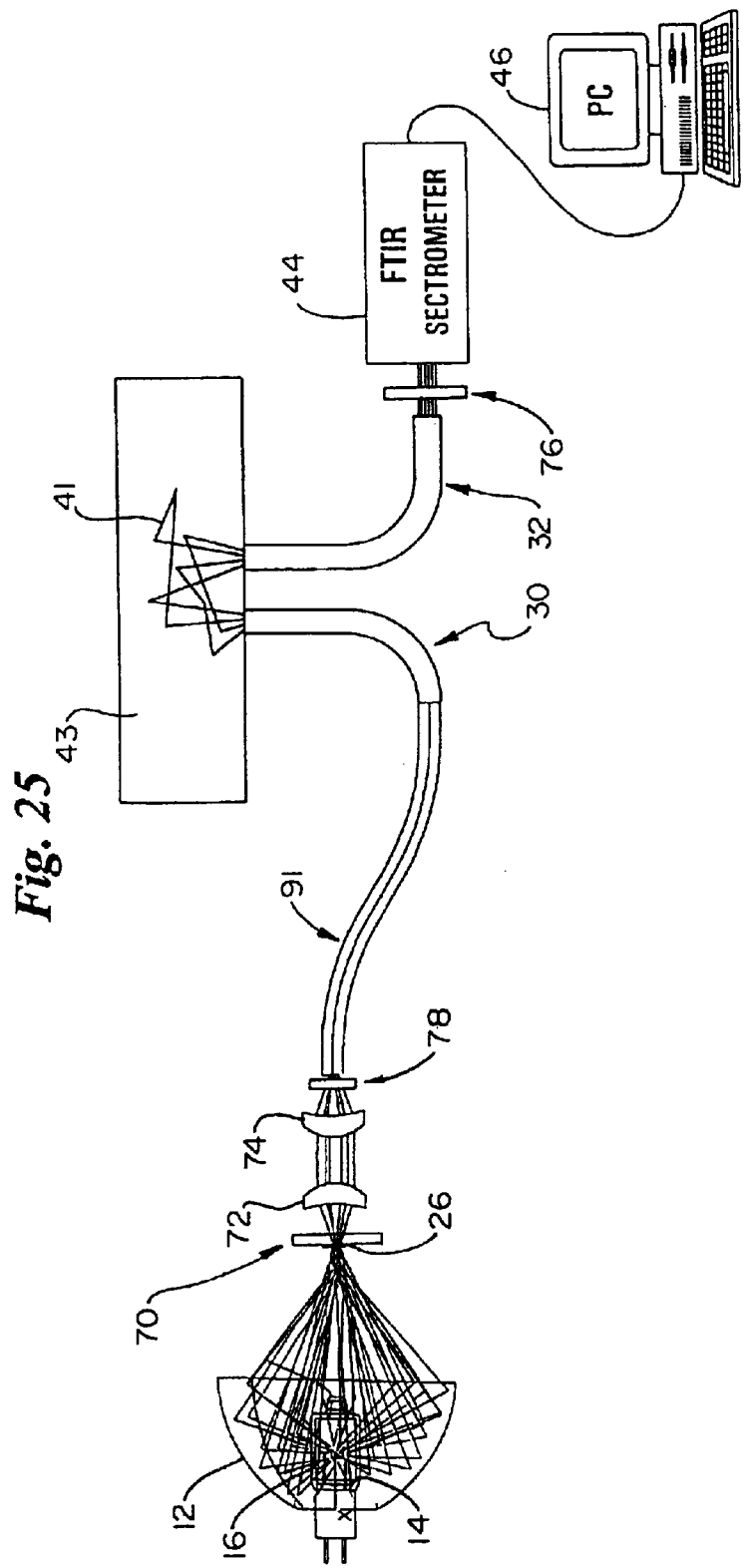
FIG. 25 is a diagramed view of a system of the present invention for measuring glucose in scattering media having a tissue phantom as the sample source.

In order to evaluate the efficacy of the light tube of the present invention for reducing prediction error related to lamp variations, an experiment was conducted comparing a chemometric model using a light pipe of the present invention with a chemometric model without the light pipe of the present invention. The system of FIG. 9 depicts the system without the light pipe. FIG. 25 is a diagramed view of the system of the present invention for measuring glucose in scattering media having a tissue phantom 43 as the sample source. The apparatus diagramed in FIG. 25 is consistent with that discussed in detail with respect to FIG. 9 except for the S-bend light pipe 91 which is included at the focus of the second silicon lens 74.

Figure 26A:
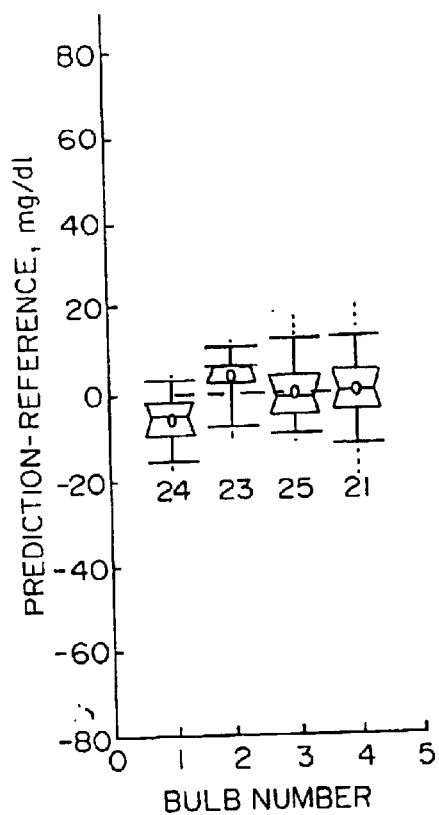
FIG. 26a is a box and whisker plot of a standard system with no bulb changes.
Figure 26B:
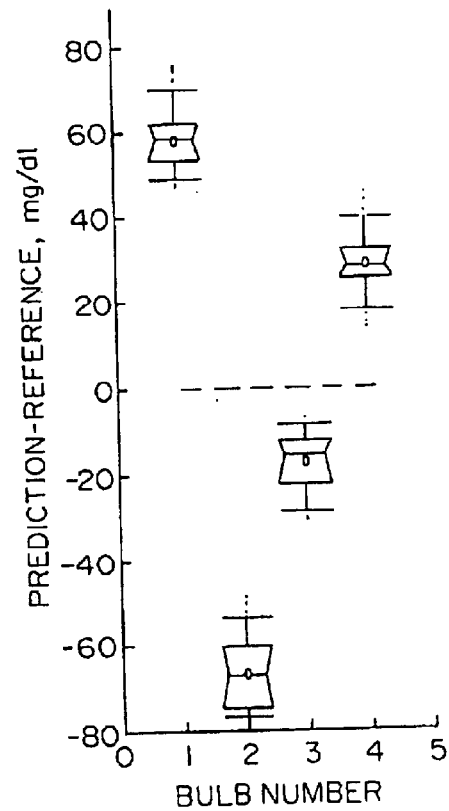
FIG. 26b is a box and whisker plot of a standard system across four bulb changes.
Figure 26C:
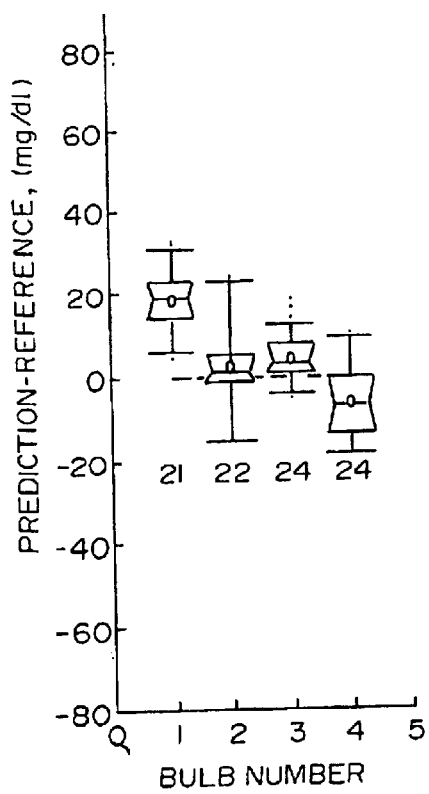
FIG. 26c is a box and whisker plot of a system using an s-bend light pipe across four bulb changes.
Figure 26D:
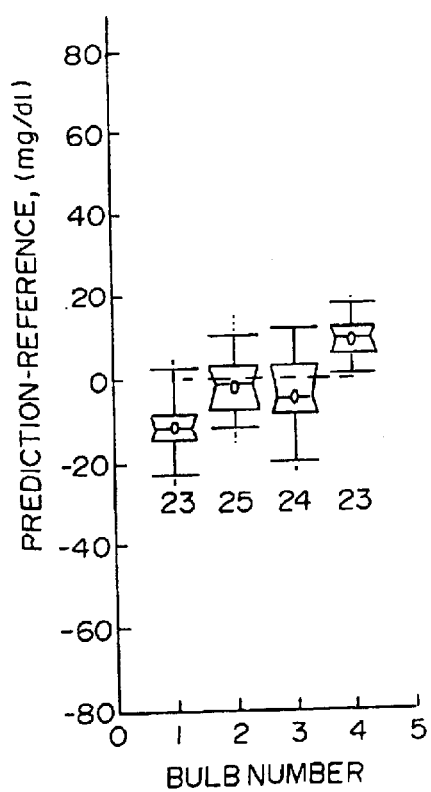
FIG. 26d is a box and whisker plot of a system using a ground glass diffuser plus and s-bend light pipe across four bulb changes.

The results of comparative testing between the system of FIG. 9 and that of FIG. 25 which incorporates the light pipe are included in the box and whisker plots of FIGS. 26a through 26d. FIGS. 26a and 26b are duplicates of FIGS. 10a and 10b to provide easy comparison with the results included in FIGS. 26c and 26d. Thus, FIG. 26a depicts the ability of the standard system with no bulb changes to predict glucose concentrations. FIG. 26b depicts the system ability across four bulb changes. FIG. 26c depicts the results of the system of FIG. 25 across four bulb changes. FIG. 26d shows the results of tests done on the system of FIG. 25, but with the addition of a ground glass diffuser 78 prior to the light pipe 91. FIGS. 26c and 26d clearly show that the embodiments of FIG. 25 are highly effective in improving the predictive accuracy of the apparatus and chemometric model over the system of FIG. 9. Further, the greatest benefit is derived when the ground glass diffuser 78 and the S-bend light pipe 91 are used together which results in the highest degree of homogenization of the light incident on the sample.

The performance of the illumination subsystem of the present invention relative to a known radiation emitter difference can be quantified. A method for quantifying the performance of the illumination system is to create both angular and spatial distribution plots under two known but different conditions. The differences between the two similar metric plots can be quantified. The known emitter difference to be used for quantification is preferably a one-millimeter translation of the lamp filament.

Angular and spatial distribution plots can be created by using standard ray trace packages such as TracePro V2.1 or through direct measurements. The image of the illumination system beam can be measured by using any standard intensity mapping scheme and by using a goniometer. This allows both the spatial and angular distributions of the illumination output to be determined.

Optical modeling or direct measurement of the system should occur before and after movement of the filament. In order to standardize the calculation for many applications, the image should be divided into approximately one hundred equally sized "bins" (or squares), with ten bins across the diameter of the output image. This requirement is easily satisfied when performing ray trace analysis and can be accomplished by either measuring the beam in a ten by ten grid or by sampling at finer spacing and then averaging the data. The spatial and angular distributions for the initial emitter state are then subtracted from the corresponding distributions after movement of the lamp filament by one millimeter. The resulting images represent either the angular or spatial variance that occurred due to the emitter perturbation. In order to quantify the angular or spatial variance, all the data in the different images are put into a vector for easier calculation, and the vector is normalized so that its length equals 1. This normalization is achieved by dividing each data point by the 2-norm ($\|\cdot\|_2$), which is equivalent to the Euclidean distance of the vector, $$\|x\|_2 = \left(\sum_{i=1}^{n} \|x\|^2\right)^{1/2} \qquad \text{Eq. (1)}$$

where X is the vector of the difference image and n is the number of data points in the vector.

The normalization step ensures that the magnitude of every difference-image is comparable. Following the normalization step, the standard deviation of the normalized image vector is calculated, and this metric is an indication of the amount of variance introduced by the known emitter difference, $$\text{Metric} = \frac{\sum_{i=1}^{n}\left(\frac{x}{\|x\|_2} - \text{mean}\left(\frac{x_i}{\|x\|_2}\right)\right)^2}{n-1} \qquad \text{Eq. (2)}$$

The standard deviation of the normalized image vector for both angular and spatial distributions was calculated for three different illumination systems.

1. Acceptable System: This illumination system is a light source (40-watt tungsten-halogen bulb) focused by an elliptical reflector into a ground glass diffuser, specified as a weak angular homogenizer, with subsequent coupling into a hexagonal light pipe with a length to diameter aspect ratio of 3 to 1. The system is modeled such that the filament image fully fills the input into the hexagonal light pipe.
2. Preferred System: the illumination system is the same as the acceptable except that the length to diameter aspect ratio is 7 to 1.
3. Ideal System: The illumination system is composed of a light source (40-watt tungsten-halogen bulb) focused by an elliptical reflector into a ground glass diffuser, specified as a strong angular homogenizer, with subsequent coupling into an s-bend hexagonal light pipe with a length to diameter aspect ratio of 7 to 1. The system is modeled such that the filament image fully fills the input into the hexagonal light pipe.

Based upon testing with these three illumination systems, the degree of homogenization can be generally classified as acceptable, preferred and ideal. Table 2 shows the standard deviations of the spatial distribution for the three systems. Table 3 shows the standard deviation for angular distribution.

TABLE 2

|            | Vertical Filament | Filament Rotation |
|------------|-------------------|-------------------|
| Acceptable | 0.053             | 0.050             |
| Preferred  | 0.045             | 0.042             |
| Ideal      | 0.039             | 0.034             |

TABLE 3

|            | Vertical Filament | Filament Rotation |
|------------|-------------------|-------------------|
| Acceptable | 0.044             | 0.066             |
| Preferred  | 0.032             | 0.054             |
| Ideal      | 0.027             | 0.050             |

There is another metric that can be used to evaluate the efficacy of an illumination system in reducing error inflation following bulb changes. This metric is known as the multivariate signal to noise (mSNR). The typical signal to noise (S/N) calculation is a univariate measure; it is defined as the maximum signal in a spectrum divided by the standard deviation of the baseline noise.

When a multivariate calibration is used, the signal from two or more wavelengths is used to quantify the analyte of interest. Because of this, unless the noise is random or 'white' noise, the standard deviation of the baseline (as used in univariate S/N calculations) is an inexact and inappropriate noise estimate. Furthermore, the maximum signal in the spectrum is also an inexact and inappropriate measure of the overall signal since the multivariate calibration uses signals from multiple wavelengths. The mSNR metric, however, uses the multivariate net analyte signal and the error covariance matrix and therefore gives a better estimate of the signal to noise for multivariate calibrations.

Figure 57:
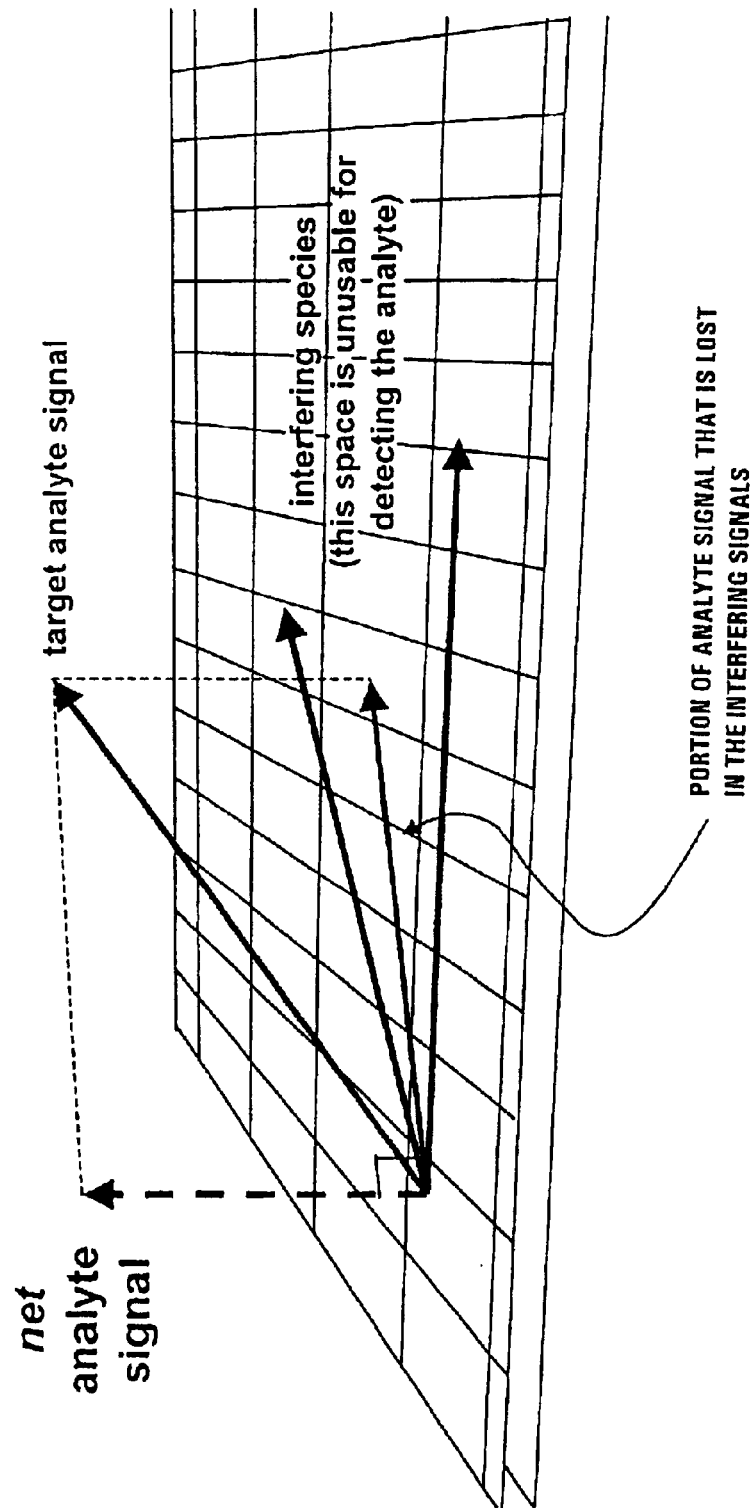
FIG. 57 is a graphical depiction of the concept of net analyte signal in a three-component system.

The net analyte signal is that part of the analyte spectrum which is orthogonal (contravariant) to the spectra of all interferents in the sample. If there are no interfering species, the net analyte spectrum is equal to the analyte spectrum. If interfering species with similar spectra to the analyte are present, the net analyte signal will be reduced relative to the entire spectrum. The concept of net analyte signal for a three-component system is depicted graphically in FIG. 57. Because the calibration depends on the net analyte signal, the multivariate signal to noise metric takes this measure into account.

The mSNR can be calculated if two pieces of information are known. The net analyte signal (NAS) for the analyte of interest must be known, but this may be estimated from the regression vector, b (the model), $$NAS = \frac{\hat{b}}{\|\hat{b}\|_2^2} \qquad \text{Eq. (3)}$$

where $\|.\|_2$ represents the 2-norm of the vector.

The error covariance matrix ($\Sigma$), which describes the error structure of the multi-wavelength spectral data, is also needed for the mSNR calculation, $$\Sigma = \epsilon^{\tau*}\epsilon \qquad \text{Eq. (4)}$$

where $\epsilon$ is a vector containing the noise at each wavelength.

$$x = x_0 + \epsilon \qquad \text{Eq. (5)}$$

where x is a measured spectrum, $x_0$ is the "true" spectrum in the absence of noise, and $\epsilon$ is the noise.

The error covariance matrix, $\Sigma$, measures how noise is correlated across wavelengths. The spectra used to calculate the error covariance matrix are spectra that have a constant amount of the analyte of interest and are obtained or processed in a manner to identify the spectral variances due to the variance of interest. In practice, a repeat sample should be used and the only variance introduced into the system should be the spectral variance being identified. In this invention, the variance source of interest is spectral variance due to emitter changes. Thus, spectral data from a repeat sample is obtained using different emitters. If the noise is uncorrelated, the error covariance matrix will have no off-diagonal elements, but in many cases, this will not be true. In such cases, the error may 'overlap' spectrally with the net analyte signal. In other words, this will introduce 'Noise' into the measurement of this particular analyte. The 'Noise' may be calculated as, $$\text{Noise} = \sqrt{v^T \Sigma\, v} \qquad \text{Eq. (6)}$$

where $$v = \frac{NAS}{\|NAS\|_2} \qquad \text{Eq. (7)}$$

The mSNR at unit concentration may then be calculated by, $$mSNR = \frac{\|NAS\|_2}{\text{Noise}} = \frac{\|NAS\|_2}{\sqrt{v^T \Sigma\, v}} \quad \text{Eq. (8)}$$

The inverse of the net analyte spectrum, 1/mSNR, is an estimate of how much error will be added to prediction estimates if the type of noise in ϵ is present in the spectra being used to predict the analyte concentration (or other property).

When an illumination system is insensitive to emitter variances, there will be little effect on the spectral noise; in other words, the error covariance matrix, Σ, will be close to diagonal. In that case, the mSNR will be high. In the case where the system is sensitive to emitter variances or source fluctuations, correlated noise will be introduced and that will create off-diagonal elements which will be present in the error covariance matrix Σ. When these spectral variances or noise interfere (co-vary) with the net analyte signal, the mSNR gets smaller and its inverse increases.

Table 4 shows the mSNR and 1/mSNR values calculated for three different illumination systems. These systems include a standard system with no bulb changes, the preferred embodiment system (with s-bend light pipe and diffuser) and also one that contained a straight light pipe (acceptable system).

TABLE 4

| System | mSNR | 1/mSNR |
|---|---|---|
| No bulb change (Ideal level) | 0.2 | 5 |
| Bent light pipe & diffuser (Preferred level) | 0.033 | 30 |
| Straight light pipe only (Acceptable level) | 0.0166 | 60 |

It is clear that bulb changes influence each system differently. The mSNR is highest when no bulb change occurs, and lowest when the standard system with limited source homogenization is used. Conversely, the greatest inflation in prediction errors can be seen in that system (approximated by 1/mSNR).

These mSNR values were calculated using the study measuring the 98-solution set that was described previously. The NAS was calculated using the model (b) generated from the data set where a single bulb was used (equation 1). This model had no knowledge of bulb changes, and so the net analyte signal corresponds to that in the absence of source fluctuations. For each illumination system, there were four bulb changes as described before. For each bulb, in addition to the 90-solution set, additional 'repeat' samples were measured. These 'repeats' were simply samples that contained all of the analytes at concentrations at the center of the calibration. Thus, to isolate the spectral variance due to bulb changes the spectral data was processed in the following manner. Multiple 'repeat' spectra at each bulb were measured, and the average repeat spectrum for each bulb was calculated using these data, hereafter referred to as the average bulb spectrum. Each average bulb spectrum can be thought of as the 'x' in equation 5. The mean repeat spectrum is simply the average spectrum of the average bulb spectra. To calculate the error, ϵ, associated with each bulb, the mean repeat spectrum was subtracted from the average bulb repeat spectra, $$\varepsilon_i = x_i - \frac{\sum_{i=1}^{n} x_i}{n} \quad \text{Eq. (9)}$$

where n is the number of bulbs in the analysis (4 in this example). The Σ matrix was then calculated using equation 4, and equations 6–8 were then calculated to find the mSNR.

Figure 27:
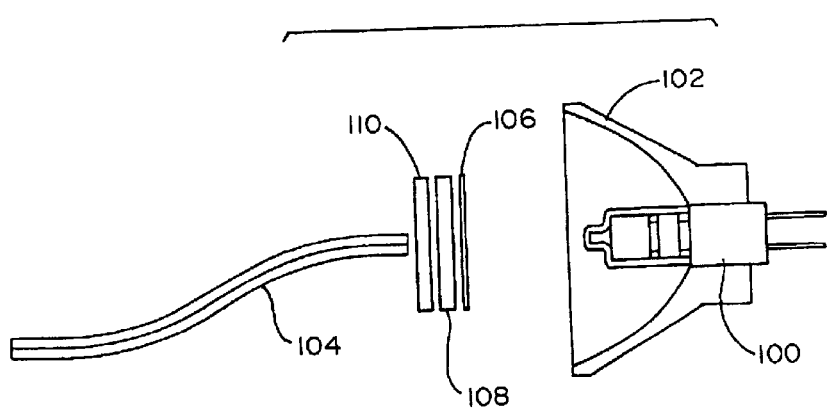
FIG. 27 is a diagrammed view of a system incorporating filters prior to the light pipe which eliminate unwanted wavelengths of radiation from the illumination source.

Now referring to FIG. 27, another aspect of the present invention is depicted. The system depicted provides spectral filtering or bandpass filtering to eliminate unnecessary wavelengths or bands of wavelengths from the light prior to contact with the tissue. This is accomplished by placing one or more elements between the light source and tissue. The elements can include absorptive filters fabricated of any transparent or partially transparent substrate; single layer or multi-layer dielectric coatings deposited on any transparent or partially transparent substrate; a grating or prism which disperses the radiation, permitting unwanted wavelengths to be blocked from reaching the tissue; and/or an aperture which selectively blocks undesirable radiation.

A preferred system for bandpass filtering is depicted in FIG. 27 which depicts a light source 101 placed within an electrical reflector 102. FIG. 27 also depicts a hexagonal S-bend light pipe 104 to receive light from the source 101. A series of filters are placed between the light source 101 and the light pipe 104. The first optical filter is a silicon filter 106 which is anti-reflection coated to transmit at least ninety percent (90%) of the in band incident light. The silicon filter passes wavelengths of light longer than 1.1 micron The second optical filter is preferably a KOPP 4-67 colored glass filter 108 that, in combination with the silicon filter, passes light in the 1.2 to 2.5 micron spectral region. The slope of the KOPP filter is such that is preferentially passes light at wavelengths between 2.0 and 2.5 micron. The third optical filter is an ORIEL WG295 absorption filter 110 that cuts out wavelengths longer than 2.5 micron. The front surface of the WG295 filter can be polished or finely ground. If the front surface is finely ground, the WG295 acts as a diffuser as well as a light filter. It has been found that these filters prevent burning of the tissue, while enhancing the signal-to-noise ratio of the system by band limiting the light to only the spectral region of interest. The effect of band limiting the light is to reduce shot noise generated by the photon flux incident on the detector.

An alternative combination of filters to achieve spectral bandpass filtering is depicted in FIG. 6. With this embodiment, the two silicon lenses 72,74 absorb wavelengths shorter than approximately 1.2 microns and longer than approximately 10 microns. The cyan filter 76 is an absorptive filter such as a Hoya CM-500 to absorb mid-infrared radiation at wavelengths of approximately 2.8 microns and longer. Further, a SCHOTT WG-295 absorptive filter 78 is included to absorb radiation at wavelengths approximately 2.7 micron and higher. FIG. 28 graphically depicts the individual and combined spectral transmission of the components shown in FIG. 6, along with the "spectral fingerprint" of glucose. As depicted in the graphs, this combination of absorptive filters and silicon lenses acts to block unwanted wavelengths, while still permitting transmission of radiation in the glucose fingerprint region. Similar combinations of filters can be utilized based on analytes of interest to be analyzed.

It is also recognized that other modifications can be made to the present disclosed system to accomplish desired homogenization of light. For example, the light source could be placed inside the light pipe in a sealed arrangement which would eliminate the need for the reflector. Further, the light pipe could be replaced by an integrator, wherein the source is placed within the integrator as disclosed in U.S. patent application Ser. No. 09/832,631, entitled "Encoded Multiplex Variable Filter Spectrometer," filed on the same date herewith and incorporated by reference.

Figure 29:
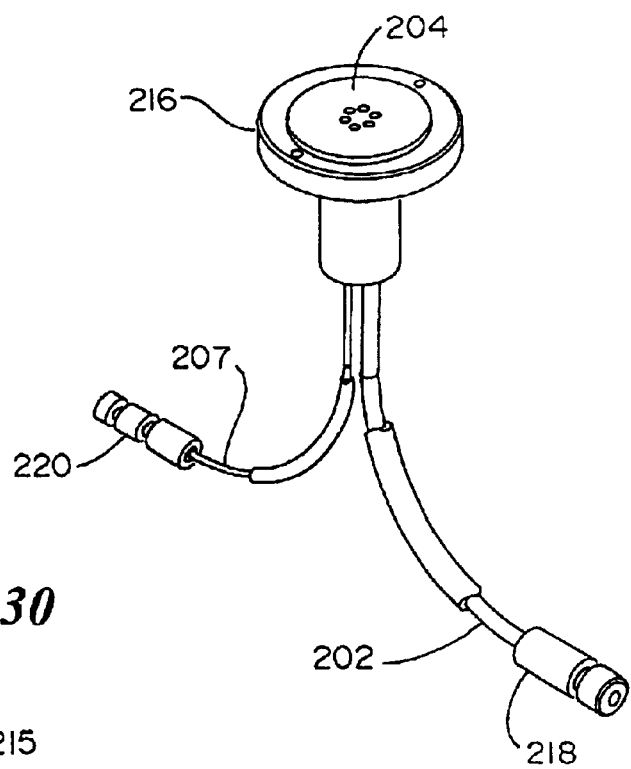
FIG. 29 is a perspective view of elements of a preferred tissue sampling subsystem.
Figure 30:
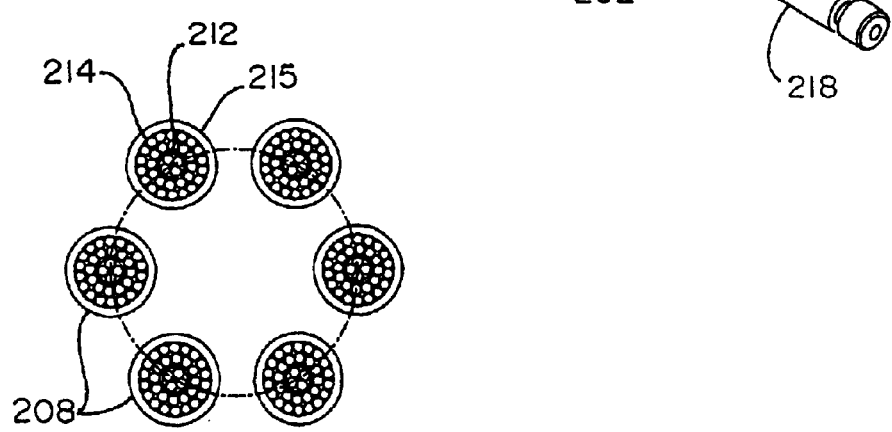
FIG. 30 is a plan view of the sampling surface of the tissue sampling subsystem of FIG. 29, showing a preferred arrangement of input and output optical fiber ends.
Figure 31:
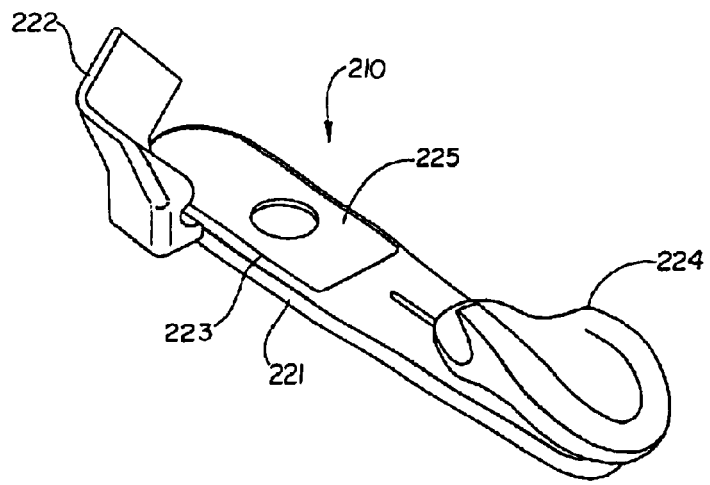
FIG. 31 is a perspective view of a preferred ergonomic apparatus for holding the sampling surface and positioning a tissue surface thereon.

The purpose of the tissue sampling subsystem 200 is to introduce radiation generated by the illumination subsystem 100 into the tissue of the subject and to collect the portions of the radiation that are not absorbed by the tissue and send that radiation to the FTIR spectrometer subsystem 400 for measurement. FIGS. 29, 30 and 31 depict elements of a preferred tissue sampling subsystem 200. Referring first to FIG. 29, the tissue sampling subsystem 200 has an optical input 202, a sampling surface 204 which forms a tissue interface 206 that interrogates the tissue and an optical output 207. The subsystem further includes an ergonomic apparatus 210, depicted in FIG. 31, which holds the sampling surface 204 and positions the tissue at the interface 206. In a preferred subsystem, a device that thermostats the tissue interface is included and, in some embodiments, an apparatus which repositions the tissue on the tissue interface in a repetitive fashion is included.

The optical input 202 of the tissue sampling subsystem 200 receives radiation from the illumination subsystem 100 (i.e., light exiting the light pipe) and transfers that radiation to the tissue interface 206. The optical input may consist of a bundle of optical fibers that are arranged in a geometric pattern that collects the most light possible from the illumination subsystem. One preferred arrangement is depicted in FIG. 30. The plan view depicts the ends of the input and output fibers in a geometry at the sampling surface including six clusters 208 arranged in a circular pattern. Each cluster includes four central output fibers 212 which collect diffusely reflected light from the tissue. Around each grouping of four central output fibers 212 is a cylinder of material 215 which ensures about a 100 $\mu$m gap between the edges of the central output fibers 212 and the inner ring of input fibers 214. The 100 $\mu$m gap is important to target glucose in the dermis. As shown in FIG. 30, two concentric rings of input fibers 214 are arranged around the cylinder of material 215. As shown in one preferred embodiment, 32 input fibers surround the four output fibers. The high ratio of input-to-output fibers is maintained in all preferred embodiments in recognition of loss within the tissue.

All of the clustered input and output fibers are potted into a cluster ferrule which is glued into a sampling head 216. The sampling head 216 includes the sampling surface 204 which is polished flat to allow formation of a good tissue interface. Likewise, the input fibers are clustered into a ferrule 218 connected at the input ends to interface with the illumination subsystem 100. The output ends of the output fibers are clustered into a ferrule 220 for interface with the FTIR spectrometer subsystem 400.

Alternatively, the optical input may not require any fibers and may instead use a combination of light pipes, refractive and/or reflective optics to transfer the maximum amount of input light to the tissue interface. It is important that the input optics of the tissue sampling subsystem collect as much light as possible from the illumination subsystem 100 in order to maximize the SNR achieved by the overall system. In the art, FTIR spectrometer-based non-invasive glucose monitoring systems have been described with the illumination subsystem before the FTIR spectrometer and the tissue sampling subsystem after the FTIR spectrometer. This configuration as described in the art has the disadvantage of limiting the total throughput of the system because the FTIR spectrometer cannot support a large range of angles from the illumination subsystem due to spectral resolution and physical size requirements. In the present invention, the placement of the illumination subsystem 100 and tissue sampling subsystem 200 before the FTIR spectrometer subsystem 400 results in over an order of magnitude improvement in throughput for a given size of FTIR spectrometer because the input to the tissue sampling subsystem 200 is designed to handle the wide range of angles from the illumination subsystem 100 and the small output image size of the tissue sampling subsystem is better matched to the throughput supported by a reasonably sized FTIR spectrometer. The source, sample, FTIR spectrometer, detector (SSFD) configuration for non-invasive glucose monitoring is a significant improvement over the current art.

The tissue interface is another critical part of the tissue sampling subsystem. It must irradiate the tissue in a manner that targets the glucose bearing compartments of the tissue and discriminates against light that does not travel a significant distance through those compartments. As stated above, the 100-$\mu$m gap discriminates against light which contains little glucose information. In addition, the tissue interface may need to average over a certain area of the tissue to reduce errors due to the heterogeneous nature of the tissue. The tissue sampling interface should reject specular and short pathlength rays and it must collect the portion of the light that travels the desired pathlength through the tissue with high efficiency in order to maximize the SNR of the system. The tissue sampling interface may employ optical fibers to channel the light from the input to the tissue in a predetermined geometry as discussed above. The optical fibers may be arranged in pattern that targets certain layers of the tissue that contain good glucose concentration information. The spacing and placement of the input and output fibers can be arranged in an optimal manner to achieve effective depth targeting. In addition to the use of optical fibers, the tissue sampling interface can use a non-fiber based arrangement that places a pattern of input and output areas on the surface of the tissue when using diffuse reflectance. Proper masking of the non-fiber based tissue sampling interface ensures that the input light travels a minimum distance in the tissue and contains valid glucose concentration information. Finally, the tissue sampling interface may be thermostatted to control the temperature of the tissue in a predetermined fashion. The temperature of the tissue sampling interface is set such that the invention reduces prediction errors due to temperature variation and also such that glucose direction of change can be inferred by the equilibration of the interstitial space with capillary blood glucose levels. In preferred embodiments, the sampling head 216 is heated to between 34° C. and 40° C. in order to thermostat the tissue. This promotes equilibration of glucose between the interstitial fluid and the capillary blood. Further, reference errors are reduced when building a calibration model. These methods are disclosed in commonly assigned U.S. patent application Ser. No. 09/343,800, entitled "Method and Apparatus for Non-Invasive Blood Analyte Measurement with Fluid Compartment Equilibration," the disclosure of which is incorporated herein by reference.

The tissue sampling subsystem generally will employ an ergonomic apparatus or cradle 210 that positions the tissue over the sampling interface 206 in a reproducible manner. A preferred ergonomic apparatus 210 is depicted in FIG. 31. In the case of sampling the underside of the forearm, an ergonomic cradle design is essential to ensure good contact with the sampling interface. The ergonomic cradle 210 includes a base 221 having an opening 223 therethrough. The opening is sized for receiving the sample head 216 therein to position the sampling surface 204 generally coplanar with an upper surface 225 of the base 221. The ergonomic cradle 210 references the elbow and upper arm of the subject via a bracket 222 in conjunction with a float-to-fit handgrip 224 to accurately position the forearm on the tissue sampling interface. Careful attention must be given to the ergonomics of the tissue sampling interface or significant sampling error can result. Errors in sampling the tissue have been found to be a major source of reduced accuracy and precision for the non-invasive measurement of glucose.

The ergonomic cradle 210 of the present invention is an important part of the tissue sampling subsystem 200. The cradle is designed such that the forearm of the subject is reliably located over the sample head 216. The bracket 222 forms an elbow rest that sets the proper angle between the upper arm and the sampling head 216, and also serves as a registration point for the arm. The adjustable hand rest 224 is designed to hold the fingers in a relaxed manner. The hand rest position is adjusted for each subject to accommodate different forearm lengths. In preferred embodiments, a lifting mechanism is included which raises and lowers the cradle periodically during sampling to break and reform the tissue interface. Reformation of the interface facilitates reduction of sampling errors due to the rough nature and inhomogeneity of the skin.

The image formed by the output of the tissue sampling subsystem is typically an order of magnitude smaller in size than its input. This input image to output image ratio is necessary to match the throughput supported by the FTIR spectrometer while maximizing the overall system signal to noise ratio. The output of the tissue sampling subsystem 200 transfers the portion of the light not absorbed by the tissue that has traveled an acceptable path through the tissue to the input of the FTIR spectrometer subsystem 400. The output of the tissue sampling subsystem 200 may use any combination of refractive and/or reflective optics to produce a collimate beam that will be modulated by the FTIR spectrometer. In preferred embodiments, the diffusely reflected light collected by the output fibers 207 of the sampler head 216 are collimated by a plano-aspheric lens made of ZnSe. The design of the lens is such that the collimated beam has less than five degrees of divergence. This lens 228 is schematically depicted in FIG. 1 as part of the FTIR spectrometer subsystem 400. The collimating lens 228 produces a beam with low optical distortion that serves as the proper input to the FTIR spectrometer discussed below.

Figure 32:
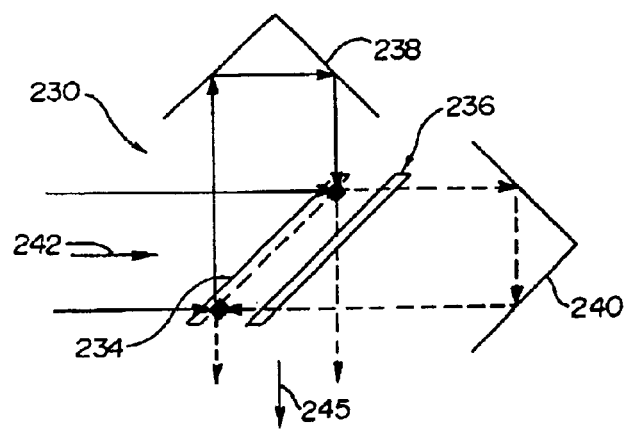
FIG. 32 is a simplified schematic view of an FTIR spectrometer utilized in a subsystem of the present invention.

As shown in FIG. 1, the FTIR spectrometer subsystem 400 includes a spectrometer 230 that modulates the sufficiently collimated light from the tissue sampling subsystem 200 to create an interferogram which is received by a detector 232. The interferogram spatially encodes the NIR spectrum collected by the tissue sampling subsystem. FIG. 32 schematically depicts one embodiment of an FTIR spectrometer 230 which includes a beamsplitter 234 and compensator optics 236, a fixed retro-reflector 238 and a moving retro-reflector 240. The collimated input light 242 impinges on the beamsplitter optic 234 and is partially reflected and partially transmitted by the coating on the back surface of the beamsplitter 234. The reflected light passes back through the beamsplitter optic 234 and reflects off the fixed retro-reflector 238 and back to the beamsplitter 234. The transmitted light passes through the compensator optic 236 and reflects off the moving retro-reflector 240 and back to the beamsplitter 234. The transmitted and reflected portions of the light recombine at the beamsplitter to create an interference pattern or interferogram. The amount of constructive and/or destructive interference between the transmitted and reflected beams is dependent on the spectral content of the collimated input beam 242 and on the optical path difference between the fixed retro-reflector 238 and the moving retro-reflector 240.

Figure 33:
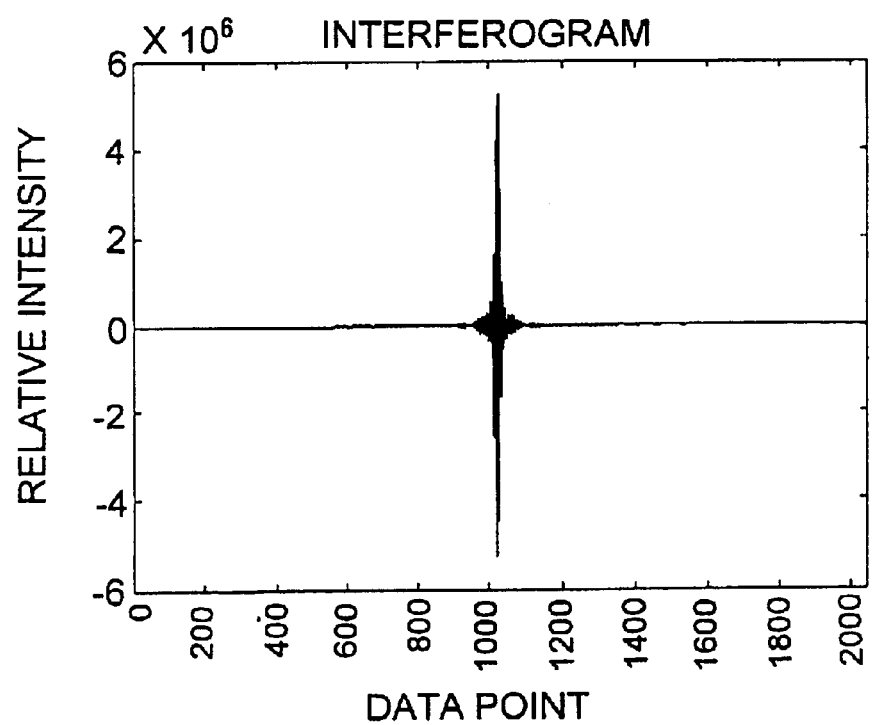
FIG. 33 depicts a typical interferogram created by the spectrometer of FIG. 32.

FIG. 33 shows a typical interferogram created by an FTIR spectrometer. At the point of zero path difference between the transmitted and reflected beams, there will be maximum constructive interference, and the centerburst of the interferogram is created. The interferogram is then focused onto a detector 232, as shown in FIG. 1. The detector 232 converts the optical interferogram into an electrical representation of the interferogram for subsequent digitizing by the data acquisition subsystem 500.

In a preferred embodiment, the non-invasive glucose monitor FTIR spectrometer subsystem 400 utilizes an FTIR spectrometer 230 manufactured by Bomem. This spectrometer utilizes a single plate that contains beamsplitter and compensator functions. In addition, cube corners are used as the end mirrors and both cube corners are moved on a wishbone suspension to create the optical path difference and the subsequent interference record. The Bomem WorkIR™ FTR spectrometer achieves the desired thermal stability and spectral complexity performance necessary for making non-invasive glucose measurements with NIR spectroscopy. The FTIR spectrometer modulates the collimated light from the tissue sampler to spatially encode the NIR spectrum into an interferogram. The spectral resolution of the interferogram can be in the range of 7.5 to 64 wavenumbers. The preferred range of spectral resolution is 30–50 wavenumbers. The interferometer will produce either a single-sided or a double-sided interferogram, with the double-sided interferogram being preferred because it achieves a higher SNR. The resulting interferogram is preferably passed to a condensing lens 244, as shown in FIG. 1, and this lens focuses the light onto the detector 232. The condensing lens 244 is a double convex design with each surface being aspherical in nature. The lens material is ZnSe. The detector 232 is preferably a thermo-electrically cooled, 1 mm diameter, extended range, InGaAs detector that is sensitive to light in the 1.2 to 2.5 $\mu$m region of the spectrum. The detector 232 converts the optical interferogram into its electrical equivalent.

The non-invasive measurement of glucose in humans places extreme requirements on the performance of the instrumentation due to the very small size of the glucose absorption spectrum relative to the water absorption of the body. In addition, interferences due to absorption of other spectroscopically active compounds such as collagen, lipid, protein, etc. reduce the useful portions of the glucose absorption spectrum, yielding a net analyte signal that is very small. To first order approximation, 1 mg/dl of glucose concentration change is equivalent to 1 $\mu$Au of spectral variance for the effective pathlength light travels through tissue using the present invention. Therefore, in order to measure glucose non-invasively with clinically acceptable accuracy, the spectrometer portion of the non-invasive glucose monitor must have a very large signal-to-noise ratio (SNR) and must have excellent photometric accuracy.

The FTIR spectrometer is a critical component of the non-invasive measurement glucose monitoring system of the present invention because it can achieve the required high SNR and photometric accuracy. In the art, there are hundreds of variants of the classic Michelson interferometer design depicted in FIG. 32. One preferred interferometer design is disclosed in commonly assigned U.S. patent application Ser. No. 09/415,600, filed Oct. 8, 1999, entitled "Interferometer Spectrometer with Reduced Alignment Sensitivity," the disclosure of which is incorporated herein by reference. The FTIR spectrometer has throughput advantages (Jaquinot and Fellget advantages) relative to dispersive spectrometers and acousto-optical tunable filters. In addition to high throughput, the use of a reference laser in the FTIR spectrometer gives the device wavenumber axis precision. Wavenumber or wavelength axis precision is very important for effective calibration maintenance and calibration transfer.

The FTIR spectrometer subsystem must achieve certain minimum performance specifications for thermal stability, spectral complexity and modulation efficiency. In real world use of the present invention, ambient temperature and relative humidity will vary with time. Over an ambient temperature operating range of 10 C to 35 C, the FTIR spectrometer must maintain a modulation efficiency of 50% or better. Modulation efficiency is a measure of the useful signal produced by the FTIR spectrometer and is calculated by taking the ratio of the peak interferogram value at zero path difference to the DC value and then multiplying by 100. The maximum theoretical value of modulation efficiency is 100% with typical FTIR spectrometers achieving values in the range of 65% to 95%. FTIR spectrometers with modulation efficiencies below 50% have relatively poorer SNR because of the additional Shot noise from the larger proportion of non-signal bearing DC light falling on the photodetector.

In addition to maintaining modulation efficiency at or above 50% over the ambient temperature operation range, the FTIR spectrometer's change in percent transmittance (% T) at wavelengths between 1.2 and 2.5 microns (8000 to 4000 cm$^{-1}$) should not exceed 2% per degree Celsius. This maximum temperature sensitivity is necessary to preserve the glucose net analyte SNR and to simplify calibration maintenance.

The spectral shape changes induced by thermal drift of the FTIR spectrometer should be simple in shape such that they do not significantly degrade the glucose net analyte signal. One method of quantifying thermal drift for the FTIR subsystem and/or the entire system is to place the device in a temperature controlled chamber and then measure spectra from a stable reference sample, such as an integrating sphere, as a function of time and temperature change in the chamber. A principle components analysis can be performed on the resulting absorbance spectra from the experiment and 99.99% of the variance due to thermal changes should be explained in the first 5 eigen vectors from the principle components analysis. In addition, the % T change with temperature can be calculated from the data set, and the calculated temperature coefficient should be 2% per degree Celsius or less.

As previously stated, the FTIR output beam 245 is sent to a condensing optical element or elements 244 that focus the light onto a NIR sensitive detector. The condensing element or elements 244 can be refractive and/or reflective in nature. Examples of NIR detectors that are sensitive in the spectral range of 1.2 to 2.5 μm include InGaAs, InAs, InSb, Ge, PbS, and PbSe. In the art, non-invasive glucose monitors have been described that utilize standard and extended range InGaAs detectors that are sensitive from 1.2 to 1.7, 1.9 or 2.1 μm. In addition, liquid nitrogen cooled InSb detectors have been used. Also, PbS and PbSe detectors have been used. The present invention is unique in that it utilizes a thermo-electrically cooled, extended range InGaAs detector that is sensitive to light in the 1.2 to 2.5 μm range. The 2.5 μm, extended range InGaAs detector has low Johnson noise and, as a result, allows Shot noise limited performance for the photon flux emanating from the illumination/tissue sampler/FTIR spectrometer subsystems. The extended InGaAs detector has peak sensitivity in the 2.0 to 2.5 μm spectral region where three very important glucose absorption peaks are located. Unlike the liquid nitrogen cooled InSb detector, the thermo-electrically cooled, extended range InGaAs is practical for a commercial product. Also, this detector exhibits over 120 dbc of linearity in the 1.2 to 2.5 μm spectral region.

Any photodetector may be used with the present invention as long as the given photodetector satisfies basic sensitivity, noise and speed requirements. A suitable photodetector must have a shunt resistance greater than 6000 ohms, a terminal capacitance less than 6 nano farads and a minimum photosensitivity of 0.15 amps per watt over the 1.2 to 2.5 micron spectral region. In addition, the photodetector must have a cut-off frequency greater than or equal to 1000 hertz. The shunt resistance of the photodetector defines the Johnson or thermal noise of the detector. The Johnson noise of the detector must be low relative to the photon flux at the detector to ensure Shot noise limited performance by the detector. The terminal capacitance governs the cut-off frequency of the photodetector and may also be a factor in the high frequency noise gain of the photodetector amplifier. The photo sensitivity is an important factor in the conversion of light to an electrical current and directly impacts the signal portion of the SNR equation.

The optical interferogram is converted to an electrical signal by the detector and this signal is received by the data acquisition subsystem 500. The data acquisition subsystem 500 amplifies and filters the electrical signal from the detector and then converts the resulting analog electrical signal to its digital representation with an analog to digital converter. The analog electronics and ADC must support the high SNR and linearity inherent in the interferogram. In order to preserve the SNR and linearity of the interferogram, the data acquisition subsystem 500 supports at least 100 dbc of SNR plus distortion. The data acquisition subsystem 500 produces a digitized interferogram that has uniform spatial displacement between samples. The data acquisition subsystem 500 also receives the reference laser signal from the FTIR spectrometer subsystem 400. Both the NIR signal and the reference laser are digitized by a 24-bit delta-sigma ADC operated at 96 kilohertz. The digital output of the ADC is processed by a signal processor to produce an interferogram that is sampled at constant spatial intervals. The interferograms are passed to the embedded computer subsystem 600 for further processing, as discussed below. Traditionally, the zero crossings of the reference laser are utilized to mark constant spatial intervals for sampling of the interferogram. The zero crossings of the reference laser are spaced at intervals equal to half the wavelength of the monochromatic light emitted by the laser.

Further, the data acquisition subsystem 500 utilizes a constant time sampling, dual channel, delta-sigma analog-to-digital converter (ADC) to support the SNR and photometric accuracy requirements of the present non-invasive glucose measurement. In preferred embodiments, the delta-sigma ADC utilized supports sampling rates of over 100 kHz per channel, has a dynamic range in excess of 117 dbc and has total harmonic distortion less than −105 dbc.

There are other types of data acquisition systems for the FTIR spectrometer and photodetector that are well known in the art and could be employed in the present invention if they provide the following performance characteristics for constant spatial sampling, dynamic range, SNR, harmonic distortion and sampling speed. There is an allowable error in determining the constant spatial sampling intervals of the interferogram, and the spatial sampling interval determination must have a maximum spatial sampling jitter of +/−25 nanometers in order to preserve a SNR of 100 dbc at 1.2 microns (8000 cm$^{-1}$). Levels of spatial sampling jitter greater than +/−25 nanometers will introduce frequency modulation artifacts into the spectral and will degrade the glucose net analyte signal. In addition, the data acquisition subsystem must support a dynamic range of at least 100 dbc, a SNR of 90 dbc and have total harmonic distortion less than 90 dbc. Finally, the ADC of the data acquisition subsystem must be able to sample at speeds of 5,000 samples per second or greater in order to support a minimum FTIR moving mirror scanning speed of 0.25 centimeters per second.

The constant time sampling data acquisition subsystem 500 has several distinct advantages over the more traditional methods of acquiring interferograms from an FTIR spectrometer. These advantages include greater dynamic range, lower noise, reduced spectral artifacts, detector noise limited operation and simpler and less expensive analog electronics. In addition, the constant time sampling technique improves the vibration immunity of the FTIR because it can digitally compensate for delay mismatches between the laser reference and infrared detectors and can back out the non-ideal aspects of the electronics' transfer function. The main disadvantages of the constant time sampling technique are the increased computational and memory requirements necessary to translate the constant time samples of the interferogram to constant spatial samples. With the use of a high performance digital signal processor (DSP), the additional computation and memory requirements are easily outweighed by the performance enhancements of the constant time sampling technique.

The data acquisition subsystem passes the digitized, constant spatially sampled interferograms to the embedded computer subsystem 600 for further processing. The embedded computer subsystem 600 converts the stream of interferograms to single beam spectra by windowing the interferogram, performing phase correction of the windowed interferogram and then taking the Fourier transform of the windowed and phase corrected interferogram. Either Mertz or power phase correction methods may be used. The power phase correction method is simpler to implement, but results in noise that has non-zero mean and is larger in magnitude by a factor of 1.414. The Mertz phase correction method is more complicated but produces noise with zero mean and does not inject noise from the imaginary portion of the complex spectrum. The Mertz method results in spectra with higher photometric accuracy, however, when using multivariate analysis techniques, both phase correction methods result in equivalent prediction performance.

After converting the interferograms to single beam spectra, the embedded computer system will preferably check the single beam spectra for outliers or bad scans. An outlier sample or bad scan is one that violates the hypothesized relationship between the measured signal and the properties of interest (i.e., noninvasive measurement of glucose concentration in human tissue). Examples of outlier conditions include conditions where the calibrated instrument is operated outside of the specified operating ranges for ambient temperature, ambient humidity, vibration tolerance, component tolerance, power levels, etc. In addition, an outlier can occur if the composition or concentration of the sample is different than the composition or concentration range of the samples used to build the calibration model. Any outliers or bad scans will be deleted and the remaining good spectra are averaged together to produce an average single beam spectrum for the measurement. The average single beam spectrum is then preferably converted to absorbance by taking the negative base 10 logarithm (log 10) of the spectrum. The absorbance spectrum is then preferably scaled by a single beam spectrum to renormalize the noise. The resulting scaled absorbance spectrum will then have calibration maintenance and/or calibration transfer algorithms applied to it. Calibration maintenance techniques are discussed in detail below and in commonly assigned U.S. patent application Ser. No. 09/832,608, filed on the same date herewith and entitled "Optically Similar Reference Samples and Related Methods for Multivariate Calibration Models Used in Optical Spectroscopy", the disclosure of which is incorporated herein by reference. Calibration transfer techniques are disclosed in commonly assigned U.S. patent application Ser. No. 09/563,865, filed May 3, 2000, entitled "Method and Apparatus for Spectroscopic Calibration Model Transfer", the disclosure of which is incorporated herein by reference. Finally, a tailoring algorithm such as that disclosed in U.S. Pat. No. 6,157,041 is applied to the spectrum to remove inter-patient variation. After the tailoring step, outlier detection can be performed on the spectrum to check the consistency of the spectrum with the spectra used to generate the multivariate calibration. If the spectrum is consistent with the multivariate calibration spectra, final regression coefficients of the calibration model are applied to the spectrum to produce a glucose prediction. In preferred embodiments, the glucose concentration value from the tailoring spectrum is added to the predicted glucose value to produce the actual glucose concentration for the subject.

To better appreciate the benefits afforded by the calibration maintenance subsystem 300, it is useful to analytically review the problem at hand. The problem solved by the calibration maintenance subsystem is the difficulty in maintaining a multi-wavelength calibration model for quantitatively measuring the concentration of analytes whose spectral absorption is much smaller than that of the gross sample spectrum. The cause of the failure of a spectrally dissimilar reference sample to maintain calibration under these conditions can be described analytically as shown below.

It has been shown in the literature that photometric inaccuracies will be present even in an ideal instrument of finite resolution where all sources of non-linearity (detector response, stray light, etc.) have been removed. See, for example, R. J. Anderson and P. R. Griffiths, *Analytical Chemistry*, Vol. 47, No. 14, December 1975; and R. J. Anderson and P. R. Griffiths, *Analytical Chemistry*, Vol. 50, No. 13, November 1978. This inherent inaccuracy is caused by the finite resolution of the instrument (grating spectrometer or FT interferometer) because a spectrum produced by an instrument with finite resolution will be the true sample spectrum convolved with the instrument line shape (ILS) (for a grating spectrometer, the ILS is a function of the entrance and exit slit widths and for an FT interferometer, the ILS is a function of the instrument self-apodization and the apodization function used in performing the Fourier transform). One can think of the convolution process as a distortion of the true spectrum at a particular wavenumber that is dependent on all other spectral intensities within the spectral bandpass of the instrument. Mathematically this can be written as Equation (10):

$$T^a(\bar{v}_i) = \int_0^\infty \sigma(\bar{v} - \bar{v}_i) e^{-K(\bar{v})l} d\bar{v} \qquad \text{Eq. (10)}$$

where $T^a(\bar{v}^i)$ is the measured (or apparent) transmission at a particular optical frequency, $\bar{v}_1$, a defines the ILS (or apodization), $K(\bar{v}_i)$ is the absorption coefficient of the species being observed and l is the pathlength through the sample. A conclusion drawn from the Griffiths paper is that this apodization induced distortion causes significant deviations from Beer's law when the true absorbance of a peak exceeds 0.7 AU.

The referenced literature also shows, and it can be inferred from Equation (10), that deviations from Beer's law are also a function of the instrument resolution relative to the narrowness of the spectral line being measured. A quantity called the resolution parameter, $\rho$, is defined as the ratio of the instrument resolution, R, to the full-width-half-height (FWHH) of the spectral band of interest as set forth by Equation (11):

$$\rho = R/FWHH \qquad \text{Eq. (11)}$$

The effect of $\rho$ on photometric accuracy can be understood in the limit by examining Equation (10). If the ILS is thought of as a Dirac-delta or impulse function (i.e., perfect instrument resolution), then the ILS convolution in Equation (1) yields the absorbance term independent of ILS, in other words the true absorbance spectrum is measured if the instrument operates with infinite resolution. On the other hand, if the absorbance term is thought of as a delta function, we are left with only the ILS centered at the discrete wavelength where the absorption line occurs. One can then summarize from the referenced literature that photometric inaccuracy due to apodization is a function of both $\rho$ and the spectral absorbance of the sample as set forth in Equation (12):

$$\text{Error} = f\{\rho, A^\tau(\bar{v})\} \qquad \text{Eq. (12)}$$

where $A^\tau(\bar{v})$ is the true absorbance of all absorbers in the sample.

It will be shown below that when there are different absorbers in the sample and background (for example, liquid water, glucose and water vapor in the sample and only water vapor in the background), the background usually does not capture a system perturbation in the same way that the sample will record the same perturbation. The strategy for using a background in spectroscopy is to capture and correct for instrumental or environmental variations so that the true absorbers in the sample can be identified. If the coefficients of absorption are included for all absorbers in the system, Equation (10) can be rewritten to represent the measured transmission of any sample in any environment. For the particular case of glucose in water in the presence of water vapor, Equation (10) becomes Equation (13):

$$T_s^A(\bar{v}_i) = \int_0^\infty \sigma(\bar{v} - \bar{v}_i) e^{-K_l(\bar{v})l_l} e^{-K_g(\bar{v})l_g} e^{-K_w(\bar{v})l_w} e^{-K_v(\bar{v})l_v} \qquad \text{Eq. (13)}$$

where the subscript "I" represents instrument, "g" represents glucose, "w" represents liquid water and "v" represents water vapor present in the measuring environment. A typical background sample spectrum containing no glucose or water would be written as Equation (14):

$$T_b^A(\bar{v}_i) = \int_0^\infty \sigma(\bar{v} - \bar{v}_i) e^{-K_l(\bar{v})l_l} e^{-K_v(\bar{v})l_v} \qquad \text{Eq. (14)}$$

where the background spectrum measures the instrument absorbance and the water vapor absorbance. The background corrected sample spectrum would be written as Equation (15):

$$\frac{T_s^A(\bar{v}_i)}{T_b^A(\bar{v}_i)} = \frac{\int_0^\infty \sigma(\bar{v} - \bar{v}_i) e^{-K_l(\bar{v})l_l} e^{-K_g(\bar{v})l_g} e^{-K_w(\bar{v})l_w} e^{-K_v(\bar{v})l_v}}{\int_0^\infty \sigma(\bar{v} - \bar{v}_i) e^{-K_l(\bar{v})l_l} e^{-K_v(\bar{v})l_v}} \qquad \text{Eq. (15)}$$

As in Equation (10), the spectral intensity at each optical frequency depends on the spectral intensity of the adjacent frequencies measured by the instrument, the absorption terms for the instrument $e^{-K_l(\bar{v})l_l}$ and the water vapor $e^{-K_w(\bar{v})l_v}$ do not cancel in Equation (15), resulting in a background corrected spectrum that is not equal to the true absorbance spectrum of the measured analytes. The only way these terms will ever cancel is if all other absorption terms that are not common to both sample and background are negligible or do not vary with optical frequency. Equation (15) can be expanded further to encompass any instrumental or environmental perturbation from the calibration state as set forth by Equation (16):

$$\frac{T_{s+\Delta}^A(\bar{v}_i)}{T_{b+\Delta}^A(\bar{v}_i)} = \frac{\int_0^\infty \sigma(\bar{v} - \bar{v}_i) e^{-K_l(\bar{v})l_l} e^{-K_g(\bar{v})l_g} e^{-K_w(\bar{v})l_w} e^{-K_v(\bar{v})l_v} e^{-K_\Delta(\bar{v})l_\Delta}}{\int_0^\infty \sigma(\bar{v} - \bar{v}_i) e^{-K_l(\bar{v})l_l} e^{-K_v(\bar{v})l_v} e^{-K_\Delta(\bar{v})l_\Delta}} \qquad \text{Eq. (16)}$$

where the subscript $\Delta$ represents the absorption due to the perturbation. Maintenance of calibration could be achieved using any reference sample if the ratio in Equation (16) were equal to the ratio in Equation (15). However, as long as the unknown sample and reference sample have different spectral characteristics, Equation (16) will never identically equal Equation (15). The two equations become more similar as the reference sample begins to absorb more like the prediction sample.

In summary, a similar background is required when the system perturbation is not well modeled and the perturbation is not negligible in magnitude compared to the absorbers in the prediction sample, or when the spectral resolution (full width at half height) of the perturbation is much less than the instrument resolution. Another way to write this requirement is in terms of the final regression coefficients from a multivariate calibration model acting on the spectrum of the unknown sample. This can be written as Equation (17):

$$\bar{F} \cdot (\bar{S}_o + \bar{S}_{NL} + \bar{\epsilon}) \Rightarrow \bar{F} \cdot \bar{S}_{NL} >> \bar{F} \cdot \bar{\epsilon} \qquad \text{Eq. (17)}$$

where $\bar{F}$ represents a vector of final regression coefficients, $\bar{S}_o$ represents the true spectrum, $\bar{S}_{NL}$ represents the distorted, or non-linear, part of the measured spectrum due to the finite resolution of the instrument and $\bar{\epsilon}$ represents the spectral error due to sources of random error. In other words, the product of the final regression coefficients and the non-linear portion of the measured spectrum caused by a system perturbation should be much less than the product of the final regression coefficients and the random error present in the measured spectrum so that the error term due to the distorted part of the spectrum is small and prediction performance is maintained.

There are several different types of instrumental and environmental variation which may affect the prediction capability of a calibration model. It is possible, and highly desirable to reduce the magnitude of the effect of instrumental and environmental variation by incorporating this variation into the calibration model. It is difficult, however, to span the entire possible range of instrument states during the calibration period. System perturbations can result in the instrument being operated outside the space of the calibration model. Measurements made while the instrument is in an inadequately modeled state will exhibit prediction errors which render the measurement useless. In the case of in vivo optical measurements, these types of errors may result in erroneous medical information being used for the treatment of patients. These errors are obviously unacceptable in a commercial device.

Some examples of problematic instrument and environmental variation include, but are not limited to: changes in the levels of environmental interferents such as water vapor or $CO_2$ gas, changes in the alignment of the instrument's optical components, fluctuations in the output power of the instrument's illumination system, and changes in the spatial and angular distribution of the light output by the instrument's illumination system. It will be shown through both simulated and empirical results that a spectrally similar background sample provides improved capability to correct for these types of variations.

Correcting for any of the classes of instrument and environmental variation requires that the background sample have matched spectral absorption features with the sample of interest. It has already been shown mathematically that the finite instrument resolution causes the effect of different instrument states to depend on the spectral absorption characteristics of the sample (Equation (16)). Another way of stating this problem is that the optical effects of instrument and environmental variation should ideally be identical in both the background sample and the sample of interest. Taking the derivative of Equation (13) with respect to water vapor absorption yields Equation (18):

$$\frac{dT_s^A(\overline{v}_i)}{dK_v(\overline{v})} = \int_0^\infty -I_v \sigma(\overline{v}-\overline{v}_i) e^{-K_l(\overline{v})l_l} e^{-K_g(\overline{v})l_g} e^{-K_w(\overline{v})l_w} e^{-K_v(\overline{v})l_v} d\overline{v} \qquad \text{Eq. (18)}$$

It is apparent from Equation (18) that the spectrum of water vapor is modified by the spectral shape of all compounds in the sample. This relationship holds true for any system perturbation which causes a change in the optical appearance of a sample's spectrum.

Figure 34:
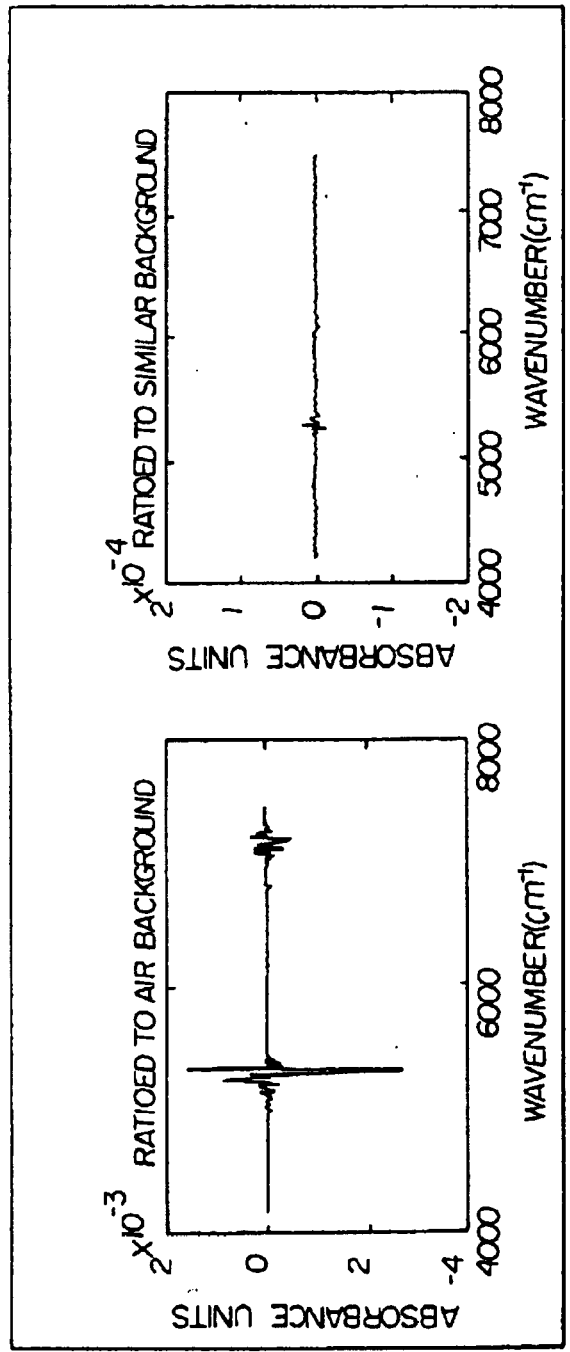
FIG. 34 shows two graphs of spectral residuals comparing a conventional air background to a similar background.

Simulated results are presented for the effects of water vapor level variation on the in vitro measurement of glucose in reflectance using scattering media. Actual spectra from 98 glucose solution samples were collected using an FTIR spectrometer operated at 16 cm$^{-1}$ resolution. The samples contained variable levels of scattering media to simulate optical pathlength distributions similar to those seen in living tissue. For comparison purposes, spectra from two different types of background samples were also collected: a similar background with matched optical properties and an air background (i.e., an integrating sphere placed over the reflectance sampler). High-resolution water vapor spectra (obtained at 1 cm$^{-1}$) were then artificially added to the solution and background spectra in order to simulate varying water vapor levels. Simulations were run on the resulting spectra in order to model the effects of finite instrument resolution on the added interferents. The sample spectra were then ratioed to the background sample spectra in an attempt to remove the effects of the varying water vapor levels. FIG. 34 shows the residual spectral effects after this background correction was performed. The two plots in FIG. 34 show the remaining spectral differences when the ratioed spectra with added water vapor are subtracted from the original ratioed spectra without added water vapor. As can be seen in the figure, the spectrally similar background reduces the effects of the water vapor interferent by a significant amount. A calibration developed at a constant water vapor was used to predict on the sample spectra As stated above, the sample spectra were ratioed against a similar background with matched optical properties and an air background. The prediction errors for the sample data with the air background ratio were inflated over the sample spectra with a similar background by approximately 40 mg/dl using a calibration model with 20 factors. This simulation clearly demonstrates the advantage of using a similar background for correcting for even simple system perturbations.

Many of the types of instrument variation involve interactions with the sampling geometry of the sample. These types of instrument variation include changes in alignment of optical components and changes in angular and spatial distribution of the output light from the instrument's illumination system. These types of variations may be caused by a number of physical mechanisms, including: aging of optical mounts, thermally induced mechanical deformations of optical mounts, aging of light sources, or variations in routinely replaced components such as light bulbs. In order to be effective, the background sample must preserve the same mapping of angular and spatial distribution of light as the sample of interest. This requires that the background sample interact with the sampling optics of the instrument in a manner that mimics the interaction of the sampling optics with the sample of interest.

An additional constraint which is generally required for successful calibration maintenance is that the overall intensity of light seen at the optical detector elements be closely matched for both the background sample and the sample of interest. This constraint helps to correct for non-linearities in the instrument's optical measurement characteristics. Again, this constraint is included in the overall definition of similar spectral radiance.

Figure 35:
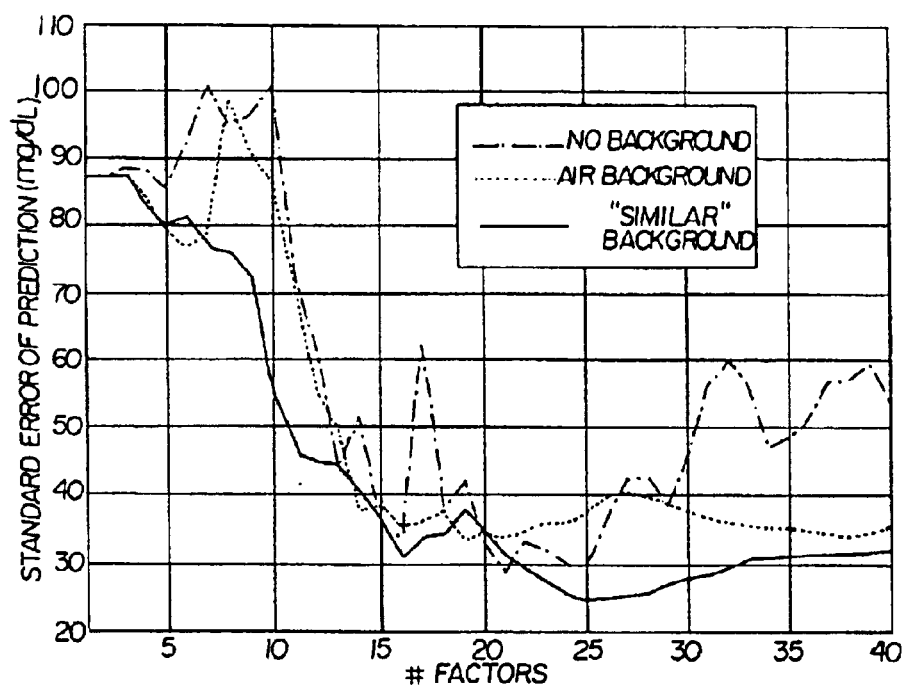
FIG. 35 shows a graph of standard error of prediction comparing no background, a conventional air background, and a similar background in the presence of instrument and environmental variation.
Figure 36:
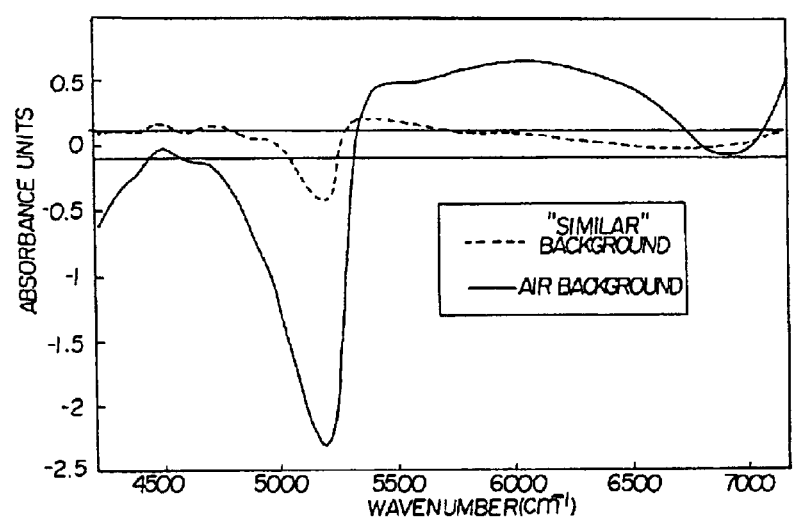
FIG. 36 shows a graph of the spectral differences between the mean human tissue spectrum and two different backgrounds, namely a conventional air background and a similar background.

Empirical results are presented for an actual, in vivo study measuring blood glucose concentrations non-invasively. The study was intentionally designed to include several of the types of instrument and environmental variation previously discussed herein. Specifically, ambient relative humidity, ambient temperature, and illumination power were all varied during the prediction phase of the study. This study was intended as a proof of concept for using a similar background reference sample for calibration maintenance. The study was limited to five subjects over a period of two days. Prediction errors were determined by comparing non-invasive results to standard capillary blood glucose reference measurements. FIG. 35 demonstrates the superior ability of the similar background to maintain the prediction performance of the calibration in the presence of instrument and environmental variation by generating a lower standard error of prediction and by generating the smoothest decreasing SEP curve. FIG. 36 shows the spectral differences between the mean human tissue spectrum and the two different background sample types being tested in the study.

Figure 37:
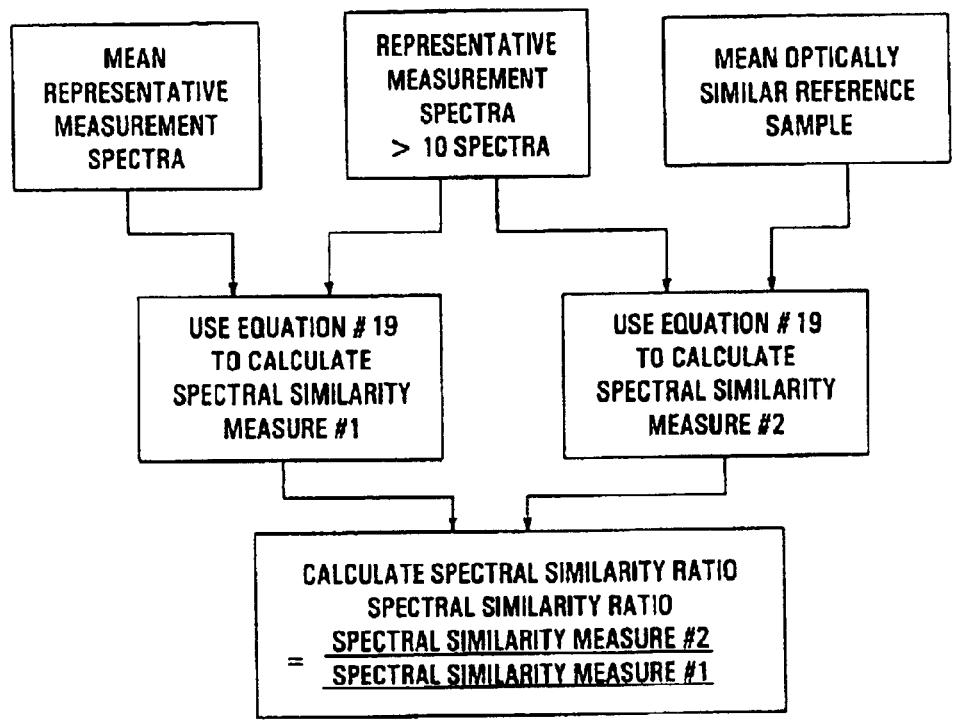
FIG. 37 is a flowchart illustrating the steps used in quantifying spectral similarity.

Refer now to FIG. 37 which illustrates a flowchart for determining spectral similarity. The spectral similarity of an optically similar reference sample to the test sample of interest may be quantified with respect to spectral absorbance, mapping of input to output light spatial distribution, and mapping of input to output light angular distribution.

There are two metrics that may be used to calculate the similarity of a particular background sample to the sample of interest with respect to spectral absorbance. The first involves comparing the optically similar reference sample in question to the test samples, typically tissue spectra, where all of the background and tissue spectra were collected near in time, as set forth in Equation 19:

$$\text{Spectral Similarity} = \frac{\sum_{i=1}^{I}\left(\sum_{j=1}^{J}(X_{ij} - z_i)^2\right)}{I} \quad \text{Eq. (19)}$$

where X is a set of tissue pseudo-absorbance spectra and z is any mean background pseudo-absorbance spectrum for the time in question. (The pseudo-absorbance spectrum is defined in Equation 20). I refers to the total number of data points collected in the wavelength region of interest (or the total number of discrete wavelengths chosen for analysis), and J refers to the total number of tissue spectra collected in this period of time. The average value of the spectrum should be subtracted from all wavelengths before calculating the metrics. This step ensures that the spectral shapes of the background and tissue are correctly compared without being influenced by a uniform, DC energy offset or baseline shift.

$$\text{Pseudo-absorbance} = -\log_{10}(I) \quad \text{Eq. (20)}$$

where I is a single beam intensity spectrum.

Quantifying the degree of spectral similarity can be done through a straightforward process involving a comparison between the spectra in which the analyte is to be measured and the optically similar reference sample. The flowchart of FIG. 37 summarizes this process. The process involves the following steps:

Step #1: Define or establish the representative measurement sample. A representative measurement sample is a sample that is representative of samples on which the optical measurement system will be making subsequent measurements. If the application is a single patient with diabetes, then a representative measurement sample would be a sample at the sampling location on that patient. If the application group is a heterogeneous group of subjects, then the representative measurement samples would be an appropriate group of subjects on which the monitor would be subsequently used. If the measurement group were other sub-populations of subjects, then the representative measurement samples would be obtained from the sub-population. For example, in patients with renal disease, the representative measurement population would be patients with renal disease.

Step #2: Obtain spectral measurements from the representative measurement samples. In all cases, multiple measurements with reinsertions of the tissue into the sampling device should be made. In the case of a single subject application, at least ten spectral measurements should be made. In the case of a heterogeneous patient population, the representative measurement samples should be a reflection of the subjects that will subsequently use the monitor. In the example below, 30 subjects of varying ages, gender, ethnicity and body mass index were used. The spectral measurements should be made in a manner consistent with use of the monitoring device. These spectra are hereafter referred to as the representative measurement spectra.

Step #3: Calculate a mean pseudo-absorbance spectrum from the spectra obtained from the representative measurement samples. The resulting spectrum is hereafter referred to as the mean representative measurement spectrum.

Step #4: Obtain spectral measurements from the optically similar reference sample. In all cases, multiple insertions and measurements of the optically similar reference sample should be made. It is preferred that at least 10 measurements should be made. These spectra are hereafter referred to as the optically similar reference sample spectra.

Step #5: Calculate a mean pseudo-absorbance spectrum from the optically similar reference sample spectra. The resulting spectrum is hereafter referred to as the mean optically similar reference spectrum.

Step #6: Use the representative measurement spectra and the mean representative measurement spectrum with Equation (19) to calculate a spectral similarity value. The resulting value will hereafter be referred to as the spectral similarity measure #1.

Step #7: Use the representative measurement spectra and the mean optically similar reference spectrum with Equation (19) to calculate a spectral similarity value. The resulting value will hereafter be referred to as the spectral similarity measure #2.

Step #8: Ratio the two spectral similarity values to obtain a spectral similarity ratio.

$$\text{Spectral similarity ratio} = \frac{\text{Spectral Similarity Measure \#2}}{\text{Spectral Similarity Measure \#1}}$$

Equation (19) is a mean sum of squares (SS) metric, and it may be calculated for different wavelength regions. It may be calculated for a continuous spectral region, for discrete wavelengths, for combinations of two or more discrete wavelengths (which may or may not have been found using a variable selection algorithm), or for selected regions of a spectrum.

Table 5 below shows the values that were calculated for Equation (19) for a representative group of subjects for three levels of similarity: acceptable, preferred, and ideal. The spectral regions and discrete wavelengths for which these values were calculated are also indicated in the table. The discrete variables used in this case are glucose important wavelengths and are specified in Table 6. The more similar the background is to the tissue spectra, the smaller the SS value becomes. Table 7 shows the same spectral similarity metrics when the representative sample is a single subject.

TABLE 5

| | | Spectral Similarity Ratio | | |
|---|---|---|---|---|
| Level of Similarity | Example Background Sample | Full Spectrum (4,200 cm$^{-1}$– 7,200 cm$^{-1}$) | Discrete Variables | Absorbance Troughs (4,440 cm$^{-1}$–4,800 cm$^{-1}$ & 5,400 cm$^{-1}$–6,400 cm$^{-1}$) |
| Acceptable | Scattering Solutions | 30 | 30 | 30 |
| Preferred | Transmission Cell | 10 | 10 | 10 |
| Ideal | Meat, Subject Spectrum | 1 | 1 | 1 |

TABLE 6

Glucose-important variables (cm$^{-1}$) used in spectral similarity calculations

| 4196 | 4451 | 4883 | 5369 | 5731 | 6163 | 6696 |
| 4227 | 4459 | 4922 | 5392 | 5755 | 6187 | 6935 |
| 4273 | 4497 | 5014 | 5454 | 5765 | 6287 | 6973 |

TABLE 6-continued

Glucose-important variables (cm$^{-1}$) used in spectral similarity calculations

| 4281 | 4528 | 5091 | 5469 | 5809 | 6318 | 7004 |
|------|------|------|------|------|------|------|
| 4304 | 4559 | 5176 | 5477 | 5839 | 6349 | 7043 |
| 4320 | 4613 | 5230 | 5515 | 5893 | 6449 | 7066 |
| 4335 | 4690 | 5269 | 5585 | 5924 | 6472 | 7205 |
| 4366 | 4775 | 5299 | 5623 | 5947 | 6557 |      |
| 4389 | 4829 | 5315 | 5662 | 6001 | 6595 |      |
| 4436 | 4860 | 5338 | 5701 | 6094 | 6673 |      |

TABLE 7

| | | Spectral Similarity Ratio | | |
|---|---|---|---|---|
| Level of Similarity | Example Background Sample | Full Spectrum (4,200 cm$^{-1}$–7,200 cm$^{-1}$) | Discrete Variables | Absorbance Troughs (4,440 cm$^{-1}$–4,800 cm$^{-1}$ & 5,400 cm$^{-1}$–6,400 cm$^{-1}$) |
| Acceptable | Scattering Solutions | 1500 | 1500 | 7500 |
| Preferred | Transmission Cell | 1000 | 1000 | 2500 |
| Ideal | Mean Subject Spectrum | 1 | 1 | 1 |

If an analyte is to be determined, it is helpful if the background matches different regions and/or discrete wavelengths of the spectrum that are important in the determination. In other words, if spectral region A is important in determining the analyte, then the background should match the tissue especially well in region A. On the other hand, region A may not be at all important in determining a different analyte, in which case the spectral match would be less important for that region. When an analyte is to be determined, therefore, another metric must also be defined that is specific to the analyte in question, as shown in Equation (21) below.

$$\text{Regression weighted Similarity} = \frac{\sum_{i=1}^{I}\left(\sum_{j=1}^{J}(b_i * X_{ij} - b_i * z_i)^2\right)}{I} \quad \text{Eq. (21)}$$

where b is the regression vector for the analyte being determined, normalized to length one, and the other symbols have the same meanings as in Equations (19) and (20). This regression vector may be calculated via any linear or non-linear regression method, where partial least squares is an example of such a method. It may be thought of as the analyte's calibration model, and it weights the absorbances at different wavelengths based on their importance in predicting the analyte characteristic of interest.

The process for quantifying the degree of spectral match is the same except that Equation (21) is used instead of Equation (19). The 8-step process is the same with a single substitution of the equations. The resulting ratio will hereafter be referred to as the regression weighted spectral similarity ratio.

Table 8 shows results from Equation (21), calculated for a representative group of subjects when the analyte of interest was glucose; however, these values may also be calculated for any component in the sample that is to be determined. It can be seen that the ideal background has a much smaller SS value than the acceptable background, since it is more similar to tissue spectra collected during the same period of time. The more similar the background is, the smaller the SS value will be for Equation (19) or Equation (21) or both, for any spectral region or any combination of regions or any discrete wavelength or combination of discrete wavelengths. Table 9 shows the same spectral similarity metrics when the representative sample is an individual subject. In an analysis where no specific characteristic (e.g., concentration) of the sample is being measured, then Equation (19) is sufficient. When a specific characteristic is to be determined, however, both Equations (19) and (21) maybe evaluated.

If the spectral similarity ratio for the optically similar reference sample value is less than 30, then the optically similar reference sample is to be considered an acceptable optically similar reference sample. If the spectral similarity ratio is less than 10, then the optically similar reference sample is to be considered a preferred optically similar reference sample. If the spectral similarity ratio is less than or equal to 1, then the optically similar reference sample is to be considered an ideal optically similar reference sample. The metrics must be calculated for the analyte being determined and for the wavelengths/wavelength regions being used to ensure the validity of the similarity determination.

TABLE 8

| | | Regression Weighted Spectral Similarity Ratio | | |
|---|---|---|---|---|
| Level of Similarity | Example Background Sample | Full Spectrum (4,200 cm$^{-1}$–7,200 cm$^{-1}$) | Discrete Variables | Absorbance Troughs (4,440 cm$^{-1}$–4,800 cm$^{-1}$ & 5,400 cm$^{-1}$–6,400 cm$^{-1}$) |
| Acceptable | Scattering Solutions | 30 | 30 | 30 |
| Preferred | Transmission Cell | 10 | 10 | 10 |
| Ideal | Mean Subject Spectrum | 1 | 1 | 1 |

TABLE 9

| | | Regression Weighted Spectral Similarity Ratio | | |
|---|---|---|---|---|
| Level of Similarity | Example Background Sample | Full Spectrum (4,200 cm$^{-1}$–7,200 cm$^{-1}$) | Discrete Variables | Absorbance Troughs (4,440 cm$^{-1}$–4,800 cm$^{-1}$ & 5,400 cm$^{-1}$–6,400 cm$^{-1}$) |
| Acceptable | Scattering Solutions | 4500 | 3000 | 9000 |
| Preferred | Transmission Cell | 1500 | 2500 | 3000 |
| Ideal | Mean Subject Spectrum | 1 | 1 | 1 |

The similarity of the mapping function of light spatial distribution and light angular distribution can also be quantified for optically similar reference samples. The preferred method for quantifying the similarity of these properties is to examine the image of the output light beam, which is produced after the light has passed through the sampling optics and the sample of interest. For purposes of this discussion, the light beam is assumed to be circular in cross-section, but the similarity metrics can be extended to any geometry of beam (e.g., the output of a square cross-section light guide). The boundary of the light beam passing through the sample is defined as the points at which the light intensity falls to $1/e^2$ times the peak light intensity.

The image of the output beam is measured using any standard intensity mapping scheme (e.g., scanning a single pixel detector or using a CCD camera) and using a goniometer. This allows both the spatial and angular distributions of the light beam to be determined. Measurements should be made for both the sample of interest and for the similar background being quantified. In order to standardize the calculation for many applications, the image should be divided into approximately one hundred equally sized "bins" (or squares), with ten bins across the diameter of the image. This can be accomplished by either measuring the beam in a ten by ten grid or by sampling at a finer spacing and then averaging the data. The spatial and angular distributions for the sample of interest are then subtracted from the corresponding distributions of the background sample. The resulting images represent the similarity level for the background and the sample of interest. In order to quantify this similarity, all of the data points in the image are put into a vector for easier calculation, and the vector is normalized so that its length equals 1. This is achieved by dividing each data point in the image by the 2-norm ($\|x\|_2$), which is equivalent to the Euclidean distance of the vector.

$$\|x\|_2 = \left( \sum_{i=1}^{n} |x_i|^2 \right)^{1/2} \qquad \text{Eq. (22)}$$

where x is the vector of the difference image and n is the number of data points in that vector.

The normalization step ensures that the magnitude of every difference-image is comparable. Following the normalization step, the standard deviation of the normalized image vector is calculated, and this metric is an indication of how similar the background and sample images are. Table 9 shows the standard deviations that are ideal, preferred and acceptable for the spatial distribution of similar backgrounds. Table 10 shows the same metrics for angular distribution.

TABLE 10

| Level of Similarity | Spatial Similarity Metric (Stardard Deviation) |
| --- | --- |
| Acceptable | 0.079 |
| Prererred | 0.052 |
| Ideal | 0 |

TABLE 11

| Level of Similarity | Angular Similarity Metric (Standard Deviation) |
| --- | --- |
| Acceptable | 0.051 |
| Preferred | 0.036 |
| Ideal | 0 |

As stated previously, the optically similar reference sample is used to capture the current instrument state such that the effect of instrumental and environmental variation on prediction capability can be eliminated. There are several different methodologies by which the reference spectrum can be used to correct for instrumental and environmental variation. These spectral correction methods include, but are not limited to those described below.

These correction methodologies can be classed into two broad categories: methods which modify the spectrum of the test sample and methods which modify the calibration model. The simplest and preferred method modifies the spectrum of the sample of interest by subtracting the optically similar reference spectrum in absorbance space. The reference spectrum may be the most recently collected optically similar reference spectrum, or it may be an averaged spectrum containing information from several background samples collected at different points in time. One preferred method of averaging is to exponentially time weight the background reference spectra and average them together. The exponentially time weighted method allows for the optimization of achieving high signal-to-noise-ratio correction data and capturing the current instrument state.

The second class of background correction methodologies consists of actually modifying the multivariate calibration model. One simple method is to simply include the reference spectra with the original calibration samples and rerun the regression algorithm on the combined data set. A preferred method is to include only the spectral variation from the background reference sample in the calibration model. This method consists of taking multiple background reference samples during the calibration period, finding the mean of the background reference sample spectra collected during the calibration period, subtracting (in absorbance space) this mean background reference spectrum from subsequent background reference spectra collected prior to making an actual prediction, adding this spectral difference back to the calibration samples, and rerunning the regression algorithm to create an updated calibration model. In an alternative method, a PCA decomposition is run on the spectral differences seen in the background and a limited number of eigenvectors is used to add this spectral variation back to the model.

Referring now to FIGS. 38–55, several embodiments of similar background devices for use in a calibration maintenance subsystem 300 of the present invention are depicted. Each of the similar background embodiments discussed may be used in combination within the present system. These specific backgrounds are intended for applications, such as glucose measurement, in which analyte concentrations are to be measured in vivo using reflection spectroscopy. Specifically, these optically similar reference samples are designed to match the optical properties of tissue at selected wavelengths in the near infrared region including 1.2 to 2.5 $\mu$m (8000 to 4000 wavenumbers). In this optical region, water is the dominant absorbing component contained in the tissue. Each of the following backgrounds is designed to provide multiple optical pathlengths through water in order to mimic the spectrum of living tissue. Based upon Monte Carlo simulations of light propagation through scattering media where the scattering properties match those of tissue, a distribution of pathlengths can be calculated. The results can be defined by a mean pathlength with a standard deviation and skew to the distribution. The distribution skew is toward longer pathlengths. Typically the standard is less than or equal to the mean. For example, if the mean pathlength is 1 mm, then the standard deviation of pathlengths is about 1 mm as well.

In developing and assessing reference samples, is important to have a metric that enables one to rapidly and easily determine if multiple optical pathlengths of water are created by the reference sample. One simple way is to fit the absorbance spectrum of the reference sample with three terms: 1) an offset, 2) a slope with wavenumber, and 3) the pure component of water. The pure component of water is simply the absorbance of water at a fixed pathlength. Mathematically stated:

$$\bar{A}(x) = b_0 + b_1 x + b_2 PC(x) \qquad \text{Eq. (23)}$$

The three fitting parameters are estimated using a least squares fit of the above equation to the absorbance spectrum (which has no instrument line shape in it). Following fitting of the above parameters the spectral residual is determined. The spectral residual is determined by subtracting the above equation from the absorbance spectrum of the reference sample. The final step is to compute the root-mean-squared (RMS) error across the spectrum.

$$\text{Multipath\_RMSError} = \sqrt{\frac{1}{N} \sum_{i=1}^{N} (A_i - \hat{A}_i)^2} \qquad \text{Eq. (24)}$$

The multipath RMS error is greater when multiple pathlengths of water are present in the reference sample. A single pathlength sample will results in a smaller RMS error then a two pathlength sample, etc. A simple threshold value calculated in absorbance units can be used to determine if multiple pathlengths of water are present. The threshold is sensitive to the spectral region used. For, example the threshold would be smaller if the region used for analysis had smaller absorbance bands.

Several novel designs are presented for achieving the multiple water pathlengths required to match the spectrum of tissue. Most embodiments consist of an optical interface (e.g., an MgF$_2$ window) which is highly transmissive in the optical region of interest, an optical sampling compartment containing water, and diffusely reflective or scattering media. For each background design, either experimental or simulated data are presented showing how close a spectral match was achieved between the background and human tissue.

The inventors recognize that in addition to including the dominant absorbing species (e.g., water), the background sample may also include the actual analyte of interest (e.g., glucose, ethanol, urea, etc.). By including various analytes, the background sample may be used as a quality control or calibration sample in addition to its primary use in the maintenance of calibration.

With specific reference now to FIGS. 38 and 39, a cone background device 300 is illustrated in accordance with an embodiment of the present invention. FIG. 38 illustrates representative ray-traces in the cone background device 301 and FIG. 39 illustrates a partial cut-away view of the cone background device 301. Cone background device 301 utilizes a conical geometry in order to help achieve some of the required performance specifications for a background similar to human tissue. It includes an optically transparent cone 330 such as a fused silica cone, a thin layer of a constituent 320 such as water, collagen or lipid, and a diffusing cone 310 which provides approximately Lambertian reflection of the incident radiation.

The cone geometry of device 301 provides excellent stray signal suppression as best seen in the ray trace shown in FIG. 38. The useful signal is transmitted through the hollow portion 340 of the cone, and then through the constituent layer 320. The amplitude of the signal that is reflected back to the collection system without undergoing the desired interaction is reduced significantly due to several Fresnel reflection losses. The useful radiation undergoes a randomized reflection from the diffusing cone 310 surface, and passes back into the inner cone volume 340, either to be collected or to undergo yet another pass through constituent layer 320 and random reflection. FIG. 40 shows a graph of spectral response demonstrating the spectral match between the tissue sample and the cone device 301.

The cone reference sample, as designed, contains a distribution of optical pathlengths through water. This distribution of water pathlengths was confirmed by calculating the multipath RMS error in the manner explained above. The multipath RMS error was calculated over the region of 4200–7200 cm$^{-1}$ and generated a value of 0.18 absorbance units.

Figure 41:
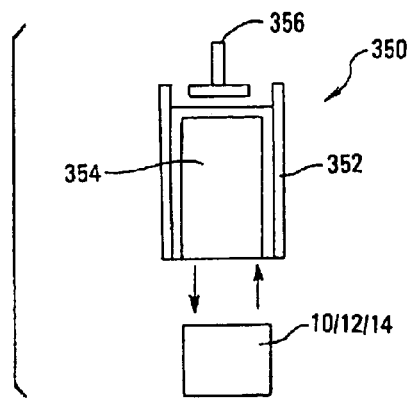
FIG. 41 schematically illustrates a scattering solution background in accordance with an embodiment of the present invention.
Figure 42:
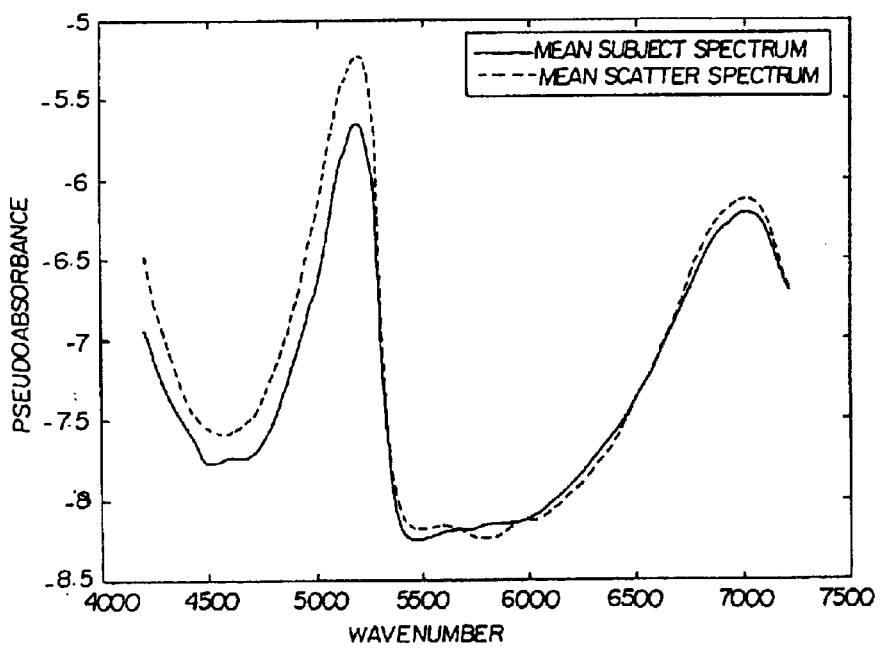
FIG. 42 shows a graph of spectral response demonstrating the spectral match between the tissue sample and the scattering solution background.

Refer now to FIG. 41, which schematically illustrates a scattering solution background device 350 in accordance with another embodiment of the present invention. The scattering solution background 350 includes a container 352 that is at least partially optically transparent adjacent the tissue sampling 12 and collection subsystem 14. The scattering solution background also includes a scattering solution 354. Scattering solution 354 comprises a plurality of reflective beads disposed in a liquid or gel constituent such as water, collagen or lipid. The random pathlength distribution of the scattering solution 354 is provided by the reflective beads, which may comprise, for example, reflecting polystyrene microbeads (0.298 μm diameter, 6600 mg/dl concentration) in aqueous solution. The particle reflectance, size and concentration of the reflective beads in the scattering solution 354 are set in order to create the desired match to tissue for the solution 354. Preferably, the solution 354 is mechanically agitated by agitator 356 in order to prevent settling of the reflective beads. FIG. 42 shows a graph of spectral response demonstrating the spectral match between the tissue sample and the scattering solution background 350.

Figure 43:
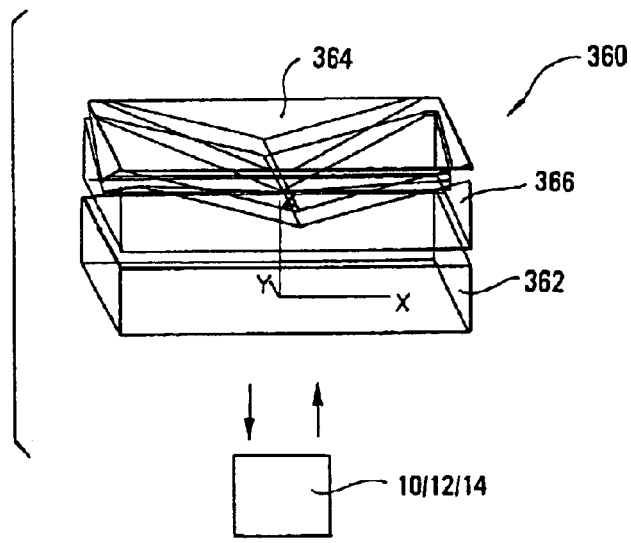
FIG. 43 schematically illustrates a roof background in accordance with an embodiment of the present invention.
Figure 44:
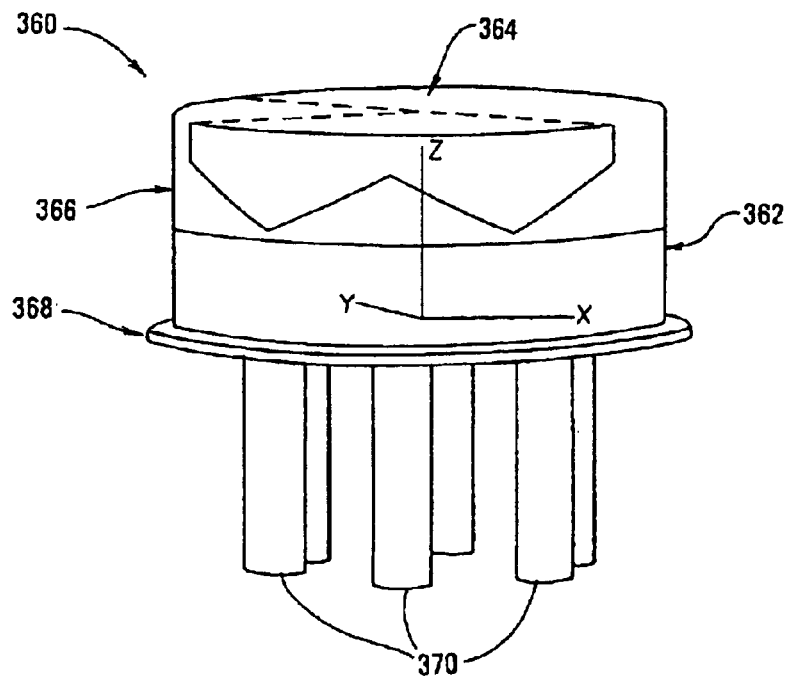
FIG. 44 schematically illustrates an alternative roof background as positioned on a fiber optic sampling array-.

Refer now to FIGS. 43 and 44, which schematically illustrate alternative, roof background devices 360 in accordance with yet another embodiment of the present invention. The roof background devices 360 make use of an optically transparent layer 362 such as a flat window comprising fused silica or MgF$_2$, a roof-like reflective diffuser 364, and a constituent layer 366 disposed therebetween. The optically transparent layer 362 may be used to surround and contain the constituent layer 366. The constituent layer 366 may comprise water, collagen, lipid, or a mixture thereof. The diffuser 364 may include an irregular or otherwise non-planar surface such as roughened aluminum or stainless steel, or Spectralon of the proper reflecting characteristics. Light passes from the tissue sampler 12 through the window 362 and constituent layer 366 to the diffuser 364. After undergoing a random reflection from the diffusing surface, the light passes back through the constituent layer 366 through the window 362 to the collection system 14. FIG. 44 further illustrates the roof background device 360 disposed on a sampler interface 368 to which a cluster of fiber optic bundles 370 is joined. Each fiber optic bundle preferably includes an arrangement of a plurality of input and output fiber optic cables.

Figure 45:
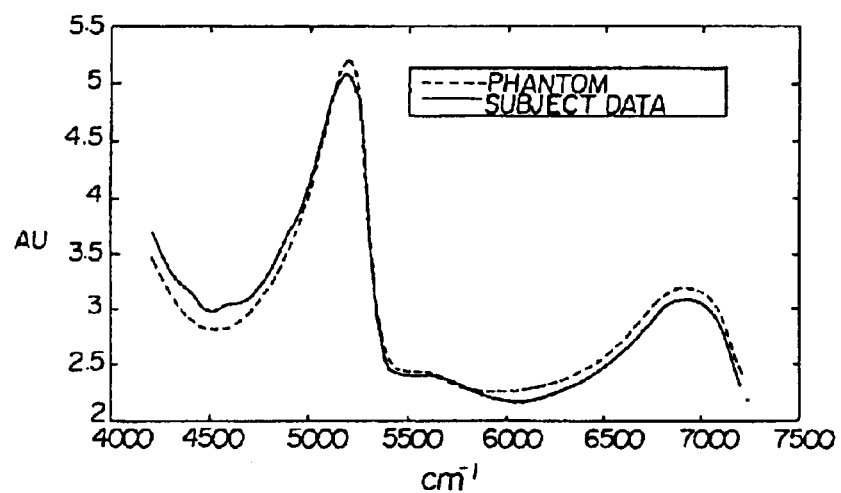
FIG. 45 shows a graph of spectral response demonstrating the spectral match between the tissue sample and the roof background.

The parameters of the device 360 may be adjusted so that the collected light has similar spectral radiance to light that has interacted with tissue. FIG. 45 shows a graph of spectral response demonstrating the spectral match between the tissue sample and the roof background 360. The angles of the diffusing surface and the thickness of the water path were adjusted in simulation to achieve the theoretical result shown in FIG. 45. The spectral response of this system was calculated from the pathlength distribution and the known absorption spectrum of water. It is important to note that the spectral match shown depends on adjusting the mean energy of the background to match that of tissue.

Figure 46:
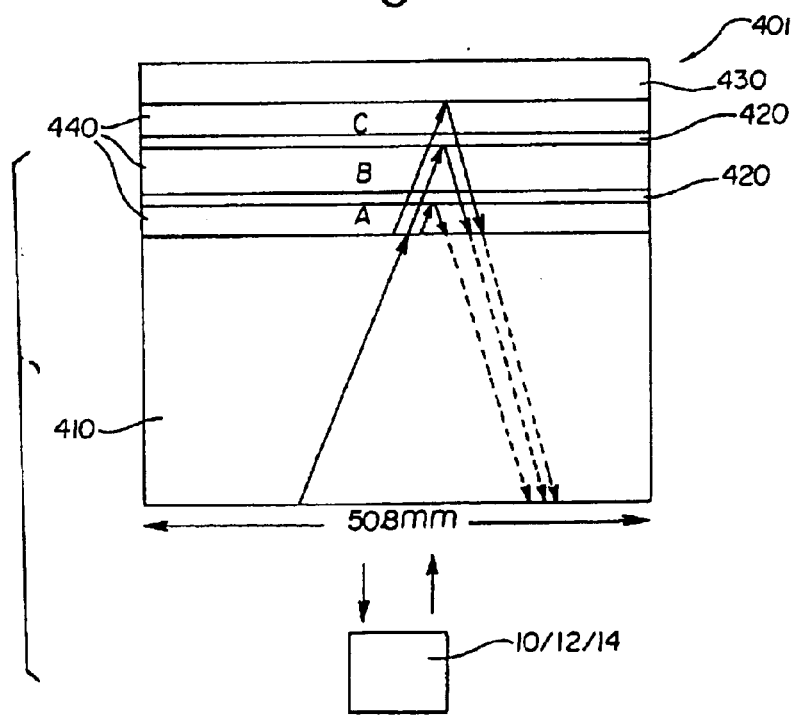
FIG. 46 schematically illustrates a multi-layer background in accordance with an embodiment of the present invention.

Refer now to FIG. 46, which schematically illustrates a multi-layer background device 401 in accordance with a further embodiment of the present invention. The multi-layer background device 401 is based on a match at discrete pathlengths to tissue. The multi-layer device 401 includes an optically transparent window 410 such as an $MgF_2$ window, a plurality of optical splitting layers 420 such as partially reflecting quartz microslides, and a reflecting layer or surface 430 such as a gold mirror. Multiple constituent layers 440, such as water, are disposed between the window, 410, the optically transparent layers 420, and the reflective layer 430. The optically transparent window 410 may be used to surround and contain the constituent layers 440. The diameter of the multi-layer background 400 is chosen to match the output area of the sampling optics for a given device.

Figure 47:
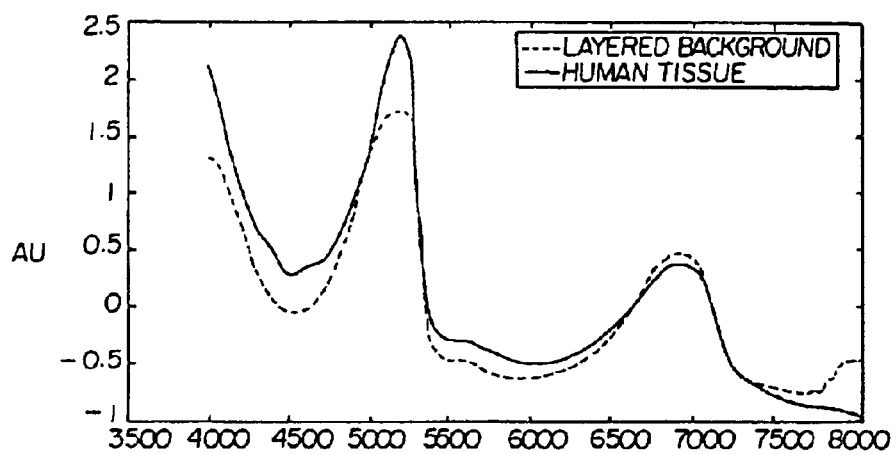
FIG. 47 shows a graph of spectral response demonstrating the spectral match between the tissue sample and the multi-layered background.

Incident light from the tissue sampler 12 is broken up into components with discrete pathlengths by the optical splitting layers 420. The reflectance of the optical splitting layers 420 and the thickness of the constituent layers 440 may be adjusted in order to achieve the proper distribution of pathlengths in the device 401 so that a match to tissue is achieved. FIG. 47 shows a graph of spectral response demonstrating the spectral match between the tissue sample and the multi-layered background 401. For this test, the water layers 440 (labeled A, B, and C) were sized as follows: A=170 $\mu$m, B=205 $\mu$m, and C=150 $\mu$m. The microslide 420 between layer A and B had 4% reflectance, and the microslide 420 between layer B and C had 32% reflectance. The gold mirror 430 had approximately 99% reflectance in the specified wavelength region Refer now to FIG. 48, which schematically illustrates a transmission cell background device 501 in accordance with yet a further embodiment of the present invention. The transmission cell background device 501 also makes use of discrete constituent 520 pathlengths to match the pathlength distribution of tissue at key points. The transmission cell background device 501 includes an optically transparent container 510 such as fused silica windows containing a plurality of spacers 530 such as $MgF_2$ spacers to provide desired pathlengths. The remainder of the container 510 is filled with a constituent 520 such as water. The spacers function to displace the water or other constituent, creating a background with several different length water paths. Suitable dimensions for the cell spacers are 0.226", 0.216", and 0.197", respectively. These spacers may be used to create three water layers with thickness values of 0.0098", 0.0197", and 0.0393". The diameter of the transmission cell 501 is chosen to match the output area of the sampling optics for a given device. FIG. 49 shows a graph of spectral response demonstrating the spectral match between the tissue sample and the transmission cell background 501. FIG. 49 indicates the degree of match between the transmission cell (T-Cell) background 501 and the tissue sample to be on the order of +/−0.1 absorbance units.

The transmission cell background 501 may be incorporated into a transmission spectroscopy device by incorporating a second, reflective element (not shown). The transmission cell described above is placed into the optical beam of the spectrometer in a location such that the light from the sampling optics passes through the transmission cell before being measured by the optical detector. A diffusely reflecting material, such as Spectralon, is placed at the tissue sampler interface in order to mimic the bulk scattering properties of tissue. This optical setup allows a similar background to be constructed that uses discrete water pathlengths in transmission to mimic the optical properties of tissue sampled using reflection sampling optics.

Figure 48:
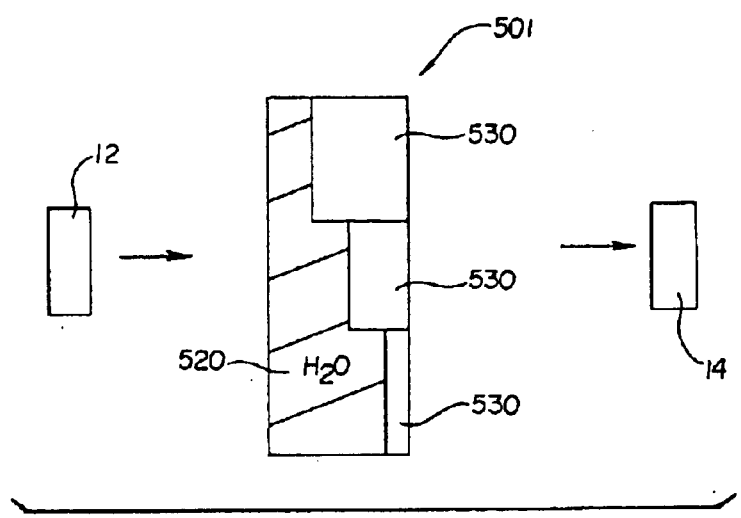
FIG. 48 schematically illustrates a transmission cell background in accordance with an embodiment of the present invention.
Figure 49:
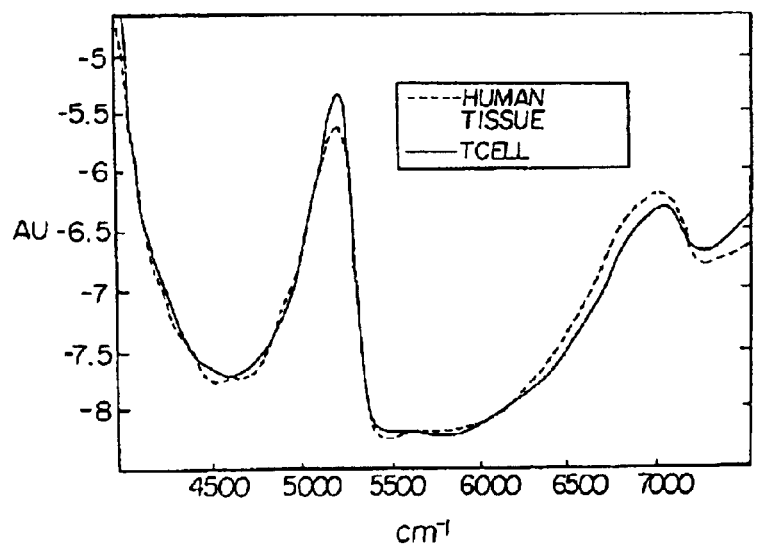
FIG. 49 shows a graph of spectral response demonstrating the spectral match between the tissue sample and the transmission cell background.

The transmission reference sample, as shown in FIG. 48, has three different optical pathlengths. When examined by the multipath RMS error metric over the region of 4200–7200 $cm^{-1}$, the magnitude of the residual clearly indicates the presence of multiple pathlengths through generation of a value of approximately 0.11 absorbance units.

Figure 50:
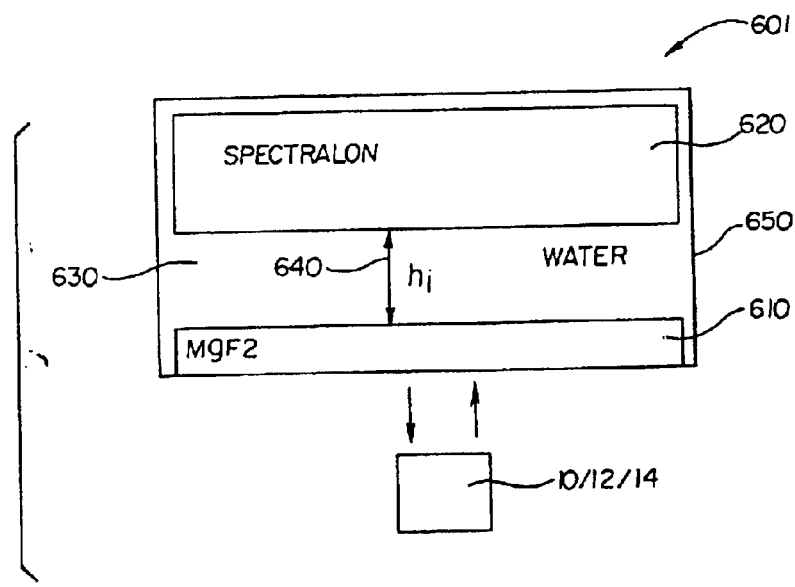
FIG. 50 schematically illustrates a variable height temporal background in accordance with an embodiment of the present invention.

Refer now to FIG. 50, which schematically illustrates a variable height temporal background device 601 in accordance with another embodiment of the present invention. The temporal background device 601 includes an optically transparent layer 610 and a movable diffuse reflector layer 620, such as a Spectralon. A constituent layer 630 such as water is disposed between the optically transparent layer 610 and the diffuse reflector 620. The optically transparent layer 610 may be used to contain the constituent layer 630 or a separate container 650 may be provided for that purpose.

Figure 51:
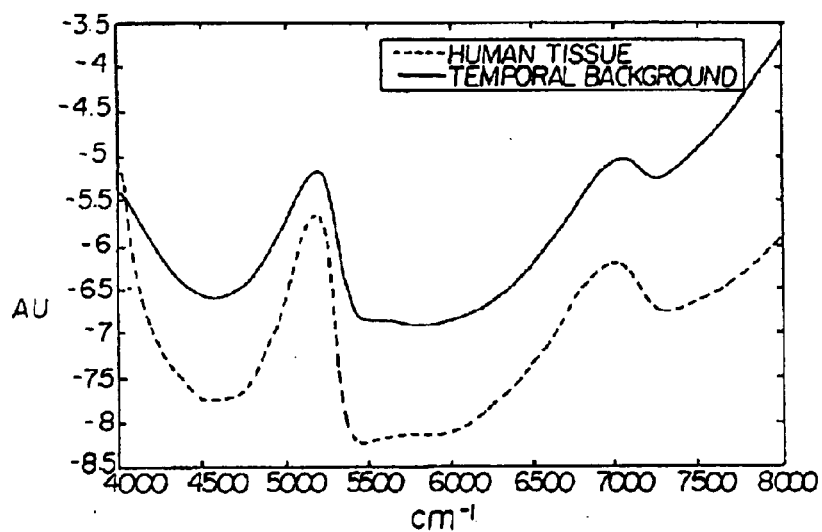
FIG. 51 shows a graph of spectral response demonstrating the spectral match between the tissue sample and the variable height temporal background.

The temporal background device 601 uses a time-weighted sampling technique to produce proper throughput at various pathlengths that match the tissue path distribution. This, in turn, enables the spectral match to tissue. A diffuse reflector 620 (approximately Lambertian high-reflectance material) is used to provide return illumination in the form of reflected light and is translated vertically (as shown by arrow 640 and labeled $h_i$) to achieve a variable water path. The data presented below were generated by varying the height of the Spectralon reflector 620 over the water layer $h_i$ through values ranging from 0.1 mm to 0.3 mm. The diameters of the $MgF_2$ window and Spectralon reflector are chosen to match the output area of the sampling optics for a given device. Thus, the reflecting layer 620 is moved to a height corresponding to a given pathlength in the desired distribution, and light is subjected to this pathlength and collected for a lime proportional to the weight of the particular path in the distribution. Upon combination of the time-sampled data, a match to the tissue spectrum can be achieved as shown in FIG. 51.

Figure 52:
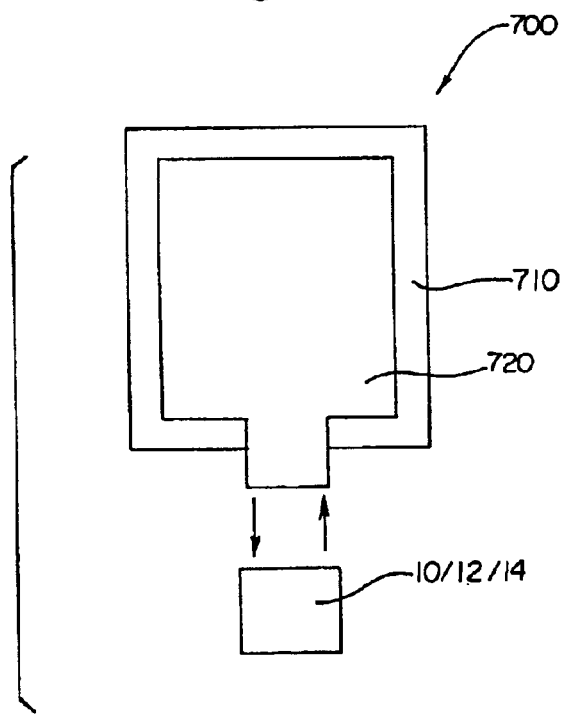
FIG. 52 schematically illustrates a collagen gel matrix background in accordance with an embodiment of the present invention.
Figure 53:
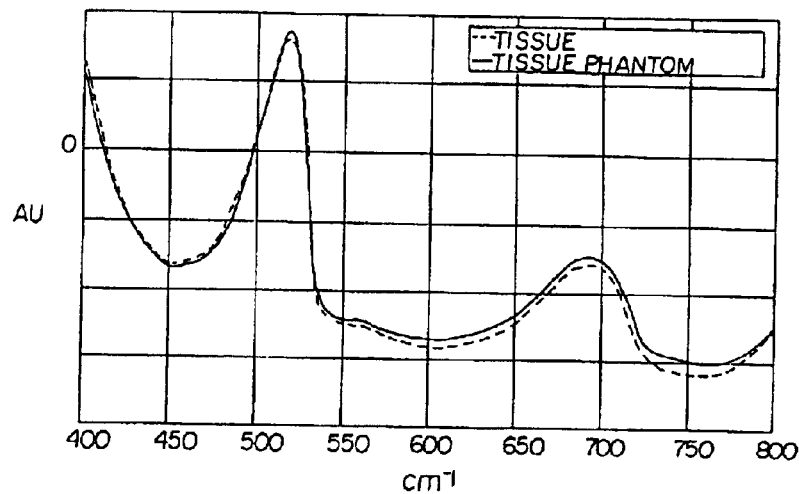
FIG. 53 shows a graph of spectral response demonstrating the spectral match between the tissue sample and the collagen gel matrix background.

Refer now to FIG. 52, which schematically illustrates a collagen gel matrix background device 700 in accordance with an embodiment of the present invention. The collagen gel matrix background device 700 includes a container 710 that is partially optically transparent. A constituent 720 is disposed in the container and comprises a collagen gel matrix. The collagen gel matrix may consist of denatured porcine collagen in a gel state. Reflectance microbeads may be infused into the gel to create a randomized scattering path throughout the volume of the constituent 720. For example, the collagen matrix 720 may be made from 30% porcine gelatin, 0.8% 2 $\mu$m polystyrene beads, and 69.2% water. FIG. 53 shows a graph of spectral response demonstrating the spectral match between the tissue sample spectrum and the collagen gel matrix background spectrum 700. The actual gel thickness presented to the sampling system was 3.0 cm–4.0 cm. As can be seen from FIG. 53, a close match to human tissue can be made if the proper preparation of the collagen gelatin matrix is carried out, which can be accomplished empirically. It is recognized that the gel matrix can be composed of any substance that enables an optically similar reference sample to be created.

Figure 54:
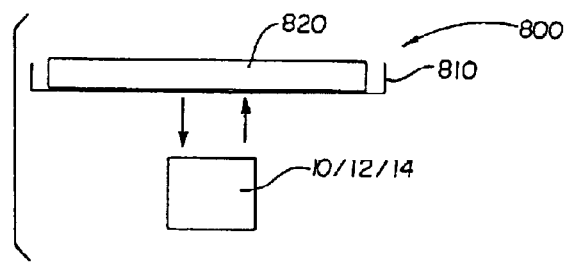
FIG. 54 schematically illustrates an animal tissue (bovine) background in accordance with an embodiment of the present invention.
Figure 55:
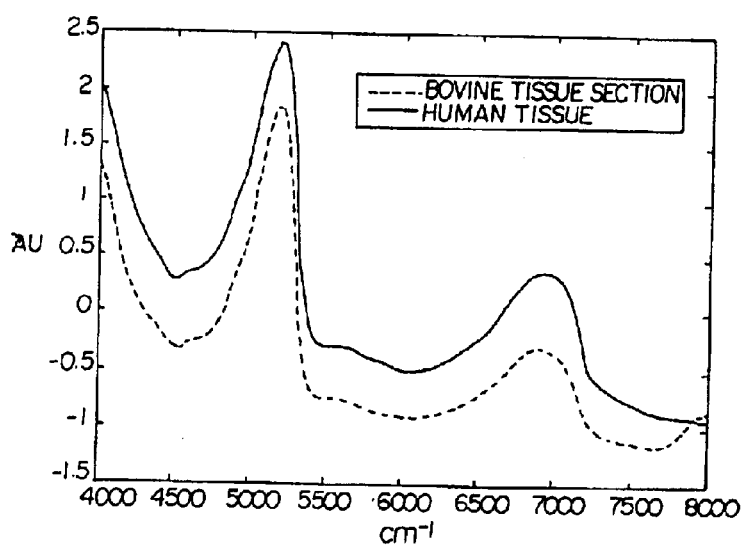
FIG. 55 shows a graph of spectral response demonstrating the spectral match between the tissue sample and the bovine tissue background.

Refer now to FIG. 54, which schematically illustrates an animal based bodily constituent (e.g., bovine tissue) background device 800 in accordance with an embodiment of the present invention. The animal based bodily constituent background 800 includes a container 810 that is at least partially optically transparent and an animal (e.g., bovine, porcine) based bodily constituent 820 disposed therein. The animal based bodily constituent may comprise an animal bodily tissue (e.g., skin), an animal bodily fluid (e.g., blood)

or other animal based biological constituent. Through the use of a section of bovine tissue, a relative match to human tissue is readily attained. The bovine tissue section may be doped with analytes in order to simulate various in-vivo concentration levels for humans. Because the spectral features of the bovine tissue section are similar to those found in human tissue, it provides a good formulation of a tissue similar background for use in calibration maintenance. FIG. 55 shows a graph of spectral response demonstrating the spectral match between the tissue sample and the bovine tissue background 800. For the data shown in FIG. 55, 2 cm×4 cm rectangular sections of bovine collagen tissue approximately 1 cm thick were used. The bovine collagen sample comprised a section of cowhide immersed in distilled water to prevent dehydration.

In use as a subsystem of the present invention, any of the calibration maintenance devices having similar backgrounds discussed above is optically coupled (e.g., positioned adjacent) to the illumination source and irradiated with multiple wavelengths of radiation from the illumination source. The collection system is used to collect radiation that is not absorbed by the reference sample. The collected radiation is then used to determine the intensities of the non-absorbed radiation at each of the multiple wavelengths to generate a reference spectrum. A new calibration model can be created or a pre-existing calibration model can be modified based on the reference spectrum to account for instrument and environment variations. Alternatively, the reference spectrum is simply used to alter a spectrum of a test sample to account for instrument and environment variations without altering an existing model.

After the calibration model has been created or modified, a test sample of interest is optically coupled (e.g., positioned adjacent) to the tissue sampler. The test sample (e.g., human tissue or blood) is irradiated with multiple wavelengths of radiation from the tissue sampler. Radiation that is not absorbed by the test sample is collected by the tissue sampler collection system. The collected radiation is then used to determine the intensities of the non-absorbed radiation at each of the multiple wavelengths to generate a test spectrum corresponding to the test sample of interest. In one embodiment, the newly created or modified calibration model is used, and an analyte or attribute of the test sample may be calculated based on the test spectrum. Alternatively, the test sample spectrum is modified based on the reference spectrum (i.e., a ratio or difference) and the modified test spectrum is used with an existing model to determine an analyte concentration or attribute.

Note that these steps may be reordered and/or modified without departing from the scope of the present invention. For example, the reference sample may have the same or separate interface with the instrument as that used for the test sample of interest. Also, the reference sample may have multiple components that are simultaneously measured at different locations in the optical path of the spectroscopic instrument. Further, the reference sample may be manually or automatically positioned and measured.

In order to correct for the effects of instrument and environmental variation, the similar background is preferably sampled sufficiently close in time to the sample of interest. The required frequency of sampling for the background is dependent on instrument stability and environmental variations which are being corrected. Preferably, a background measurement is made just prior to measuring the sample of interest which allows the most current instrument state to be determined. In an alternative sampling scheme, the signal-to-noise ratio in the measured background spectrum is improved by taking multiple similar background measurements prior to measuring the sample of interest.

There are several schemes for optimizing the relationship between using multiple background sample measurements (higher signal-to-noise) and using only the background sample measurement made closest in time to the measurement of the sample of interest (most current instrument state). One such scheme is to use multiple, weighted, time-averaged background sample measurements. Multiple background sample measurements are collected over a period of time in order to increase the spectrum's signal-to-noise ratio. Weighted averaging allows those background sample spectra taken closest in time to the sample of interest to more heavily influence the spectral correction.

There are multiple methods for using the spectral measurement of the similar background to correct for instrument and environmental variation. One simple and effective methodology is to ratio the measured spectrum of the sample of interest to the measured spectrum of the similar background sample. This correction methodology removes spectral variation that is common to both the similar background and the sample of interest. This methodology may be used to both establish and maintain a multivariate calibration model, but in some cases, it is desirable to use this methodology only for calibration maintenance.

After generating a glucose prediction, the embedded computer subsystem 600 will report the predicted value 830 to the subject. Optionally, the embedded computer subsystem 600 may report the level of confidence in the goodness of the predicted value. If the confidence level is low, the embedded computer subsystem 600 may withhold the predicted glucose value and ask the subject to retest. The glucose values may be reported visually on a display, by audio and/or by printed means. Additionally, the predicted glucose values will be stored in memory in order to form a historical record of the subject's glucose values over time. The number of recorded glucose values is constrained only by the amount of memory contained in the device.

The embedded computer subsystem 600 includes a central processing unit (CPU), memory, storage, a display and preferably a communication link. An example of a CPU is the Intel Pentium microprocessor. The memory can be static random access memory (RAM) and/or dynamic random access memory. The storage can be accomplished with non-volatile RAM or a disk drive. A liquid crystal display is an example of the type of display that would be used in the device. The communication link could be a high speed serial link, an Ethernet link or a wireless communication link. The embedded computer subsystem produces glucose predictions from the received and processed interferograms, performs calibration maintenance, performs calibration transfer, runs instrument diagnostics, stores a history of measured glucose concentrations and other pertinent information, and in some embodiments, can communicate with remote hosts to send and receive data and new software updates.

The embedded computer system can also contain a communication link that allows transfer of the subject's glucose prediction records and the corresponding spectra to an external database. In addition, the communication link can be used to download new software to the embedded computer, update the multivariate calibration model, provide information to the subject to enhance the management of their disease, etc. The embedded computer system is very much like an information appliance. Examples of information appliances include personal digital assistants, web-enabled cellular phones and handheld computers.

Figure 56:
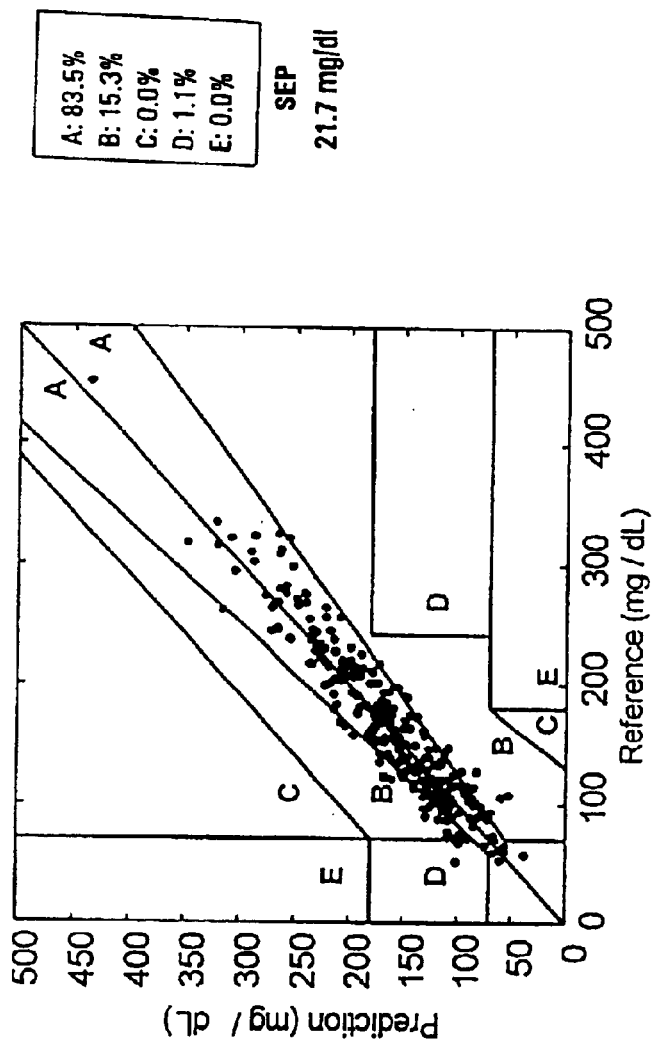
FIG. 56 is a Clark Error Grid which graphically depicts experimental results showing the ability of the system of the present invention to derive clinically relevant glucose measurements in tissue on numerous subjects over two months.

The present invention has been tested to show it achieves clinically relevant levels of glucose prediction and accuracy over a minimum of two months for a diverse subject population. Using the non-invasive glucose monitoring system depicted in FIG. 1, a glucose calibration model was developed on 40 subjects over a period of 6 weeks on 3 identical instruments. The calibration model was validated on 40 new subjects who were not part of the calibration model. The 40-patient validation was conducted over a period of 7 weeks, with each subject being measured twice per week. The results of the validation study are shown in FIG. 56. FIG. 56 displays the correlation between the capillary blood glucose reference measurement (Yellow Springs Instruments 2700 Select) and the glucose concentration predicted by the non-invasive NIR quantitative spectroscopy measurement. This overall standard error of predictions for the 40 subjects over the 7 weeks was 21.7 mg/dl. Further, 83.5% of the results are within section A of the Clark Error Grid. This study demonstrates non-invasive glucose measurements with clinically acceptable levels of accuracy and precision.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An apparatus for non-invasive determination of an attribute of human tissue by quantitative near infrared spectroscopy comprising:
   a. an illumination subsystem which generates near infrared light;
   b. a tissue sampling subsystem, in optical communication with and receiving light from said illumination subsystem, including means for irradiating human tissue with at least a portion of said received light and collecting at least a portion of said light diffusely reflected from said human tissue;
   c. a calibration maintenance subsystem selectively optically coupled to said tissue sampling subsystem for receiving at least a portion of said light and diffusely reflecting a portion thereof;
   d. an FTIR spectrometer subsystem selectively optically coupled to (i) said tissue sampling subsystem to receive at least a portion of said light diffusely reflected from said tissue, or (ii) selectively optically coupled to said calibration maintenance subsystem to receive at least a portion of said infrared light diffusely reflected therefrom, or (iii) a combination thereof, said FTIR spectrometer subsystem including a spectrometer that creates an interferogram, said FTIR spectrometer subsystem further including a detector which receives the interferogram and converts said interferogram to a communicable representation;
   e. a data acquisition subsystem which receives the communicable representation of the interferogram, said data acquisition subsystem including means for modifying said communicable representation and producing an analyzable representation thereof; and
   f. a computing subsystem for receiving said analyzable representation and further including means for determining the attribute from said analyzable representation, wherein in combination said subsystems provide a clinically relevant level of precision and accuracy.

2. The apparatus of claim 1, wherein said calibration maintenance subsystem comprises a reference sample which receives a portion of said infrared light and produces a spectrum similar to a representative human tissue sample.

3. The apparatus of claim 2, wherein the representative human tissue sample includes multiple samples from multiple subjects.

4. The apparatus of claim 3, wherein the reference sample has a spectral similarity ratio, when compared with the representative human tissue sample spectra, of 30 or less over a spectral range of 4,200 cm−1 to 7,200 cm−1.

5. The apparatus of claim 3, wherein the reference sample has a spectral similarity ratio, when compared with the representative human tissue sample spectra, of 30 or less over a spectral range of 4,440 cm−1 to 4,800 cm−1 and 5,440 cm−1 to 6,400 cm−1.

6. The apparatus of claim 3, wherein the reference sample has a regression weighted spectral similarity ratio, when compared to the representative human tissue spectra, of 30 or less over a spectral range of 4,200 cm−1 to 7,200 cm−1.

7. The apparatus of claim 3, wherein the reference sample has a regression weighted spectral similarity ratio, when compared to the representative human tissue sample spectra, of 30 or less over a spectral range of 4,440 cm−1 to 4,800 cm−1 and 5,440 cm−1 to 6,400 cm−1.

8. The apparatus of claim 2, wherein the representative human tissue sample is from a single subject.

9. The apparatus of claim 8, wherein the reference sample has a spectral similarity ratio, when compared with the representative human tissue sample spectra, of 1500 or less over a spectral range of 4,200 cm−1 to 7,200 cm−1.

10. The apparatus of claim 8, wherein the reference sample has a spectral similarity ratio, when compared with the representative human tissue sample spectra, of 7500 or less over a spectral range of 4,440 cm−1 to 4,800 cm−1 and 5,440 cm−1 to 6,400 cm−1.

11. The apparatus of claim 8, wherein the reference sample has a regression weighted spectral similarity ratio, when compared to the representative human tissue sample spectra, of 4500 or less over a spectral range of 4,200 cm−1 to 7,200 cm−1.

12. The apparatus of claim 8, wherein the reference sample has a regression weighted spectral similarity ratio, when compared to the representative human tissue sample spectra, of 9000 or less over a spectral range of 4,440 cm−1 to 4,800 cm−1 and 5,440 cm−1 to 6,400 cm−1.

13. The apparatus of claim 2, wherein the reference sample has a spatial similarity, expressed in terms of standard deviation, of 0.079 or less.

14. The apparatus of claim 2, wherein the reference sample has an angular similarity, expressed in terms of standard deviation, of 0.051 or less.

15. An apparatus for non-invasive determination of an attribute of human tissue by quantitative near infrared spectroscopy comprising:
   a. an illumination subsystem which generates near infrared light;
   b. a tissue sampling subsystem, in optical communication with and receiving light from said illumination subsystem, including means for irradiating human tissue with at least a portion of said received light and collecting at least a portion of said light diffusely reflected from said human tissue;
   c. a calibration maintenance subsystem selectively optically coupled to said tissue sampling subsystem for receiving at least a portion of said light and diffusely reflecting a portion thereof;

d. an FTIR spectrometer subsystem selectively optically coupled to (i) said tissue sampling subsystem to receive at least a portion of said light diffusely reflected from said tissue, or (ii) selectively optically coupled to said calibration maintenance subsystem to receive at least a portion of said infrared light diffusely reflected therefrom, or (iii) a combination thereof, said FTIR spectrometer subsystem including a spectrometer that creates an interferogram, said FTIR spectrometer subsystem further including a detector which receives the interferogram and converts said interferogram to a communicable representation;

e. a data acquisition subsystem which receives the communicable representation of the interferogram, said data acquisition subsystem including means for modifying said communicable representation and producing an analyzable representation thereof; and f. a computing subsystem for receiving said analyzable representation and further including means for determining the attribute from said analyzable representation, wherein in combination said subsystems provide a clinically relevant level of precision and accuracy;

wherein said calibration maintenance subsystem comprises a reference sample which receives a portion of said infrared light and produces a spectrum similar to a representative human tissue sample, and wherein the reference sample comprises a gelling agent, a scattering agent, and water.

16. The apparatus of claim 15, wherein the gelling agent comprises HEC.

17. The apparatus of claim 15, wherein the gelling agent comprises PVA.

18. The apparatus of claim 15, wherein the gelling agent comprises an initiator and a crosslinking agent that contains a plurality of vinyl groups.

19. The apparatus of claim 18, wherein the crosslinking agent comprises N,N'-methylenebisacrylamide, ethylene glycol dimethacrylate, bisacrylamide, or a combination thereof.

20. The apparatus of claim 18, wherein the initiator comprises a peroxide, benzoyl peroxide, a persulfate, ammonium persulfate, azobisisobutyronitrile, a photochemically activated initiator, methylene blue, riboflavin, ammonium persulfate in the presence of TEMED, or a combination thereof.

21. The apparatus of claim 18, wherein the gelling agent further comprises a monomer that contains a vinyl group.

22. The apparatus of claim 21, wherein the monomer comprises acrylamide, 2-hydroxyethyl methacrylate, poly(ethylene glycol) methacrylate, 1-vinyl-2-pyrrolidinone, or a combination thereof.

23. The apparatus of claim 15, wherein the scattering agent comprises a mesh, a three-dimensional structure, a filaments, a particle, or combinations thereof.

24. An apparatus for non-invasive determination of an attribute of human tissue by quantitative near infrared spectroscopy comprising:

a. an illumination subsystem which generates near infrared light, said illumination subsystem including a light homogenizer positioned to receive at least a portion of said infrared light;

b. a tissue sampling subsystem optically coupled to said illumination subsystem which receives at least a portion of said infrared light exiting said light homogenizer, said tissue sampling subsystem including means for irradiating human tissue with at least a portion of said received infrared light and collecting at least a portion of said light diffusely reflected from human tissue;

c. an FTIR spectrometer subsystem selectively optically coupled to said tissue sampling subsystem to receive at least a portion of said light diffusely reflected from said tissue, said FTIR spectrometer subsystem including a spectrometer that creates an interferogram, said FTIR spectrometer subsystem further including a detector which receives the interferogram and converts said interferogram to a communicable representation;

d. a data acquisition subsystem which receives the communicable representation of the interferogram, said data acquisition subsystem including means for modifying said communicable representation and producing an analyzable representation thereof; and e. a computing subsystem for receiving said analyzable representation and further including means for determining the attribute of human tissue from said analyzable representation, wherein in combination said subsystems provide a clinically relevant level of precision and accuracy.

25. The apparatus of claim 24, wherein said light homogenizer comprises a light pipe.

26. The apparatus of claim 25, wherein said light pipe has a polygonal cross section.

27. The apparatus of claim 25, wherein said light pipe includes one or more bends.

28. The apparatus of claim 25, wherein said light pipe includes a diffusely reflective coating on the interior surface thereof.

29. The apparatus of claim 24, wherein the light homogenizer comprises a glass diffuser.

30. The apparatus of claim 24, wherein said illumination subsystem further comprises a filament which generates said light and said light homogenizer sufficiently homogenizes said light so that light which contacts the human tissue has a spatial and angular distribution which is repeatable through a one-millimeter vertical translation of the filament resulting in a standard deviation of less than 0.053 in spatial distribution and a standard deviation of less than 0.044 in angular distribution.

31. The apparatus of claim 24, wherein said illumination subsystem further comprises a light source including a filament generating said light, wherein the light contacting the human tissue has a spatial and angular distribution which is repeatable through a one-millimeter rotational translation of the filament resulting in a standard deviation of less than 0.050 in spatial distribution and a standard deviation of less than 0.066 in angular distribution.

32. The apparatus of claim 24, wherein the illumination subsystem includes a light source and the light homogenizer produces sufficient angular and spatial homogenization so that the inverse multivariate signal-to-noise value is about 60 or less when the light source is changed in the illumination subsystem.

33. The apparatus of claim 24, wherein the illumination subsystem includes a light source that comprise a tungsten-halogen lamp.

34. The apparatus of claim 24, wherein said light generated by said illumination subsystem possesses a band of wavelengths within the infrared regions of the electromagnetic spectrum.

35. The apparatus of claim 34, wherein the illumination subsystem further comprises means for concentrating the radiation emitted by the radiation source emitter.

36. The apparatus of claim 24, wherein the sampling subsystem comprises means for channeling at least a portion of the light exiting the light homogenizer to the human tissue.

37. The apparatus of claim 36, wherein the channeling means comprises at least one fiber optic wire.

38. The apparatus of claim 36, wherein the channeling means comprises at least one mirror.

39. The apparatus of claim 36, wherein the channeling means is at least one optic lens.

40. An apparatus for non-invasive determination of an attribute of human tissue by quantitative near infrared spectroscopy comprising:
 a. an illumination subsystem which generates near infrared light including means for angularly and spatially homogenizing at least a portion of said light;
 b. a tissue sampling subsystem optically coupled to said illumination subsystem which receives at least a portion of said infrared light, said tissue sampling subsystem including means for irradiating human tissue with at least a portion of said received infrared light and collecting at least a portion of said light diffusely reflected from said human tissue, said tissue sampling subsystem including at least one input element which transfers said light to said human tissue and at least one output element which receives light from said tissue, wherein said input element and said output element are spaced apart by a gap of about 100 μm or greater;
 c. a calibration maintenance subsystem selectively optically coupled to said tissue sampling subsystem for receiving at least a portion of said infrared light and diffusely reflecting a portion thereof, said calibration maintenance subsystem including a reference sample having optical properties similar to a representative human tissue sample;
 d. an FTIR spectrometer subsystem selectively optically coupled to said tissue sampling subsystem to receive at least a portion of said light diffusely reflected from said tissue or selectively optically coupled to said calibration maintenance subsystem to receive at least a portion of said infrared light diffusely reflected therefrom, said FTIR spectrometer subsystem including a spectrometer that creates an interferogram, said FTIR spectrometer subsystem further including a detector which receives the interferogram and converts said interferogram to a communicable representation, said detector that is sensitive to light in the 1.2 to 2.5 μm region of the spectrum;
 e. a data acquisition subsystem with a minimum SNR of 100 dbc which receives the communicable representation of the interferogram, said data acquisition subsystem including means for modifying said communicable representation and an analog-to-digital converter for converting a resulting electrical signal to its digital representation; and
 f. a computing subsystem for receiving said digital representation and further including means for determining the attribute from said digital representation, wherein in combination said subsystems provide a clinically relevant level of precision and accuracy.

41. The apparatus of claim 40, wherein said detector is a thermoelectrically cooled, extended range InGaAs detector that is sensitive to light in the 1.2 to 2.5 mm region of the spectrum.

42. The apparatus of claim 40, wherein said input element and said output element comprise, at least in part, optical fibers.

43. The apparatus of claim 42, wherein said optical fibers have ends potted into a cluster ferrule which is mounted in said sampling head.

44. The apparatus of claim 40, wherein said cradle includes a base having an opening therethrough in which said sample head is disposed.

45. The apparatus of claim 44, wherein said means for positioning human tissue relative to said sampling surface comprises a bracket extending upward from said base which references an elbow of a subject's arm disposed thereon.

46. The apparatus of claim 45, wherein said cradle further includes an adjustable hand rest spaced longitudinally from said bracket along said base.

47. The apparatus of claim 46, further including means for raising and lowering said cradle to form and reform the tissue interface.

48. The apparatus of claim 40, wherein the input element surface area is at least seven times greater than the output element surface area.

49. An apparatus for non-invasive determination of an attribute of human tissue by quantitative near-infrared spectroscopy comprising:
 a. an illumination subsystem which generates near-infrared light;
 b. a tissue sampling subsystem optically coupled to said illumination subsystem which receives at least a portion of said infrared light generated by said illumination subsystem, said tissue sampling subsystem including means for irradiating human tissue with at least a portion of said received infrared light and collecting at least a portion of said light diffusely reflected from human tissue, said means for irradiating human tissue including at least one input element which transfers said light to said human tissue and at least one output element which receives light from said tissue;
 c. an FTIR spectrometer subsystem selectively optically coupled to said tissue sampling subsystem to receive at least a portion of said light diffusely reflected from said tissue, said FTIR spectrometer subsystem including a spectrometer that creates an interferogram, said FTIR spectrometer subsystem further including a detector which receives the interferogram and converts said interferogram to a communicable representation, said detector that is sensitive to light in the 1.2 to 2.5 μm region of the spectrum;
 d. a data acquisition subsystem which receives the communicable representation of the interferogram, said data acquisition subsystem including means for modifying said communicable representation and producing an analyzable representation thereof; and
 e. a computing subsystem for receiving said analyzable representation and further including means for determining the attribute from said analyzable representation, wherein in combination said subsystems provide a clinically relevant level of precision and accuracy;
wherein said detector is a thermoelectrically cooled, extended range InGaAs detector that is sensitive to light in the 1.2 to 2.5 mm region of the spectrum.

* * * * *